US009029509B2

(12) United States Patent
Craik et al.

(10) Patent No.: US 9,029,509 B2

(45) Date of Patent: May 12, 2015

(54) ANTIBODIES AND PHARMACEUTICAL COMPOSITIONS THEREOF WHICH BIND UROKINASE-TYPE PLASMINOGEN ACTIVATOR RECEPTOR (UPAR)

(75) Inventors: Charles S. Craik, San Francisco, CA (US); Krishna Sai Duriseti, San Francisco, CA (US); David H. Goetz, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 81 days.

(21) Appl. No.: 13/522,653

(22) PCT Filed: Feb. 11, 2011

(86) PCT No.: PCT/US2011/024636

§ 371 (c)(1), (2), (4) Date: Sep. 21, 2012

(87) PCT Pub. No.: WO2011/100620

PCT Pub. Date: Aug. 18, 2011

(65) Prior Publication Data

US 2013/0052128 A1 Feb. 28, 2013

Related U.S. Application Data

(60) Provisional application No. 61/304,334, filed on Feb. 12, 2010.

(51) Int. Cl.

| | |
|---|---|
| ***C07K 16/00*** | (2006.01) |
| ***C07K 17/00*** | (2006.01) |
| ***C07K 17/14*** | (2006.01) |
| ***C12P 21/08*** | (2006.01) |
| ***A61K 51/00*** | (2006.01) |
| ***A61M 36/14*** | (2006.01) |
| ***A61K 39/395*** | (2006.01) |
| ***A61K 39/00*** | (2006.01) |
| ***C07K 16/28*** | (2006.01) |
| ***A61K 47/48*** | (2006.01) |
| ***G01N 33/566*** | (2006.01) |
| ***G01N 33/574*** | (2006.01) |

(52) U.S. Cl.

CPC ......... *C07K 16/2896* (2013.01); *A61K 47/4833* (2013.01); *A61K 2039/505* (2013.01); *C07K 2317/21* (2013.01); *C07K 2317/55* (2013.01); *C07K 2317/73* (2013.01); *C07K 2317/76* (2013.01); *C07K 2317/92* (2013.01); *G01N 33/566* (2013.01); *G01N 33/57415* (2013.01); *G01N 2333/70546* (2013.01); *C07K 2317/34* (2013.01)

(58) Field of Classification Search

None

See application file for complete search history.

(56) References Cited

U.S. PATENT DOCUMENTS

| | | | | |
|---|---|---|---|---|
| 6,120,765 | A * | 9/2000 | Hibino et al. | 424/94.63 |
| 7,928,203 | B2 * | 4/2011 | Schenk et al. | 530/387.3 |
| 2003/0070185 | A1 | 4/2003 | Jakobovits et al. | |
| 2003/0099647 | A1 | 5/2003 | Deshpande et al. | |
| 2005/0044589 | A1 | 2/2005 | Buchter-Larsen et al. | |
| 2008/0199476 | A1 * | 8/2008 | Parry et al. | 424/139.1 |

FOREIGN PATENT DOCUMENTS

| | | |
|---|---|---|
| WO | 2001017544 | 3/2001 |
| WO | 2007120693 | 10/2007 |

OTHER PUBLICATIONS

Colman, PM. Research in Immunology, Elsevier, NY, 145(1):33-36, 1994.*

Paul, WE. Fundamental Immunology, 3rd ed. Raven Press, NY, Chap. 9, pp. 292-295, 1993.*

Rudikoff S. et al. Proc. Natl. Acad. Sci. USA, 79:1979-1983, 1982.*

Mazar (2008) "Urokinase plasminogen activator receptor choreographs multiple ligand interactions: implications for tumor progression and therapy" Clin Cancer Res 14(18):5649-5655.

Rabbani & Gladu et al. (2002) "Urokinase receptor antibody can reduce tumor volume and detect the presence of occult tumor metastases in vivo" Cancer Res 62(8):2390-2397.

Rønne et al. (1991) "Cell-induced potentiation of the plasminogen activation system is abolished by a monoclonal antibody that recognizes the NH2-terminal domain of the urokinase receptor" FEBS Lett 288(1-2):233-236.

Bénard & Turcotte (2005) "Imaging in breast cancer: Single-photon computed tomography and positron-emission tomography" Breast Cancer Res 7(4):153-162.

Duriseti (2010) "Antagonistic anti-urokinase plasminogen activator receptor (uPAR) antibodies significantly inhibit uPAR-mediated cellular signaling and migration" J Biol Chem 285(35):26878-26888.

Van Der Pluijm et al. (2001) "Urokinase-receptor/integrin complexes are functionally involved in adhesion and progression of human breast cancer in vivo" Amer J Pathol 159(3):971-982.

Wei et al. (2001) "Urokinase receptors promote β1 integrin function through interactions with integrin α3β1" Mol Biol Cell 12(10):2975-2986.

Yerba et al. (1996) "Requirement of receptor-bound urokinase-type plasminogen activator for integrin alphavbeta5-directed cell migration" J Biol Chem 271(46):29393-29399.

* cited by examiner

*Primary Examiner* — Robert Landsman

(74) *Attorney, Agent, or Firm* — Carol L. Francis; Brian E. Davy; Bozicevic, Field & Francis LLP

(57) ABSTRACT

The present disclosure relates to binding agents (e.g. antibodies) that bind to and/or modulate the activity of a urokinase plasminogen activator receptor (uPAR/CD87), compositions comprising the antibodies, and methods involving use of the antibodies or compositions.

15 Claims, 16 Drawing Sheets

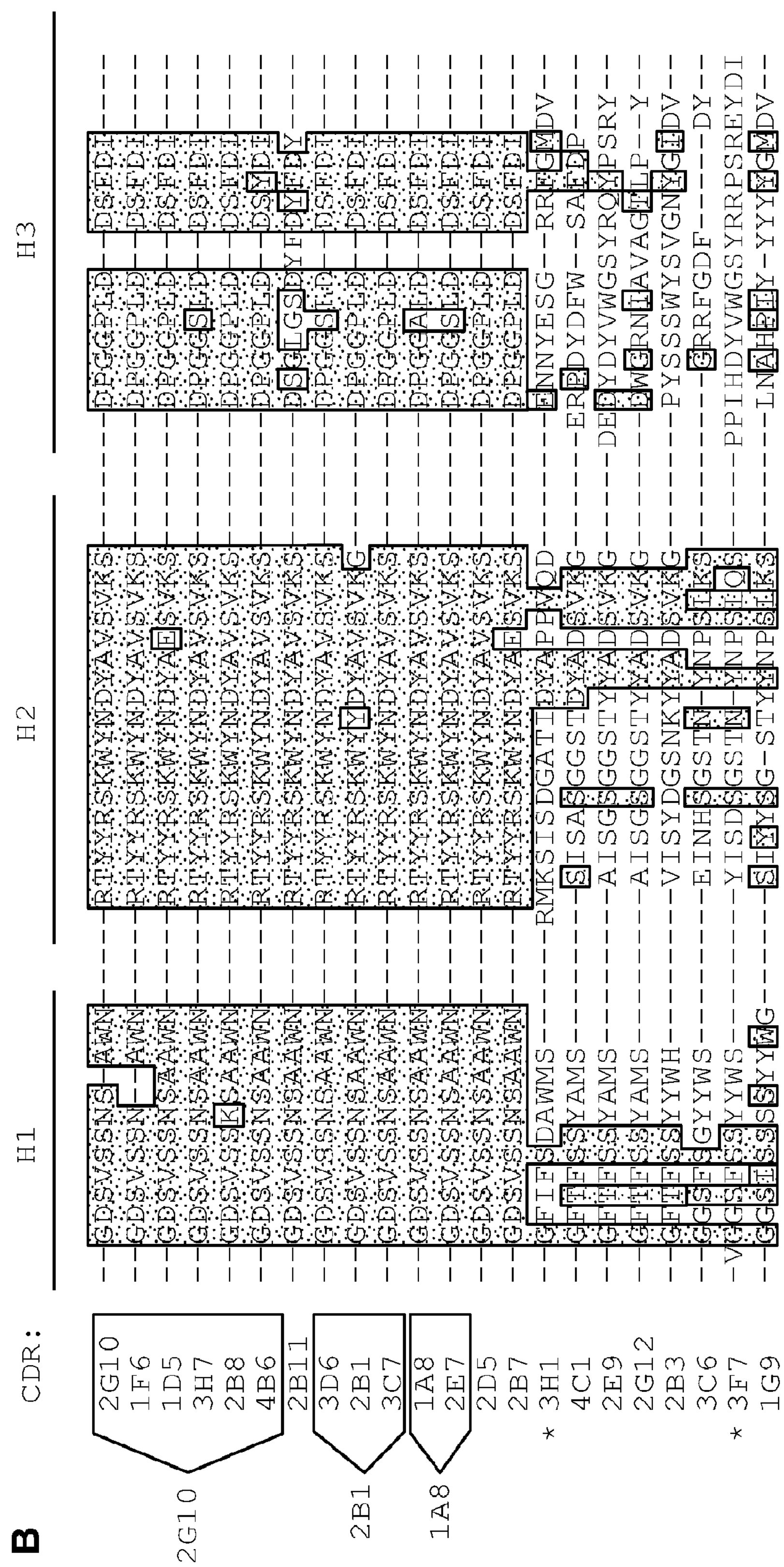
FIG. 1 (Cont. 1)

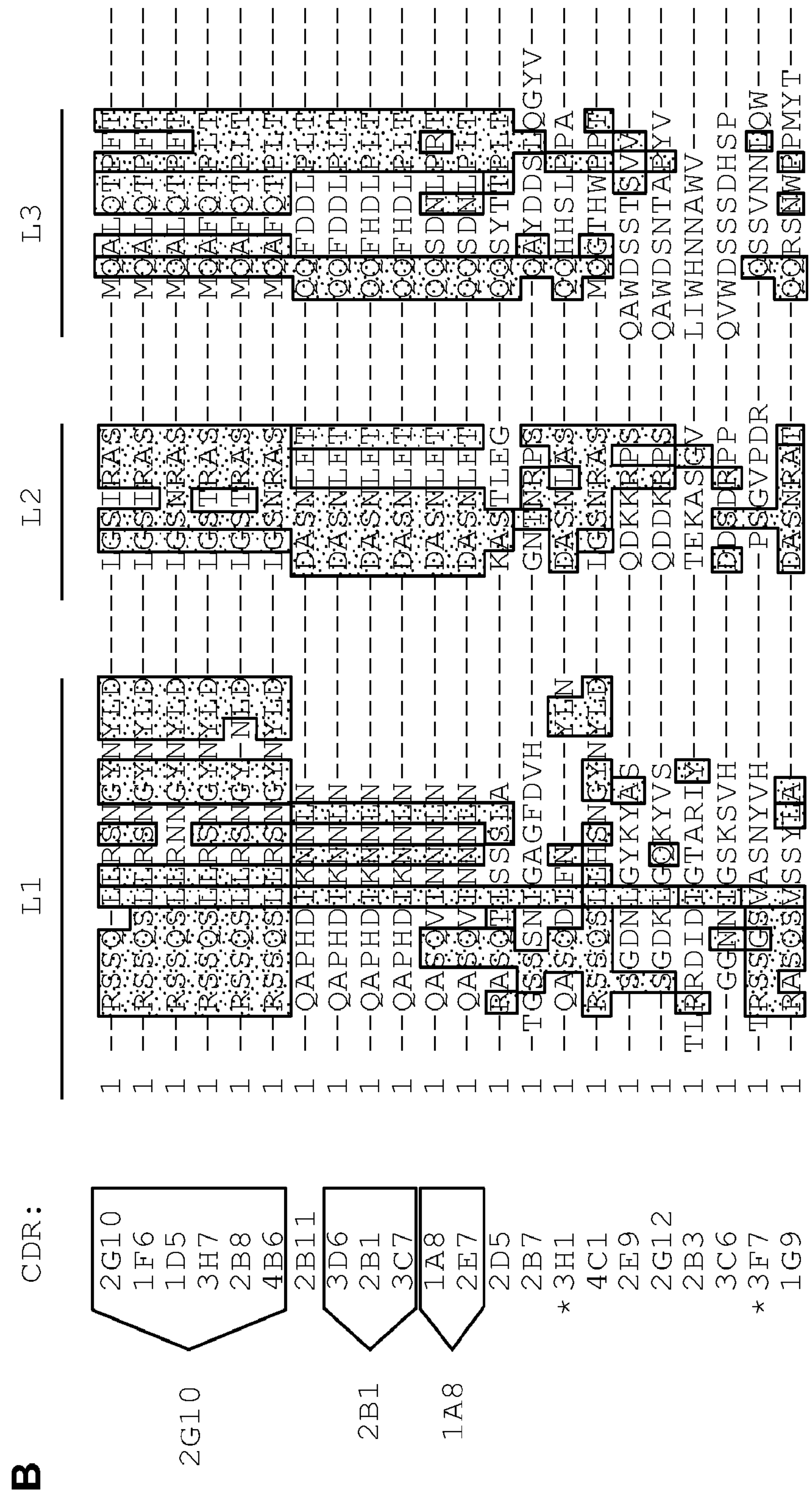
FIG.1 (Cont. 2)

| Antibody | 1A8 | 2B1 | 2E9 | 2G10 |
|---|---|---|---|---|
| Kd (nM) | 23.8+/-0.2 | 53.5+/-0.2 | 9.2+/-0.02 | 40.5+/-0.1 |

A

B

C

SEQUENCE LISTING

```
<160> NUMBER OF SEQ ID NOS: 153

<210> SEQ ID NO 1
<211> LENGTH: 281
<212> TYPE: PRT
<213> ORGANISM: Homo sapiens

<400> SEQUENCE: 1

Leu Arg Cys Met Gln Cys Lys Thr Asn Gly Asp Cys Arg Val Glu Glu
1               5                   10                  15

Cys Ala Leu Gly Gln Asp Leu Cys Arg Thr Thr Ile Val Arg Leu Trp
            20                  25                  30

Glu Glu Gly Glu Glu Leu Glu Leu Val Glu Lys Ser Cys Thr His Ser
        35                  40                  45

Glu Lys Thr Asn Arg Thr Leu Ser Tyr Arg Thr Gly Leu Lys Ile Thr
    50                  55                  60

Ser Leu Thr Glu Val Val Cys Gly Leu Asp Leu Cys Asn Gln Gly Asn
65                  70                  75                  80

Ser Gly Arg Ala Val Thr Tyr Ser Arg Ser Arg Tyr Leu Glu Cys Ile
                85                  90                  95

Ser Cys Gly Ser Ser Asp Met Ser Cys Glu Arg Gly Arg His Gln Ser
            100                 105                 110

Leu Gln Cys Arg Ser Pro Glu Glu Gln Cys Leu Asp Val Val Thr His
        115                 120                 125

Trp Ile Gln Glu Gly Glu Glu Gly Arg Pro Lys Asp Asp Arg His Leu
    130                 135                 140

Arg Gly Cys Gly Tyr Leu Pro Gly Cys Pro Gly Ser Asn Gly Phe His
145                 150                 155                 160

Asn Asn Asp Thr Phe His Phe Leu Lys Cys Cys Asn Thr Thr Lys Cys
                165                 170                 175

Asn Glu Gly Pro Ile Leu Glu Leu Glu Asn Leu Pro Gln Asn Gly Arg
            180                 185                 190

Gln Cys Tyr Ser Cys Lys Gly Asn Ser Thr His Gly Cys Ser Ser Glu
        195                 200                 205

Glu Thr Phe Leu Ile Asp Cys Arg Gly Pro Met Asn Gln Cys Leu Val
    210                 215                 220

Ala Thr Gly Thr His Glu Pro Lys Asn Gln Ser Tyr Met Val Arg Gly
225                 230                 235                 240

Cys Ala Thr Ala Ser Met Cys Gln His Ala His Leu Gly Asp Ala Phe
                245                 250                 255

Ser Met Asn His Ile Asp Val Ser Cys Cys Thr Lys Ser Gly Cys Asn
            260                 265                 270

His Pro Asp Leu Asp Val Gln Tyr Arg
        275                 280

<210> SEQ ID NO 2
<211> LENGTH: 228
<212> TYPE: PRT
```

<213> ORGANISM: Mus musculus

<400> SEQUENCE: 2

Gln Leu Gln Leu Gln Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Pro Tyr Ser Ser Ser Trp Tyr Ser Val Gly Asn Tyr Gly Ile
100 105 110

Asp Val Trp Gly Gln Gly Thr Thr Val Thr Val Ser Ser Ala Ser Thr
115 120 125

Lys Gly Pro Ser Val Phe Pro Leu Ala Pro Ser Ser Lys Ser Thr Ser
130 135 140

Gly Gly Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Lys Val Glu
210 215 220

Pro Lys Ser Cys
225

<210> SEQ ID NO 3
<211> LENGTH: 221
<212> TYPE: PRT
<213> ORGANISM: Mus musculus

<400> SEQUENCE: 3

Gln Ala Val Leu Thr Gln Pro Ser Ser Leu Ser Ala Ser Pro Gly Ala
1 5 10 15

Ser Ala Ser Leu Thr Cys Thr Leu Arg Arg Asp Ile Asp Ile Gly Thr
20 25 30

Ala Arg Ile Tyr Trp Tyr Gln Gln Lys Pro Gly Ser Pro Pro Gln Tyr
35 40 45

Leu Leu Asn Tyr Lys Ser Asp Leu Tyr Thr Glu Lys Ala Ser Gly Val
50 55 60

Pro Ser Arg Phe Ser Gly Ser Lys Asp Ala Ser Ala Asn Ala Gly Ile
65 70 75 80

Leu Leu Ile Ser Gly Leu Gln Ser Glu Asp Glu Ala Asp Tyr Tyr Cys
85 90 95

Leu Ile Trp His Asn Asn Ala Trp Val Phe Gly Gly Gly Thr Lys Leu
100 105 110

Thr Val Leu Gly Gln Pro Lys Ala Ala Pro Ser Val Thr Leu Phe Pro

```
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Gly Ser Pro Val Lys Ala Gly Val Glu Thr Thr Lys Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220


<210> SEQ ID NO 4
<211> LENGTH: 227
<212> TYPE: PRT
<213> ORGANISM: Mus musculus

<400> SEQUENCE: 4

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Glu Ser Val Lys Ser Arg Ile Val Ile Asn Val Asp Thr Ser Lys Asn
65                  70                  75                  80

Gln Phe Ser Leu Gln Leu Asn Ser Val Thr Pro Glu Asp Thr Ala Ala
                85                  90                  95

Tyr Tyr Cys Ala Arg Asp Pro Gly Gly Pro Leu Asp Asp Ser Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225


<210> SEQ ID NO 5
<211> LENGTH: 217
<212> TYPE: PRT
<213> ORGANISM: Mus musculus
```

<400> SEQUENCE: 5

```
Gln Ser Val Val Thr Gln Pro Pro Ser Val Ser Gly Ala Pro Gly Gln
1               5                   10                  15

Arg Val Ile Ile Ser Cys Thr Gly Ser Ser Ser Asn Ile Gly Ala Gly
            20                  25                  30

Phe Asp Val His Trp Tyr Gln Gln Leu Pro Gly Thr Val Pro Lys Leu
        35                  40                  45

Leu Ile Tyr Gly Asn Thr Asn Arg Pro Ser Gly Val Pro Asp Arg Phe
    50                  55                  60

Ser Gly Ser Lys Ala Gly Thr Ser Ala Ser Leu Ala Ile Thr Gly Leu
65                  70                  75                  80

Gln Ala Glu Asp Glu Ala Asp Tyr Tyr Cys Gln Ala Tyr Asp Asp Ser
                85                  90                  95

Leu Gln Gly Tyr Val Phe Gly Thr Gly Thr Lys Leu Thr Val Val Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 6
<211> LENGTH: 227
<212> TYPE: PRT
<213> ORGANISM: Mus musculus

<400> SEQUENCE: 6

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Gly Gly Pro Leu Asp Asp Ser Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140
```

```
Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Tyr
        195                 200                 205

Val Asn His Lys Pro Ser Asn Thr Lys Val Asp Lys Lys Val Glu Pro
    210                 215                 220

Lys Ser Cys
225


<210> SEQ ID NO 7
<211> LENGTH: 220
<212> TYPE: PRT
<213> ORGANISM: Mus musculus

<400> SEQUENCE: 7

Leu Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu Arg
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Thr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Phe Gln Thr Pro Leu Thr Phe Gly Gly Gly Thr Lys Met Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 8
<211> LENGTH: 226
<212> TYPE: PRT
<213> ORGANISM: Mus musculus

<400> SEQUENCE: 8

Gln Val Gln Leu Gln Gln Ser Gly Pro Gly Leu Val Lys Pro Ser Gln
1               5                   10                  15
```

```
Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Gly Leu Gly Ser Asp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys
225


<210> SEQ ID NO 9
<211> LENGTH: 215
<212> TYPE: PRT
<213> ORGANISM: Mus musculus

<400> SEQUENCE: 9

Leu Asp Ile Gln Met Thr Gln Ser Pro Pro Ser Leu Ser Ala Ser Val
1               5                   10                  15

Gly Asp Arg Val Thr Ile Thr Cys Gln Ala Pro His Asp Ile Lys Asn
            20                  25                  30

Asn Leu Asn Trp Tyr Gln Gln Lys Pro Gly Lys Ala Pro Lys Leu Leu
        35                  40                  45

Ile Phe Asp Ala Ser Asn Leu Glu Thr Gly Val Pro Ser Arg Phe Ser
    50                  55                  60

Gly Ser Gly Ser Gly Thr Asn Phe Val Leu Thr Ile Ser Ser Leu Gln
65                  70                  75                  80

Pro Glu Asp Ile Ala Thr Tyr Tyr Cys Gln Gln Phe Asp Asp Leu Pro
                85                  90                  95

Leu Thr Phe Gly Gly Gly Thr Lys Val Asp Met Lys Arg Thr Val Ala
            100                 105                 110

Ala Pro Ser Val Phe Ile Phe Pro Pro Ser Asp Glu Gln Leu Glu Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 10
<211> LENGTH: 227
<212> TYPE: PRT
<213> ORGANISM: Mus musculus

<400> SEQUENCE: 10

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Ile Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Gly Gly Pro Leu Asp Asp Ser Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225


<210> SEQ ID NO 11
<211> LENGTH: 215
<212> TYPE: PRT
<213> ORGANISM: Mus musculus

<400> SEQUENCE: 11

Leu Asp Ile Gln Leu Thr Gln Ser Pro Ser Thr Leu Ser Ala Ser Val
1               5                   10                  15

Gly Asp Arg Val Thr Ile Thr Cys Arg Ala Ser Gln Thr Ile Ser Ser
            20                  25                  30
```

```
Ser Leu Ala Trp Tyr Gln Gln Lys Pro Gly Lys Ala Pro Asn Leu Leu
        35                  40                  45

Ile Tyr Lys Ala Ser Thr Leu Glu Gly Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Ser Tyr Thr Thr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 12
<211> LENGTH: 227
<212> TYPE: PRT
<213> ORGANISM: Mus musculus

<400> SEQUENCE: 12

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Ile Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Gly Gly Pro Leu Asp Asp Ser Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
```

```
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225


<210> SEQ ID NO 13
<211> LENGTH: 215
<212> TYPE: PRT
<213> ORGANISM: Mus musculus

<400> SEQUENCE: 13

Leu Asp Ile Gln Leu Thr Gln Ser Pro Pro Ser Leu Ser Ala Ser Val
1               5                   10                  15

Gly Asp Arg Val Thr Ile Thr Cys Gln Ala Pro His Asp Ile Lys Asn
            20                  25                  30

Asn Leu Asn Trp Tyr Gln Gln Lys Pro Gly Lys Ala Pro Lys Leu Leu
        35                  40                  45

Ile Phe Asp Ala Ser Asn Leu Glu Thr Gly Val Pro Ser Arg Phe Ser
    50                  55                  60

Gly Ser Gly Ser Gly Thr Asn Phe Val Leu Thr Ile Ser Ser Leu Gln
65                  70                  75                  80

Pro Glu Asp Ile Ala Thr Tyr Tyr Cys Gln Gln Phe His Asp Leu Pro
                85                  90                  95

Leu Thr Phe Gly Gly Gly Thr Lys Val Asp Met Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 14
<211> LENGTH: 230
<212> TYPE: PRT
<213> ORGANISM: Mus musculus

<400> SEQUENCE: 14

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
```

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Glu Asp Tyr Asp Tyr Val Trp Gly Ser Tyr Arg Gln Tyr
            100                 105                 110

Pro Ser Arg Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys
225                 230


<210> SEQ ID NO 15
<211> LENGTH: 213
<212> TYPE: PRT
<213> ORGANISM: Mus musculus

<400> SEQUENCE: 15

Gln Ser Val Leu Thr Gln Pro Pro Ser Val Ser Val Ser Pro Gly Gln
1               5                   10                  15

Thr Ala Ser Ile Thr Cys Ser Gly Asp Asn Leu Gly Tyr Lys Tyr Ala
            20                  25                  30

Ser Trp Tyr Gln Gln Lys Pro Gly Gln Ser Pro Val Leu Ile Ile Tyr
        35                  40                  45

Gln Asp Lys Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ser Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190
```

```
Ser Cys Gln Val Thr His Glu Gly Ser Thr Val Glu Lys Thr Val Ala
        195                 200                 205

Pro Thr Glu Cys Ser
    210


<210> SEQ ID NO 16
<211> LENGTH: 227
<212> TYPE: PRT
<213> ORGANISM: Mus musculus

<400> SEQUENCE: 16

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Ile Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Gly Gly Pro Leu Asp Asp Ser Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225


<210> SEQ ID NO 17
<211> LENGTH: 220
<212> TYPE: PRT
<213> ORGANISM: Mus musculus

<400> SEQUENCE: 17

Leu Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu Arg
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Ile Arg Ala Ser Gly Val
    50                  55                  60
```

```
Pro Asp Arg Phe Ser Gly Ser Gly Ser Gly Thr Asp Phe Thr Leu Arg
65                  70                  75                  80

Ile Ser Arg Val Glu Ala Glu Asp Val Gly Val Tyr Tyr Cys Met Gln
                85                  90                  95

Ala Leu Gln Thr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 18
<211> LENGTH: 226
<212> TYPE: PRT
<213> ORGANISM: Mus musculus

<400> SEQUENCE: 18

Glu Val Gln Leu Val Asp Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Trp Gly Arg Asn Ile Ala Val Ala Gly Thr Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220
```

```
Ser Cys
225

<210> SEQ ID NO 19
<211> LENGTH: 215
<212> TYPE: PRT
<213> ORGANISM: Mus musculus

<400> SEQUENCE: 19

Leu Ser Tyr Glu Leu Thr Gln Pro Pro Ser Val Ser Val Ser Pro Gly
1               5                   10                  15

Gln Thr Ala Ser Ile Thr Cys Ser Gly Asp Lys Leu Gly Gln Lys Tyr
            20                  25                  30

Val Ser Trp Tyr Gln Gln Arg Pro Gly Gln Ser Pro Leu Leu Val Ile
        35                  40                  45

Phe Gln Asp Asp Lys Arg Pro Ser Gly Ile Pro Glu Arg Ile Ser Gly
    50                  55                  60

Ser Asn Ser Gly His Thr Ala Thr Leu Thr Ile Ser Ala Thr Gln Ala
65                  70                  75                  80

Met Asp Glu Ala Glu Tyr Phe Cys Gln Ala Trp Asp Ser Asn Thr Ala
                85                  90                  95

Pro Tyr Val Phe Gly Thr Gly Thr Gln Val Thr Val Leu Ser Gln Pro
            100                 105                 110

Lys Ala Asn Pro Thr Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Gly Ser Pro Val Lys Ala
145                 150                 155                 160

Gly Val Glu Thr Thr Lys Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 20
<211> LENGTH: 220
<212> TYPE: PRT
<213> ORGANISM: Mus musculus

<400> SEQUENCE: 20

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

```
Arg Gly Arg Arg Phe Gly Asp Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys
    210                 215                 220


<210> SEQ ID NO 21
<211> LENGTH: 214
<212> TYPE: PRT
<213> ORGANISM: Mus musculus

<400> SEQUENCE: 21

Gln Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Pro Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Ser Pro Phe Gly Thr Gly Thr Lys Val Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 22
<211> LENGTH: 227
<212> TYPE: PRT
```

<213> ORGANISM: Mus musculus

<400> SEQUENCE: 22

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Ile Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Gly Gly Pro Leu Asp Asp Ser Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225
```

<210> SEQ ID NO 23
<211> LENGTH: 215
<212> TYPE: PRT
<213> ORGANISM: Mus musculus

<400> SEQUENCE: 23

```
Leu Asp Ile Gln Leu Thr Gln Ser Pro Pro Ser Leu Ser Ala Ser Val
1               5                   10                  15

Gly Asp Arg Val Thr Ile Thr Cys Gln Ala Pro His Asp Ile Lys Asn
            20                  25                  30

Asn Leu Asn Trp Tyr Gln Gln Lys Pro Gly Lys Ala Pro Lys Leu Leu
        35                  40                  45

Ile Phe Asp Ala Ser Asn Leu Glu Thr Gly Val Pro Ser Arg Phe Ser
    50                  55                  60

Gly Ser Gly Ser Gly Thr Asn Phe Val Leu Thr Ile Ser Ser Leu Gln
65                  70                  75                  80

Pro Glu Asp Ile Ala Thr Tyr Tyr Cys Gln Gln Phe Asp Asp Leu Pro
                85                  90                  95

Leu Thr Phe Gly Gly Gly Thr Lys Val Asp Met Lys Arg Thr Val Ala
            100                 105                 110

Ala Pro Ser Val Phe Ile Phe Pro Pro Ser Asp Glu Gln Leu Lys Ser
```

```
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Glu Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 24
<211> LENGTH: 227
<212> TYPE: PRT
<213> ORGANISM: Mus musculus

<400> SEQUENCE: 24

Gln Val Gln Leu Gln Gln Ser Gly Pro Gly Leu Val Asn Pro Ser Gln
1               5                   10                  15

Thr Leu Ser Val Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Lys Pro Asp Thr Ser Lys Asn
65                  70                  75                  80

Gln Phe Ser Leu Gln Leu Asn Ser Val Thr Pro Asp Asp Thr Ala Val
                85                  90                  95

Tyr Tyr Cys Ala Arg Asp Pro Gly Gly Ser Leu Asp Asp Ser Phe Asp
            100                 105                 110

Ile Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225


<210> SEQ ID NO 25
<211> LENGTH: 215
<212> TYPE: PRT
<213> ORGANISM: Mus musculus
```

<400> SEQUENCE: 25

```
Leu Asp Ile Gln Met Thr Gln Ser Pro Pro Ser Leu Ser Ala Ser Val
1               5                   10                  15

Gly Asp Arg Val Thr Ile Thr Cys Gln Ala Pro His Asp Ile Lys Asn
            20                  25                  30

Asn Leu Asn Trp Tyr Gln Gln Lys Pro Gly Lys Ala Pro Lys Leu Leu
        35                  40                  45

Ile Phe Asp Ala Ser Asn Leu Glu Thr Gly Val Pro Ser Arg Phe Ser
    50                  55                  60

Gly Ser Gly Ser Gly Thr Asn Phe Val Leu Thr Ile Ser Ser Leu Gln
65                  70                  75                  80

Pro Glu Asp Ile Ala Thr Tyr Tyr Cys Gln Gln Phe Asp Asp Leu Pro
                85                  90                  95

Leu Thr Phe Gly Gly Gly Thr Lys Val Asp Met Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 26
<211> LENGTH: 227
<212> TYPE: PRT
<213> ORGANISM: Mus musculus

<400> SEQUENCE: 26

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Lys Pro Asp Thr Ser Lys Asn
65                  70                  75                  80

Gln Phe Ser Leu Gln Leu Asn Ser Val Thr Pro Asp Asp Thr Ala Val
                85                  90                  95

Tyr Tyr Cys Ala Arg Asp Pro Gly Gly Ser Leu Asp Asp Ser Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140
```

```
Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225


<210> SEQ ID NO 27
<211> LENGTH: 220
<212> TYPE: PRT
<213> ORGANISM: Mus musculus

<400> SEQUENCE: 27

Leu Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu Arg
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Thr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Phe Gln Thr Pro Leu Thr Phe Gly Gly Gly Thr Lys Met Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 28
<211> LENGTH: 227
<212> TYPE: PRT
<213> ORGANISM: Mus musculus

<400> SEQUENCE: 28

Gln Val Gln Leu Gln Gln Ser Gly Pro Gly Leu Val Lys Pro Ser Gln
1               5                   10                  15
```

```
Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Ile Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Gly Gly Pro Leu Asp Asp Ser Tyr Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225


<210> SEQ ID NO 29
<211> LENGTH: 220
<212> TYPE: PRT
<213> ORGANISM: Mus musculus

<400> SEQUENCE: 29

Leu Glu Ile Val Leu Thr Gln Ser Pro Leu Ser Leu Pro Val Thr Pro
1               5                   10                  15

Gly Glu Pro Ala Ser Ile Ser Cys Arg Ser Ser Gln Ser Leu Leu Arg
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Phe Gln Thr Pro Leu Thr Phe Gly Gly Gly Thr Lys Met Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

```
Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 30
<211> LENGTH: 225
<212> TYPE: PRT
<213> ORGANISM: Mus musculus

<400> SEQUENCE: 30

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ala Ser Gly Gly Ser Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Lys Glu Arg Pro Asp Tyr Asp Phe Trp Ser Ala Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225


<210> SEQ ID NO 31
<211> LENGTH: 220
<212> TYPE: PRT
<213> ORGANISM: Mus musculus

<400> SEQUENCE: 31

Leu Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30
```

```
Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Thr His Trp Pro Pro Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 32
<211> LENGTH: 321
<212> TYPE: PRT
<213> ORGANISM: Mus musculus

<400> SEQUENCE: 32

Leu Leu Ala Pro Ser Ser Lys Ser Thr Ser Gly Gly Thr Ala Ala Leu
1               5                   10                  15

Gly Cys Leu Val Lys Asp Tyr Phe Pro Glu Pro Val Thr Val Ser Trp
            20                  25                  30

Asn Ser Gly Ala Leu Thr Ser Gly Val His Thr Phe Pro Ala Val Leu
        35                  40                  45

Gln Ser Ser Gly Leu Tyr Ser Leu Ser Ser Val Val Thr Val Pro Ser
    50                  55                  60

Ser Ser Leu Gly Thr Gln Thr Tyr Ile Cys Asn Val Asn His Lys Pro
65                  70                  75                  80

Ser Asn Thr Lys Val Asp Lys Lys Val Glu Pro Lys Ser Cys Asp Lys
                85                  90                  95

Thr His Thr Cys Pro Pro Cys Pro Ala Pro Glu Leu Leu Gly Gly Pro
            100                 105                 110

Ser Val Phe Leu Phe Pro Pro Lys Pro Lys Asp Thr Leu Met Ile Ser
        115                 120                 125

Arg Thr Pro Glu Val Thr Cys Val Val Val Asp Val Ser His Glu Asp
    130                 135                 140

Pro Glu Val Lys Phe Asn Trp Tyr Val Asp Gly Val Glu Val His Asn
145                 150                 155                 160

Ala Lys Thr Lys Pro Arg Glu Glu Gln Tyr Asn Ser Thr Tyr Arg Val
                165                 170                 175

Val Ser Val Leu Thr Val Leu His Gln Asp Trp Leu Asn Gly Lys Glu
```

```
            180                 185                 190

Tyr Lys Cys Lys Val Ser Asn Lys Ala Leu Pro Ala Pro Ile Glu Lys
        195                 200                 205

Thr Ile Ser Lys Ala Lys Gly Gln Pro Arg Glu Pro Gln Val Tyr Thr
    210                 215                 220

Leu Pro Pro Ser Arg Asp Glu Leu Thr Lys Asn Gln Val Ser Leu Thr
225                 230                 235                 240

Cys Leu Val Lys Gly Phe Tyr Pro Ser Asp Ile Ala Val Glu Trp Glu
                245                 250                 255

Ser Asn Gly Gln Pro Glu Asn Asn Tyr Lys Thr Thr Pro Pro Val Leu
            260                 265                 270

Asp Ser Asp Gly Ser Phe Phe Leu Tyr Ser Lys Leu Thr Val Asp Lys
        275                 280                 285

Ser Arg Trp Gln Gln Gly Asn Val Phe Ser Cys Ser Val Met His Glu
    290                 295                 300

Ala Leu His Asn His Tyr Thr Gln Lys Ser Leu Ser Leu Ser Pro Gly
305                 310                 315                 320

Lys


<210> SEQ ID NO 33
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 33

Gly Gly Asn Asn Ile Gly Ser Lys Ser Val His
1               5                   10


<210> SEQ ID NO 34
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 34

Arg Ser Ser Gln Ser Leu Leu Arg Ser Asn Gly Tyr Asn Tyr Leu Asp
1               5                   10                  15


<210> SEQ ID NO 35
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 35

Asp Asp Ser Asp Arg Pro Pro
1               5


<210> SEQ ID NO 36
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 36

Leu Gly Ser Ile Arg Ala Ser
1               5
```

```
<210> SEQ ID NO 37
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 37

Gln Val Trp Asp Ser Ser Ser Asp His Ser Pro
1               5                   10


<210> SEQ ID NO 38
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 38

Met Gln Ala Leu Gln Thr Pro Phe Thr
1               5


<210> SEQ ID NO 39
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 39

Gly Gly Ser Phe Ser Gly Tyr Tyr Trp Ser Trp
1               5                   10


<210> SEQ ID NO 40
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 40

Gly Asp Ser Val Ser Ser Asn Ser Ala Ala Trp Asn
1               5                   10


<210> SEQ ID NO 41
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 41

Glu Ile Asn His Ser Gly Ser Thr Asn Tyr Asn Pro Ser Leu Lys Ser
1               5                   10                  15


<210> SEQ ID NO 42
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 42

Arg Thr Tyr Tyr Arg Ser Lys Trp Tyr Asn Asp Tyr Ala Val Ser Val
1               5                   10                  15
```

Lys Ser

<210> SEQ ID NO 43
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 43

Gly Arg Arg Phe Gly Asp Phe Asp Tyr
1               5

<210> SEQ ID NO 44
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 44

Asp Pro Gly Gly Pro Leu Asp Asp Ser Phe Asp Ile
1               5                   10

<210> SEQ ID NO 45
<211> LENGTH: 684
<212> TYPE: DNA
<213> ORGANISM: Mus musculus

<400> SEQUENCE: 45
gcccaggtac agctgcagca gtcaggtcca ggactggtga agccctcgca gaccctctca 60
ctcacctgtg ccatctccgg ggacagtgtc tctagcaaca gtgctgcttg gaactggatc 120
aggcagtccc catcgagagg ccttgagtgg ctgggaagga catactacag gtccaagtgg 180
tataatgatt atgcagtatc tgtgaaaagt cgaataacca tcaacccaga cacatccaag 240
aaccagttct ccctgcagct gaactctgtg actcccgagg acacggctgt gtattactgt 300
acaagagatc cgggggggc tctcgatgat agttttgata tctggggcca agggacaatg 360
gtcaccgtct caagcgcctc caccaagggc ccatcggtct tccccctggc accctcctcc 420
aagagcacct ctgggggcac agcggccctg ggctgcctgg tcaaggacta cttccccgaa 480
ccggtgacgg tgtcgtggaa ctcaggcgcc ctgaccagcg gcgtccacac cttcccggct 540
gtcctacagt cctcaggact ctactccctc agcagcgtag tgaccgtgcc ctccagcagc 600
ttgggcaccc agacctacat ctgcaacgtg aatcacaagc ccagcaacac caaggtggac 660
aagaaagttg agcccaaatc ttgt 684

<210> SEQ ID NO 46
<211> LENGTH: 645
<212> TYPE: DNA
<213> ORGANISM: Mus musculus

<400> SEQUENCE: 46
cttgatgttg tgatgactca gtctccagcc tccctgtctg tatctgtagg agacagagtc 60
accctcactt gccaggcgag tcaggtcatt aacaaccact taaattggta tcaacaacaa 120
ccagggaaag cccctaagct cctggtctac gatgcatcca atctggaaac aggggtccca 180
tcaaggttca gtggaagtgg atctgggaca gattttactt tcaccatcag cggcctgcag 240
cctgaagata ttgcaacata ttactgtcaa cagtctgata atctcccgct cactttcggc 300
ggagggacca agctagagat caaacgaact gtggctgcac catctgtctt catcttcccg 360

```
ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgt                    645


<210> SEQ ID NO 47
<211> LENGTH: 681
<212> TYPE: DNA
<213> ORGANISM: Mus musculus

<400> SEQUENCE: 47

caggtacagc tgcagcagtc aggtccagga ctggtgaagc cctcgcagac cctctcactc     60

acctgcgcca tctccgggga cagtgtctct agcaacagtg ctgcttggaa ctggatcagg    120

cagtccccat cgagaggcct tgagtggctg ggaaggacat attacaggtc caagtggtat    180

aatgattatg cagaatctgt gaaaagtcga atagtcatca acgtagacac atccaagaac    240

cagttctccc tgcagttgaa ctctgtgact cccgaggaca cggctgtgta ttactgtgca    300

agagatccgg gggggcctct cgatgatagt tttgatatct ggggccaagg gacaatggtc    360

accgtctcaa gcgcctccac caagggccca tcggtcttcc ccctggcacc ctcctccaag    420

agcacctctg gggcacagc ggccctgggc tgcctggtca aggactactt ccccgaaccg    480

gtgacggtgt cgtggaactc aggcgccctg accagcggcg tccacacctt cccggctgtc    540

ctacagtcct caggactcta ctccctcagc agcgtagtga ccgtgccctc cagcagcttg    600

ggcacccaga cctacatctg caacgtgaat cacaagccca gcaacaccaa ggtggacaag    660

aaagttgagc ccaaatcttg t                                              681


<210> SEQ ID NO 48
<211> LENGTH: 660
<212> TYPE: DNA
<213> ORGANISM: Mus musculus

<400> SEQUENCE: 48

cttgaaattg tgatgacaca gtctccagtc tccctgcccg tcacccctgg agagccggcc     60

tccatctcct gcaggtctag tcagagcctc ctgcgtaata atggatacaa ctatttggat    120

tggtacctgc agaagccagg gcagtctcca cagctcctga tctatttggg ttctaatcgg    180

gcctccgggg tccctgacag gttcagtggc agtggatcag gcacagattt tacactgaaa    240

atcagcagag tggaggctga ggatgttggg gtttattact gcatgcaagc tctacaaact    300

ccattcactt tcggccctgg gaccaaagtg gatatcaaac gaactgtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

cagtcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660


<210> SEQ ID NO 49
<211> LENGTH: 681
<212> TYPE: DNA
<213> ORGANISM: Mus musculus
```

<400> SEQUENCE: 49

```
caggtacagc tgcagcagtc aggtccagga ctggtgaagc cctcgcagac cctctcactc     60

acctgtgcca tctccgggga cagtgtctct agcaacagtg ctgcttggaa ctggatcagg    120

cagtccccat cgagaggcct tgagtggctg ggaaggacat actacaggtc caagtggtat    180

aatgattatg cagtatccgt gaaaagtcga ataattatca acccagacac atccaagaac    240

cagttctccc tgcagctgaa ctctgtgact cccgaggaca cggctgtgta ttactgtgca    300

agagatccgg gggggcctct cgatgatagt tttgatatct ggggccaagg gacaatggtc    360

accgtctcaa gcgcctccac caagggccca tcggtcttcc ccctggcacc ctcctccaag    420

agcacctctg gggggcacagc ggccctgggc tgcctggtca aggactactt ccccgaaccg    480

gtgacggtgt cgtggaactc aggcgccctg accagcggcg tccacacctt cccggctgtc    540

ctacagtcct caggactcta ctccctcagc agcgtagtga ccgtgccctc cagcagcttg    600

ggcacccaga cctacatctg ctacgtgaat cacaagccca gcaacaccaa ggtggacaag    660

aaagttgagc ccaaatcttg t                                              681
```

<210> SEQ ID NO 50
<211> LENGTH: 660
<212> TYPE: DNA
<213> ORGANISM: Mus musculus

<400> SEQUENCE: 50

```
cttgatgttg tgatgactca gtctccactc tccctgcccg tcacccctgg agagccggcc     60

tccatctcct gcaggtctag tcagagcctc ctgcgtagta atggatacaa ctatttggat    120

tggtacctgc agaagccagg gcagtctcca cagctcctga tctatttggg ttctattcgg    180

gcctccgggg tccctgacag gttcagtggc agtggatcgg gcacagattt tacactgaga    240

attagcagag tggaggctga ggatgttggg gtttattact gcatgcaagc tctacaaacc    300

ccgttcactt ttggccaggg gaccaagctg gagatcaagc gaactgtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 51
<211> LENGTH: 684
<212> TYPE: DNA
<213> ORGANISM: Mus musculus

<400> SEQUENCE: 51

```
caggtgcagc tgcaggagtc cggcccagga ctggtgaagc cttcggagac cctgtccctc     60

acctgcactg tctctggtgg ctccatcagc agtagtagtt actactgggg ctggatccgc    120

cagcccccag ggaaggggct ggagtggatt gggagtatct attatagtgg gagcacctac    180

tacaacccgt ccctcaagag tcgagtcacc atatccgtag acacgtccaa gaaccagttc    240

tccctgaagc tgacctctgt gaccgccgca gacacggctg tgtattactg tgcgagacta    300

aacgcccacc cgatttacta ctactactac ggtatggacg tctggggcca agggaccacg    360

gtcaccgtct caagcgcctc caccaagggc ccatcggtct tcccccctggc accctcctcc    420

aagagcacct ctgggggcac agcggccctg ggctgcctgg tcaaggacta cttccccgaa    480
```

```
ccggtgacgg tgtcgtggaa ctcaggcgcc ctgaccagcg gcgtccacac cttcccggct    540

gtcctacagt cctcaggact ctactccctc agcagcgtag tgaccgtgcc ctccagcagc    600

ttgggcaccc agacctacat ctgcaacgtg aatcacaagc ccagcaacac caaggtggac    660

aagaaagttg agcccaaatc ttgt                                           684
```

<210> SEQ ID NO 52
<211> LENGTH: 651
<212> TYPE: DNA
<213> ORGANISM: Mus musculus

<400> SEQUENCE: 52

```
cttgaaattg tgctgactca gtctccaggc accctgtctt tgtctccagg ggaaagagcc     60

accctctcct gcagggccag tcagagtgtt agcagctact tagcctggta ccaacagaaa    120

cctggccagg ctcccaggct cctcatctat gatgcatcca acagggccac tggcatccca    180

gccaggttca gtggcagtgg gtctgggaca gacttcactc tcaccatcag cagcctagag    240

cctgaagatt ttgcagttta ttactgtcag cagcgtagca actggcctcc gatgtacact    300

tttggccagg ggaccaagct ggagatcaaa cgaactgtgg ctgcaccatc tgtcttcatc    360

ttcccgccat ctgatgagca gttgaaatct ggaactgcct ctgttgtgtg cctgctgaat    420

aacttctatc ccagagaggc caaagtacag tggaaggtgg ataacgccct ccaatcgggt    480

aactcccagg agagtgtcac agagcaggac agcaaggaca gcacctacag cctcagcagc    540

accctgacgc tgagcaaagc agactacgag aaacacaaag tctacgcctg cgaagtcacc    600

catcagggcc tgagctcgcc cgtcacaaag agcttcaaca ggggagagtg t             651
```

<210> SEQ ID NO 53
<211> LENGTH: 681
<212> TYPE: DNA
<213> ORGANISM: Mus musculus

<400> SEQUENCE: 53

```
caggtacagc tgcagcagtc aggtccagga ctggtgaagc cctcgcagac cctctcactc     60

acctgtgcca tctccgggga cagtgtctct agtaacagtg ctgcttggaa ctggatcagg    120

cagtccccat cgagaggcct tgagtggctg ggaggacat actacaggtc caagtggtat     180

tatgattatg cagtctctgt gaaaggtcga ataaccttca ccccagacac atccaagaac    240

caggtctccc tgcacctgaa cgctgtgact cccgaggaca cggctatgta ttactgtgca    300

agagatccgg gggggcctct cgatgatagt tttgatatct ggggccaagg gacaatggtc    360

accgtctcaa gcgcctccac caagggccca tcggtcttcc ccctggcacc ctcctccaag    420

agcacctctg gggcacagc ggccctgggc tgcctggtca aggactactt ccccgaaccg     480

gtgacggtgt cgtggaactc aggcgccctg accagcggcg tccacacctt cccggctgtc    540

ctacagtcct caggactcta ctccctcagc agcgtagtga ccgtgccctc cagcagcttg    600

ggcacccaga cctacatctg caacgtgaat cacaagccca gcaacaccaa ggtggacaag    660

aaagttgagc ccaaatcttg t                                              681
```

<210> SEQ ID NO 54
<211> LENGTH: 645
<212> TYPE: DNA
<213> ORGANISM: Mus musculus

<400> SEQUENCE: 54

```
cttgacatcc agttgaccca gtctccaccc tccctgtctg catctgtagg agacagagtc     60

actatcactt gccaggcgcc tcacgacatt aagaacaatt taaattggta tcaacagaaa    120

ccagggaaag cccctaaact cctgatcttc gacgcatcta atttggagac gggagtccca    180

tcaagattca gtggaagtgg atctgggaca aattttgtgc tcaccatcag cagcctgcag    240

cctgaagata ttgcaactta ttactgtcaa cagtttcatg atctcccgct cactttcggc    300

ggagggacca aggtagacat gaaacgaact gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgt                    645
```

<210> SEQ ID NO 55
<211> LENGTH: 684
<212> TYPE: DNA
<213> ORGANISM: Mus musculus

<400> SEQUENCE: 55

```
cagctgcagc tgcaggagtc gggggaggc gtggtccagc ctgggaggtc cctgagactc     60

tcctgtgcag cctctggatt caccttcagt agctatgcta tgcactgggt ccgccaggct    120

ccaggcaagg ggctggagtg ggtggcagtt atatcatatg atggaagcaa taaatactac    180

gcagactccg tgaagggccg attcaccatc tccagagaca attccaagaa cacgctgtat    240

ctgcaaatga acagcctgag agctgaggac acggctgtgt attactgtgc gagaccctat    300

agcagcagct ggtacagcgt tgggaactac ggtatagacg tctggggcca agggaccacg    360

gtcaccgtct caagcgcctc caccaagggc ccatcggtct tccccctggc accctcctcc    420

aagagcacct ctgggggcac agcggccctg ggctgcctgg tcaaggacta cttccccgaa    480

ccggtgacgg tgtcgtggaa ctcaggcgcc ctgaccagcg gcgtccacac cttcccggct    540

gtcctacagt cctcaggact ctactccctc agcagcgtag tgaccgtgcc ctccagcagc    600

ttgggcaccc agacctacat ctgcaacgtg aatcacaagc ccagcaacac caaggtggac    660

aagaaagttg agcccaaatc ttgt                                           684
```

<210> SEQ ID NO 56
<211> LENGTH: 663
<212> TYPE: DNA
<213> ORGANISM: Mus musculus

<400> SEQUENCE: 56

```
caggctgtgc tgactcagcc gtcttccctc tctgcatctc ctggagcatc agccagtctc     60

acctgcacct tacgcagaga cattgatatt ggaaccgcca ggatttactg gtaccaacag    120

aagccaggga gcccccccca gtatctcctg aactacaaat cagacttgta cacggagaag    180

gcctctggag tccccagccg cttctctgga tccaaggatg cttcggccaa tgcaggcatt    240

ttgctcatct ctgggctcca gtctgaggat gaggctgact attactgtct gatttggcac    300

aacaatgctt gggtgttcgg cggagggacc aagctgaccg tcctaggtca gcccaaggct    360

gccccctcgg tcactctgtt cccgccctcc tctgaggagc ttcaagccaa caaggccaca    420

ctggtgtgtc tcataagtga cttctacccg ggagccgtga cagtggcctg gaaggcagat    480

ggcagccccg tcaaggcggg agtggagacc accaaaccct ccaaacagag caacaacaag    540
```

```
tacgcggcca gcagctacct gagcctgacg cccgagcagt ggaagtccca cagaagctac    600

agctgccagg tcacgcatga agggagcacc gtggagaaga cagtggcccc tacagaatgt    660

tca                                                                  663
```

<210> SEQ ID NO 57
<211> LENGTH: 681
<212> TYPE: DNA
<213> ORGANISM: Mus musculus

<400> SEQUENCE: 57

```
caggtacagc tgcagcagtc aggtccagga ctggtgaagc cctcgcagac cctctcactc     60

acctgcgcca tctccgggga cagtgtctct agcaacagtg ctgcttggaa ctggatcagg    120

cagtccccat cgagaggcct tgagtggctg ggaaggacat attacaggtc caagtggtat    180

aatgattatg cagaatctgt gaaaagtcga atagtcatca acgtagacac atccaagaac    240

cagttctccc tgcagttgaa ctctgtgact cccgaggaca cggctgcgta ttactgtgca    300

agagatccgg gggggcctct cgatgatagt tttgatatct ggggccaagg gacaatggtc    360

accgtctcaa gcgcctccac caagggccca tcggtcttcc ccctggcacc ctcctccaag    420

agcacctctg ggggcacagc ggccctgggc tgcctggtca aggactactt ccccgaaccg    480

gtgacggtgt cgtggaactc aggcgccctg accagcggcg tccacacctt cccggctgtc    540

ctacagtcct caggactcta ctccctcagc agcgtagtga ccgtgccctc cagcagcttg    600

ggcacccaga cctacatctg caacgtgaat cacaagccca gcaacaccaa ggtggacaag    660

aaagttgagc ccaaatcttg t                                              681
```

<210> SEQ ID NO 58
<211> LENGTH: 651
<212> TYPE: DNA
<213> ORGANISM: Mus musculus

<400> SEQUENCE: 58

```
cagtctgtcg tgacgcagcc gccctcagtg tctggggcgc caggtcagag ggtcatcatc     60

tcctgcactg ggagcagctc caacatcggg gcaggctttg atgtacactg gtatcagcag    120

cttccaggaa cagtccccaa actcctcatc tatggtaaca caaatcggcc ctcaggggtc    180

cctgaccgat tctctggctc caaggctggc acctcagcct ccctggccat cactgggctc    240

caggctgagg atgaggctga ttattactgc caggcttatg acgactccct gcaaggttat    300

gtcttcggca cagggaccaa gttaaccgtc gtcggtcagc ccaaggccaa ccccactgtc    360

actctgttcc cgccctcctc tgaggagctc caagccaaca aggccacact agtgtgtctg    420

atcagtgact tctacccggg agctgtgaca gtggcctgga aggcagatgg cagccccgtc    480

aaggcgggag tggagaccac caaaccctcc aaacagagca acaacaagta cgcggccagc    540

agctacctga gcctgacgcc cgagcagtgg aagtcccaca gaagctacag ctgccaggtc    600

acgcatgaag ggagcaccgt ggagaagaca gtggccccta cagaatgttc a             651
```

<210> SEQ ID NO 59
<211> LENGTH: 681
<212> TYPE: DNA
<213> ORGANISM: Mus musculus

<400> SEQUENCE: 59

```
caggtacagc tgcagcagtc aggtccagga ctggtgaagc cctcgcagac cctctcactc     60
```

```
acctgtgcca tctccgggga cagtgtctct agcaagagtg ctgcttggaa ctggatcagg    120

cagtccccat cgagaggcct tgagtggctg ggaaggacat actacaggtc caagtggtat    180

aatgattatg cagtatctgt gaaaagccga ataaccatca acccagacac atccaagaac    240

cagttctccc tgcagctgaa ctctgtgact cccgaggaca cggctgtgta ttactgtgca    300

agagatccgg gggggcctct cgatgatagt tttgatatct ggggccaagg gacaatggtc    360

accgtctcaa gcgcctccac caagggccca tcggtcttcc ccctggcacc ctcctccaag    420

agcacctctg ggggcacagc ggccctgggc tgcctggtca aggactactt ccccgaaccg    480

gtgacggtgt cgtggaactc aggcgccctg accagcggcg tccacacctt cccggctgtc    540

ctacagtcct caggactcta ctccctcagc agcgtagtga ccgtgccctc cagcagcttg    600

ggcacccaga cctacatctg ctacgtgaat cacaagccca gcaacaccaa ggtggacaag    660

aaagttgagc ccaaatcttg t                                               681
```

<210> SEQ ID NO 60
<211> LENGTH: 660
<212> TYPE: DNA
<213> ORGANISM: Mus musculus

<400> SEQUENCE: 60

```
cttgatgttg tgatgactca gtctccactc tccctgcccg tcacccctgg agagccggcc     60

tccatctcct gcaggtctag tcagagcctc ctgcgtagta atggatacaa ctatttagat    120

tggtacctgc agaagccagg gcagtctcca cagctcctga tctatttggg ttctactcgg    180

gcctccgggg tccctgacag gttcagtggc agtggatcgg gcacagattt tacactgaaa    240

atcagcagag tggaggctga ggatgttggg gtttattact gcatgcaagc ttttcaaact    300

ccgctcactt tcggcggagg gaccaagatg gagatcaaac gaactgtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 61
<211> LENGTH: 678
<212> TYPE: DNA
<213> ORGANISM: Mus musculus

<400> SEQUENCE: 61

```
caggtacagc tgcagcagtc aggtccagga ctggtgaagc cctcgcagac cctctcactc     60

acctgtgcca tctccgggga cagtgtctct agcaacagtg ctgcttggaa ctggatcagg    120

cagtccccat cgagaggcct tgagtggctg ggaaggacat actacaggtc caagtggtat    180

aatgattatg cagtatctgt gaaaagtcga ataaccatca acccagacac atccaagaac    240

cagttctccc tgcagctgaa ctctgtgact cccgaggaca cggctgtgta ttactgtgca    300

agagattcgg gactggggtc agactacttt gactactggg gccagggcac cctggtcacc    360

gtctcaagcg cctccaccaa gggcccatcg gtcttccccc tggcaccctc ctccaagagc    420

acctctgggg gcacagcggc cctgggctgc ctggtcaagg actacttccc cgaaccggtg    480

acggtgtcgt ggaactcagg cgccctgacc agcggcgtcc acaccttccc ggctgtccta    540

cagtcctcag gactctactc cctcagcagc gtagtgaccg tgccctccag cagcttgggc    600
```

```
acccagacct acatctgcaa cgtgaatcac aagcccagca acaccaaggt ggacaagaaa    660

gttgagccca aatcttgt                                                  678


<210> SEQ ID NO 62
<211> LENGTH: 645
<212> TYPE: DNA
<213> ORGANISM: Mus musculus

<400> SEQUENCE: 62

cttgacatcc agatgaccca gtctccaccc tccctgtctg catctgtagg agacagagtc     60

actatcactt gccaggcgcc tcacgacatt aagaacaatt taaattggta tcaacagaaa    120

ccagggaaag cccctaaact cctgatcttc gacgcatcta atttggagac gggagtccca    180

tcaagattca gtggaagtgg atctgggaca aattttgtgc tcaccatcag cagcctgcag    240

cctgaagata ttgcaactta ttactgtcaa cagtttgatg atctcccgct cactttcggc    300

ggagggacca aggtagacat gaaacgaact gtggctgcac catctgtctt catcttcccg    360

ccatctgatg agcagttgga atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgt                    645


<210> SEQ ID NO 63
<211> LENGTH: 681
<212> TYPE: DNA
<213> ORGANISM: Mus musculus

<400> SEQUENCE: 63

caggtacagc tgcagcagtc aggtccagga ctggtgaagc cctcgcagac cctctcactc     60

acctgtgcca tctccgggga cagtgtctct agcaacagtg ctgcttggaa ctggatcagg    120

cagtccccat cgagaggcct tgagtggctg ggaaggacat actacaggtc caagtggtat    180

aatgattatg cagtatccgt gaaaagtcga ataattatca acccagacac atccaagaac    240

cagttctccc tgcagctgaa ctctgtgact cccgaggaca cggctgtgta ttactgtgca    300

agagatccgg gggggcctct cgatgatagt tttgatatct ggggccaagg gacaatggtc    360

accgtctcaa gcgcctccac caagggccca tcggtcttcc ccctggcacc ctcctccaag    420

agcacctctg ggggcacagc ggccctgggc tgcctggtca aggactactt ccccgaaccg    480

gtgacggtgt cgtggaactc aggcgccctg accagcggcg tccacacctt cccggctgtc    540

ctacagtcct caggactcta ctccctcagc agcgtagtga ccgtgccctc cagcagcttg    600

ggcacccaga cctacatctg caacgtgaat cacaagccca gcaacaccaa ggtggacaag    660

aaagttgagc ccaaatcttg t                                              681


<210> SEQ ID NO 64
<211> LENGTH: 645
<212> TYPE: DNA
<213> ORGANISM: Mus musculus

<400> SEQUENCE: 64

cttgacatcc agttgaccca gtctccttcc accctgtctg catctgtagg ggacagagtc     60

accattactt gccgggccag tcagactata agtagttcgt tggcctggta tcagcagaaa    120
```

```
ccagggaaag cccctaacct cctgatctat aaggcgtcta cattagaagg tggggtcccc    180

tcgcgtttca gcggcagtgg atctgggaca gaattcactc tcaccatcag cagcctgcag    240

cctgaagatt ttgcaactta ctactgtcaa cagagttaca ctaccccgct cactttcggc    300

ggagggacca aggtggagat caaacgaact gtggctgcac catctgtctt catcttcccg    360

ccatctgatg agcagttgaa atctggaact gcctctgttg tgtgcctgct gaataacttc    420

taccccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgt                    645
```

<210> SEQ ID NO 65
<211> LENGTH: 681
<212> TYPE: DNA
<213> ORGANISM: Mus musculus

<400> SEQUENCE: 65

```
caggtacagc tgcagcagtc aggtccagga ctggtgaagc cctcgcagac cctctcactc     60

acctgtgcca tctccgggga cagtgtctct agtaacagtg ctgcttggaa ctggatcagg    120

cagtccccat cgagaggcct tgagtggctg ggaggacat actacaggtc caagtggtat    180

tatgattatg cagtctctgt gaaaggtcga ataaccttca ccccagacac atccaagaac    240

caggtctccc tgcacctgaa cgctgtgact cccgaggaca cggctatgta ttactgtgca    300

agagatccgg gggggcctct cgatgatagt tttgatatct ggggccaagg gacaatggtc    360

accgtctcaa gcgcctccac caagggccca tcggtcttcc ccctggcacc ctcctccaag    420

agcacctctg ggggcacagc ggccctgggc tgcctggtca aggactactt ccccgaaccg    480

gtgacggtgt cgtggaactc aggcgccctg accagcggcg tccacacctt cccggctgtc    540

ctacagtcct caggactcta ctccctcagc agcgtagtga ccgtgccctc cagcagcttg    600

ggcacccaga cctacatctg caacgtgaat cacaagccca gcaacaccaa ggtggacaag    660

aaagttgagc ccaaatcttg t                                               681
```

<210> SEQ ID NO 66
<211> LENGTH: 645
<212> TYPE: DNA
<213> ORGANISM: Mus musculus

<400> SEQUENCE: 66

```
cttgacatcc agttgaccca gtctccaccc tccctgtctg catctgtagg agacagagtc     60

actatcactt gccaggcgcc tcacgacatt aagaacaatt taaattggta tcaacagaaa    120

ccagggaaag cccctaaact cctgatcttc gacgcatcta atttggagac gggagtccca    180

tcaagattca gtggaagtgg atctgggaca aattttgtgc tcaccatcag cagcctgcag    240

cctgaagata ttgcaactta ttactgtcaa cagtttcatg atctcccgct cactttcggc    300

ggagggacca aggtagacat gaaacgaact gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgt                    645
```

<210> SEQ ID NO 67
<211> LENGTH: 690
<212> TYPE: DNA
<213> ORGANISM: Mus musculus

<400> SEQUENCE: 67
caggtgcagc tgcaggagtc gggggaggc ttggtacagc ctggggggtc cctgagactc 60
tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggccgtat attactgtgc gaaagatgag 300
gattatgatt acgtttgggg gagttatcga caatacccca gtcgctactg gggccaggga 360
accctggtca ccgtctcaag cgcctccacc aagggcccat cggtcttccc cctggcaccc 420
tcctccaaga gcacctctgg gggcacagcg gccctgggct gcctggtcaa ggactacttc 480
cccgaaccgg tgacggtgtc gtggaactca ggcgccctga ccagcggcgt ccacaccttc 540
ccggctgtcc tacagtcctc aggactctac tccctcagca gcgtagtgac cgtgccctcc 600
agcagcttgg gcacccagac ctacatctgc aacgtgaatc acaagcccag caacaccaag 660
gtggacaaga aagttgagcc caaatcttgt 690

<210> SEQ ID NO 68
<211> LENGTH: 639
<212> TYPE: DNA
<213> ORGANISM: Mus musculus

<400> SEQUENCE: 68
cagtctgtgc tgactcagcc accctcagtg tccgtgtccc caggacagac agccagcatc 60
acctgctctg gagataattt ggggtataaa tatgcttcct ggtatcagca gaagccaggc 120
cagtcccctg tgctgatcat ctatcaagat aagaagcggc cctctgggat ccctgagcga 180
ttctctggct ccaactctgg gaacacagcc actctgacca tcagcgggac ccaggctatg 240
gatgaggctg actattactg tcaggcgtgg gacagcagca cttctgtggt attcggcgga 300
gggaccaagc tgaccgtcct aggtcagccc aaggctgccc cctcggtcac tctgttccca 360
ccctcctctg aggagcttca agccaacaag gccacactgg tgtgtctcat aagtgacttc 420
tacccgggag ccgtgacagt ggcctggaag gcagatagca gccccgtcaa ggcgggagtg 480
gagaccacca caccctccaa acaaagcaac aacaagtacg cggccagcag ctatctgagc 540
ctgacgcctg agcagtggaa gtcccacaga agctacagct gccaggtcac gcatgaaggg 600
agcaccgtgg agaagacagt ggcccctaca gaatgttca 639

<210> SEQ ID NO 69
<211> LENGTH: 681
<212> TYPE: DNA
<213> ORGANISM: Mus musculus

<400> SEQUENCE: 69
caggtacagc tgcagcagtc aggtccagga ctggtgaagc cctcgcagac cctctcactc 60
acctgtgcca tctccgggga cagtgtctct agcaacagtg ctgcttggaa ctggatcagg 120
cagtccccat cgagaggcct tgagtggctg ggaaggacat actacaggtc caagtggtat 180
aatgattatg cagtatccgt gaaaagtcga ataattatca acccagacac atccaagaac 240

```
cagttctccc tgcagctgaa ctctgtgact cccgaggaca cggctgtgta ttactgtgca    300

agagatccgg gggggcctct cgatgatagt tttgatatct ggggccaagg gacaatggtc    360

accgtctcaa gcgcctccac caagggccca tcggtcttcc ccctggcacc ctcctccaag    420

agcacctctg ggggcacagc ggccctgggc tgcctggtca aggactactt ccccgaaccg    480

gtgacggtgt cgtggaactc aggcgccctg accagcggcg tccacacctt cccggctgtc    540

ctacagtcct caggactcta ctccctcagc agcgtagtga ccgtgccctc cagcagcttg    600

ggcacccaga cctacatctg caacgtgaat cacaagccca gcaacaccaa ggtggacaag    660

aaagttgagc ccaaatcttg t                                              681
```

<210> SEQ ID NO 70
<211> LENGTH: 660
<212> TYPE: DNA
<213> ORGANISM: Mus musculus

<400> SEQUENCE: 70

```
cttgatgttg tgatgactca gtctccactc tccctgcccg tcacccctgg agagccggcc     60

tccatctcct gcaggtctag tcagagcctc ctgcgtagta atggatacaa ctatttggat    120

tggtacctgc agaagccagg gcagtctcca cagctcctga tctatttggg ttctattcgg    180

gcctccgggg tccctgacag gttcagtggc agtggatcgg gcacagattt tacactgaga    240

attagcagag tggaggctga ggatgttggg gtttattact gcatgcaagc tctacaaacc    300

ccgttcactt ttggccaggg gaccaagctg gagatcaagc gaactgtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 71
<211> LENGTH: 678
<212> TYPE: DNA
<213> ORGANISM: Mus musculus

<400> SEQUENCE: 71

```
gaggtgcagc tggtggacac tgggggaggc ttggtacagc ctgggggggtc cctgagactc     60

tcctgtgcag cctctggatt cacctttagc agctatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaggac acggccgtat attattgtgc gaaagattgg    300

ggaagaaata tagcagtggc tggtaccctt gactactggg gccagggcac cctggtcacc    360

gtctcaagcg cctccaccaa gggcccatcg gtcttccccc tggcaccctc ctccaagagc    420

acctctgggg gcacagcggc cctgggctgc ctggtcaagg actacttccc cgaaccggtg    480

acggtgtcgt ggaactcagg cgccctgacc agcggcgtcc acaccttccc ggctgtccta    540

cagtcctcag gactctactc cctcagcagc gtagtgaccg tgccctccag cagcttgggc    600

acccagacct acatctgcaa cgtgaatcac aagcccagca acaccaaggt ggacaagaaa    660

gttgagccca aatcttgt                                                  678
```

<210> SEQ ID NO 72
<211> LENGTH: 645
<212> TYPE: DNA
<213> ORGANISM: Mus musculus

<400> SEQUENCE: 72

```
ctttcctatg agctgactca gccaccctca gtgtcggtgt ccccaggaca gacagccagc     60

attacctgct ctggagataa attgggacaa aagtatgttt catggtatca gcagaggcca    120

ggccagtctc ctctactggt catctttcaa gatgacaagc ggccctcagg gatccctgag    180

cgaatctctg gctccaactc tgggcacaca gccactctga ccatcagcgc gacccaggct    240

atggatgagg ctgagtattt ctgtcaggcg tgggacagta acactgcccc ttatgtcttc    300

ggaactggga cccaggtcac cgtcctaagt cagcccaagg ccaaccccac tgtcactctg    360

ttcccgccct cctctgagga gctccaagcc aacaaggcca cactagtgtg tctgatcagt    420

gacttctacc cgggagctgt gacagtggcc tggaaggcag atggcagccc cgtcaaggcg    480

ggagtggaga ccaccaaacc ctccaaacag agcaacaaca agtacgcggc cagcagctac    540

ctgagcctga cgcccgagca gtggaagtcc cacagaagct acagctgcca ggtcacgcat    600

gaagggagca ccgtggagaa gacagtggcc cctacagaat gctct                    645
```

<210> SEQ ID NO 73
<211> LENGTH: 660
<212> TYPE: DNA
<213> ORGANISM: Mus musculus

<400> SEQUENCE: 73

```
caggtgcagc tacagcagtg gggcgcagga ctgttgaagc cttcggagac cctgtccctc     60

acctgcgctg tctatggtgg gtccttcagt ggttactact ggagctggat ccgccagccc    120

ccagggaagg ggctggagtg gattggggaa atcaatcata gtggaagcac caactacaac    180

ccgtccctca agagtcgagt caccatatca gtagacacgt ccaagaacca gttctccctg    240

aagctgagct ctgtgaccgc cgcggacacg gctgtgtatt actgtgcgag aggcagaagg    300

ttcggggatt ttgactactg gggccaggga accctggtca ccgtctcaag cgcctccacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt ccacaccttc ccggctgtcc tacagtcctc aggactctac    540

tccctcagca gcgtagtgac cgtgccctcc agcagcttgg gcacccagac ctacatctgc    600

aacgtgaatc acaagcccag caacaccaag gtggacaaga aagttgagcc caaatcttgt    660
```

<210> SEQ ID NO 74
<211> LENGTH: 642
<212> TYPE: DNA
<213> ORGANISM: Mus musculus

<400> SEQUENCE: 74

```
cagcctgtgc tgactcagcc cccctcggtg tcagtggccc caggaaagac ggccaggatt     60

acctgtgggg gaaacaacat tggaagtaaa agtgtgcact ggtaccagca gaagccaggc    120

caggcccctg tgctggtcgt ctatgatgat agcgaccggc ccccagggat ccctgagcga    180

ttctctggct ccaattctgg gaacacggcc accctgacca tcagcagggt cgaagccggg    240

gatgaggccg actattactg tcaggtgtgg gatagtagta gtgatcactc cccccttcgga    300

actgggacca aggtcaccgt cctaggtcag cccaaggcca accccactgt cactctgttc    360
```

```
ccgccctcct ctgaggagct ccaagccaac aaggccacac tagtgtgtct gatcagtgac    420

ttctacccgg gagctgtgac agtggcctgg aaggcagatg gcagccccgt caaggcggga    480

gtggagacca ccaaaccctc caaacagagc aacaacaagt acgcggccag cagctacctg    540

agcctgacgc ccgagcagtg gaagtcccac agaagctaca gctgccaggt cacgcatgaa    600

gggagcaccg tggagaagac agtggcccct acagaatgct ct                       642
```

<210> SEQ ID NO 75
<211> LENGTH: 681
<212> TYPE: DNA
<213> ORGANISM: Mus musculus

<400> SEQUENCE: 75

```
caggtacagc tgcagcagtc aggtccagga ctggtgaagc cctcgcagac cctctcactc     60

acctgtgcca tctccgggga cagtgtctct agcaacagtg ctgcttggaa ctggatcagg    120

cagtccccat cgagaggcct tgagtggctg ggaaggacat actacaggtc caagtggtat    180

aatgattatg cagtatccgt gaaaagtcga ataattatca acccagacac atccaagaac    240

cagttctccc tgcagctgaa ctctgtgact cccgaggaca cggctgtgta ttactgtgca    300

agagatccgg gggggcctct cgatgatagt tttgatatct ggggccaagg gacaatggtc    360

accgtctcaa gcgcctccac caagggccca tcggtcttcc ccctggcacc ctcctccaag    420

agcacctctg ggggcacagc ggccctgggc tgcctggtca aggactactt ccccgaaccg    480

gtgacggtgt cgtggaactc aggcgccctg accagcggcg tccacacctt cccggctgtc    540

ctacagtcct caggactcta ctccctcagc agcgtagtga ccgtgccctc cagcagcttg    600

ggcacccaga cctacatctg caacgtgaat cacaagccca gcaacaccaa ggtggacaag    660

aaagttgagc ccaaatcttg t                                              681
```

<210> SEQ ID NO 76
<211> LENGTH: 645
<212> TYPE: DNA
<213> ORGANISM: Mus musculus

<400> SEQUENCE: 76

```
cttgacatcc agttgaccca gtctccaccc tccctgtctg catctgtagg agacagagtc     60

actatcactt gccaggcgcc tcacgacatt aagaacaatt taaattggta tcaacagaaa    120

ccagggaaag cccctaaact cctgatcttc gacgcatcta atttggagac gggagtccca    180

tcaagattca gtggaagtgg atctgggaca aattttgtgc tcaccatcag cagcctgcag    240

cctgaagata ttgcaactta ttactgtcaa cagtttgatg atctcccgct cactttcggc    300

ggagggacca aggtagacat gaaacgaact gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac gaagtctacg cctgcgaagt cacccatcag    600

ggcctgagct cgcccgtcac aaagagcttc aacaggggag agtgt                    645
```

<210> SEQ ID NO 77
<211> LENGTH: 681
<212> TYPE: DNA
<213> ORGANISM: Mus musculus

<400> SEQUENCE: 77

```
caggtacagc tgcagcagtc aggtccagga ctggtgaacc cctcgcagac cctctcagtc     60

acatgtgcca tctccgggga cagtgtctct agcaacagtg ctgcttggaa ctggatcagg    120

cagtccccat cgagaggcct tgagtggctg gggaggacat actacaggtc gaagtggtat    180

aatgattatg cagtatctgt gaaaagtcga ataaccatca aaccagacac atccaagaac    240

cagttctccc tgcagctgaa ctctgtgact cccgacgaca cggctgtgta ttactgtgca    300

agagatccgg gggggtctct cgatgattct tttgatatct ggggccaagg gaccacggtc    360

accgtctcaa gcgcctccac caagggccca tcggtcttcc ccctggcacc ctcctccaag    420

agcacctctg ggggcacagc ggccctgggc tgcctggtca aggactactt ccccgaaccg    480

gtgacggtgt cgtggaactc aggcgccctg accagcggcg tccacacctt cccggctgtc    540

ctacagtcct caggactcta ctccctcagc agcgtagtga ccgtgccctc cagcagcttg    600

ggcacccaga cctacatctg caacgtgaat cacaagccca gcaacaccaa ggtggacaag    660

aaagttgagc ccaaatcttg t                                              681
```

<210> SEQ ID NO 78
<211> LENGTH: 645
<212> TYPE: DNA
<213> ORGANISM: Mus musculus

<400> SEQUENCE: 78

```
cttgacatcc agatgaccca gtctccaccc tccctgtctg catctgtagg agacagagtc     60

actatcactt gccaggcgcc tcacgacatt aagaacaatt taaattggta tcaacagaaa    120

ccagggaaag cccctaaact cctgatcttc gacgcatcta atttggagac gggagtccca    180

tcaagattca gtggaagtgg atctgggaca aattttgtgc tcaccatcag cagcctgcag    240

cctgaagata ttgcaactta ttactgtcaa cagtttgatg atctcccgct cactttcggc    300

ggagggacca aggtagacat gaaacgaact gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgt                    645
```

<210> SEQ ID NO 79
<211> LENGTH: 696
<212> TYPE: DNA
<213> ORGANISM: Mus musculus

<400> SEQUENCE: 79

```
caggtgcagc tgcaggagtc gggcccagga ctggtgaagc cctcggagac cctgtccctc     60

acttgcactg tctctggtgg ctccttcagc agttactact ggagctggat ccggcagccc    120

ccagggaagg gactggagtg gattgggtat atttctgaca gtgggagcac caactacaac    180

ccctccctcc agtctcgagt caccatatca ttagacacgt ccaagaacca gttctccctg    240

aaactgaact ctgtgaccgc cacagacacg gccgtgtatt actgtgcgag aggcccgcct    300

attcatgatt acgtttgggg gagttatcgc cgcccctcgc gagaatatga tatctggggc    360

caagggacaa tggtcaccgt ctcaagcgcc tccaccaagg gcccatcggt cttccccctg    420

gcaccctcct ccaagagcac ctctgggggc acagcggccc tgggctgcct ggtcaaggac    480
```

-continued

```
tacttccccg aaccggtgac ggtgtcgtgg aactcaggcg ccctgaccag cggcgtccac    540

accttcccgg ctgtcctaca gtcctcagga ctctactccc tcagcagcgt agtgaccgtg    600

ccctccagca gcttgggcac ccagacctac atctgcaacg tgaatcacaa gcccagcaac    660

accaaggtgg acaagaaagt tgagcccaaa tcttgt                              696
```

<210> SEQ ID NO 80
<211> LENGTH: 654
<212> TYPE: DNA
<213> ORGANISM: Mus musculus

<400> SEQUENCE: 80

```
cttaatttta tgctgactca gccccactct gtgtcggagt ctccggggaa gacggttact     60

atctcctgca cccgcagcag tggcagcgtt gccagcaact atgtccactg gtaccagcag    120

cgaccgggca gttcccccctc cattctaatc catgagttta acataagacc ctctggggtc    180

cctgatcggt tctcaggctc catcgacagc tcctccaact ctgcctccct caccatctct    240

ggactgacga ctgaggacga ggctgattac tattgtcagt cttctgtcaa caaccttcaa    300

tgggtgctcg gcggagggac caagctgacc gtcctgggtc agcccaaggc tgccccctcg    360

gtcactctgt tcccaccctc ctctgaggag cttcaagcca acaaggccac actggtgtgt    420

ctcataagtg acttctaccc gggagccgtg acagtggcct ggaaggcaga tagcagcccc    480

gtcaaggcgg gagtggagac caccacaccc tccaaacaaa gcaacaacaa gtacgcggcc    540

agcagctacc tgagcctgac gcctgagcag tggaagtccc acaaaagcta cagctgccag    600

gtcacgcatg aagggagcac cgtggagaag acagtggccc ctacagaatg ttca          654
```

<210> SEQ ID NO 81
<211> LENGTH: 681
<212> TYPE: DNA
<213> ORGANISM: Mus musculus

<400> SEQUENCE: 81

```
caggtacagc tgcagcagtc aggtccagga ctggtgaagc cctcgcagac cctctcactc     60

acctgtgcca tctccgggga cagtgtctct agcaacagtg ctgcttggaa ctggatcagg    120

cagtccccat cgagaggcct tgagtggctg ggaaggacat actacaggtc gaagtggtat    180

aatgattatg cagtatctgt gaaaagtcga ataaccatca aaccagacac atccaagaac    240

cagttctccc tgcagctgaa ctctgtgact cccgacgaca cggctgtgta ttactgtgca    300

agagatccgg gggggtctct cgatgattct tttgatatct ggggccaagg gacaatggtc    360

accgtctcaa gcgcctccac caagggccca tcggtcttcc ccctggcacc ctcctccaag    420

agcacctctg ggggcacagc ggccctgggc tgcctggtca aggactactt ccccgaaccg    480

gtgacggtgt cgtggaactc aggcgccctg accagcggcg tccacacctt cccggctgtc    540

ctacagtcct caggactcta ctccctcagc agcgtagtga ccgtgccctc cagcagcttg    600

ggcacccaga cctacatctg caacgtgaat cacaagccca gcaacaccaa ggtggacaag    660

aaagttgagc ccaaatcttg t                                              681
```

<210> SEQ ID NO 82
<211> LENGTH: 660
<212> TYPE: DNA
<213> ORGANISM: Mus musculus

<400> SEQUENCE: 82

```
cttgatgttg tgatgactca gtctccactc tccctgcccg tcacccctgg agagccggcc     60
```

```
tccatctcct gcaggtctag tcagagcctc ctgcgtagta atggatacaa ctatttagat    120

tggtacctgc agaagccagg gcagtctcca cagctcctga tctatttggg ttctactcgg    180

gcctccgggg tccctgacag gttcagtggc agtggatcgg gcacagattt tacactgaaa    240

atcagcagag tggaggctga agatgttggg gtttattact gcatgcaagc ttttcaaact    300

ccgctcactt tcggcggagg gaccaagatg gagatcaaac gaactgtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 83
<211> LENGTH: 681
<212> TYPE: DNA
<213> ORGANISM: Mus musculus

<400> SEQUENCE: 83

```
caggtacagc tgcagcagtc aggtccagga ctggtgaagc cctcgcagac cctctcactc     60

acctgtgcca tctccgggga cagtgtctct agcaacagtg ctgcttggaa ctggatcagg    120

cagtccccat cgagaggcct tgagtggctg ggaaggacat actacaggtc caagtggtat    180

aatgattatg cagtatccgt gaaaagtcga ataattatca acccagacac atccaagaac    240

cagttctccc tgcagctgaa ctctgtgact cccgaggaca cggctgtgta ttactgtgca    300

agagatccgg gggggcctct cgatgatagt tatgatatct ggggccaagg gacaatggtc    360

accgtctcaa gcgcctccac caagggccca tcggtcttcc ccctggcacc ctcctccaag    420

agcacctctg ggggcacagc ggccctgggc tgcctggtca aggactactt ccccgaaccg    480

gtgacggtgt cgtggaactc aggcgccctg accagcggcg tccacacctt cccggctgtc    540

ctacagtcct caggactcta ctccctcagc agcgtagtga ccgtgccctc cagcagcttg    600

ggcacccaga cctacatctg caacgtgaat cacaagccca gcaacaccaa ggtggacaag    660

aaagttgagc ccaaatcttg t                                              681
```

<210> SEQ ID NO 84
<211> LENGTH: 660
<212> TYPE: DNA
<213> ORGANISM: Mus musculus

<400> SEQUENCE: 84

```
cttgaaattg tgctgactca gtctccactc tccctgcccg tcacccctgg agagccggcc     60

tccatctcct gcaggtctag tcagagcctc ctgcgtagta atggatacaa ctatttagat    120

tggtacctgc agaagccagg gcagtctcca cagctcctga tctatttggg ttctaatcgg    180

gcctccgggg tccctgacag gttcagtggc agtggatcag gcacagattt tacactgaaa    240

atcagcagag tggaggctga ggatgttggg gtttattact gcatgcaagc ttttcaaact    300

ccgctcactt tcggcggagg gaccaagatg gagatcaaac gaactgtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540
```

```
ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 85
<211> LENGTH: 675
<212> TYPE: DNA
<213> ORGANISM: Mus musculus

<400> SEQUENCE: 85

```
caggtgcagc tggtggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcaagt attagtgcta gtggtggtag cacagactac    180

gcagactccg tgaagggcag attcaccatc tccagagaca attccaagaa cactctgtat    240

cttcaaatga gcagtctgag agctgaggac acggctgtgt attactgtgt gaaagagcgt    300

ccggattacg atttttggag tgcgttcgac ccctggggcc agggaaccct ggtcaccgtc    360

tcaagcgcct ccaccaaggg cccatcggtc ttccccctgg caccctcctc caagagcacc    420

tctgggggca cagcggccct gggctgcctg gtcaaggact acttccccga accggtgacg    480

gtgtcgtgga actcaggcgc cctgaccagc ggcgtccaca ccttcccggc tgtcctacag    540

tcctcaggac tctactccct cagcagcgta gtgaccgtgc cctccagcag cttgggcacc    600

cagacctaca tctgcaacgt gaatcacaag cccagcaaca ccaaggtgga caagaaagtt    660

gagcccaaat cttgt                                                     675
```

<210> SEQ ID NO 86
<211> LENGTH: 660
<212> TYPE: DNA
<213> ORGANISM: Mus musculus

<400> SEQUENCE: 86

```
cttgatgttg tgatgactca gtctccactc tccctgcccg tcacccctgg agagccggcc     60

tccatctcct gcaggtctag tcagagcctc ctgcatagta atggatacaa ctatttggat    120

tggtacctgc agaagccggg gcagtctcca cagctcctga tctatttggg ttctaatcgg    180

gcctccgggg tccctgacag gttcagtggc agtggatcag gcacagattt tacactgaaa    240

atcagcagag tggaggctga ggatgttggg gtttattact gcatgcaagg tacacactgg    300

cctccgactt ttggccaggg gaccaagctg gagatcaaac gaactgtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaact ctacgcctgc    600

gaagtcaccc atcagggcct gagctcgccc gtcacaaaga gcttcaacag gggagagtgt    660
```

<210> SEQ ID NO 87
<211> LENGTH: 963
<212> TYPE: DNA
<213> ORGANISM: Mus musculus

<400> SEQUENCE: 87

```
ttgctagcac cctcctccaa gagcacctct gggggcacag cggccctggg ctgcctggtc     60

aaggactact tccccgaacc ggtgacggtg tcgtggaact caggcgccct gaccagcggc    120

gtccacacct tcccggctgt cctacagtcc tccggactct actccctcag cagcgtagtg    180
```

```
accgtgccct ccagcagctt gggcacccag acctacatct gcaacgtgaa tcacaagccc    240

agcaacacca aggtggacaa gaaagttgag cccaaatctt gtgacaaaac tcacacatgc    300

ccaccgtgcc cagcacctga actcctgggg ggaccgtcag tcttcctctt ccccccaaaa    360

cccaaggaca ccctcatgat ctcccggacc cctgaggtca catgcgtggt ggtggacgtg    420

agccacgaag accctgaggt caagttcaac tggtacgtgg acggcgtgga ggtgcataat    480

gccaagacaa agccgcggga ggagcagtac aacagcacgt accgtgtggt cagcgtcctc    540

accgtcctgc accaggactg gctgaatggc aaggagtaca agtgcaaggt ctccaacaaa    600

gccctcccag cccccatcga gaaaaccatc tccaaagcca aagggcagcc ccgagaacca    660

caggtgtaca ccctgccccc atcccgggat gagctgacca agaaccaggt cagcctgacc    720

tgcctggtca aaggcttcta tcccagcgac atcgccgtgg agtgggagag caatgggcag    780

ccggagaaca actacaagac cacgcctccc gtgctggact ccgacggctc cttcttcctc    840

tacagcaagc tcaccgtgga caagagcagg tggcagcagg ggaacgtctt ctcatgctcc    900

gtgatgcatg aggctctgca caaccactac acgcagaaga gcctctccct gtctccgggt    960

aaa                                                                  963
```

```
<210> SEQ ID NO 88
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 88

Gly Asp Ser Val Ser Ser Asn Ser Ala Trp Asn
1               5                   10


<210> SEQ ID NO 89
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 89

Gly Asp Ser Val Ser Ser Asn Ala Trp Asn
1               5                   10


<210> SEQ ID NO 90
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 90

Arg Thr Tyr Tyr Arg Ser Lys Trp Tyr Asn Asp Tyr Ala Glu Ser Val
1               5                   10                  15

Lys Ser


<210> SEQ ID NO 91
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 91
```

Asp Pro Gly Gly Ser Leu Asp Asp Ser Phe Asp Ile
1 5 10

<210> SEQ ID NO 92
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 92

Gly Asp Ser Val Ser Ser Lys Ser Ala Ala Trp Asn
1 5 10

<210> SEQ ID NO 93
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 93

Asp Pro Gly Gly Pro Leu Asp Asp Ser Tyr Asp Ile
1 5 10

<210> SEQ ID NO 94
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 94

Asp Ser Gly Leu Gly Ser Asp Tyr Phe Asp Tyr Phe Asp Tyr
1 5 10

<210> SEQ ID NO 95
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 95

Arg Thr Tyr Tyr Arg Ser Lys Trp Tyr Tyr Asp Tyr Ala Val Ser Val
1 5 10 15

Lys Ser

<210> SEQ ID NO 96
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 96

Asp Pro Gly Gly Ala Leu Asp Asp Ser Phe Asp Ile
1 5 10

<210> SEQ ID NO 97
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 97

Gly Phe Ile Phe Ser Asp Ala Trp Met Ser
1 5 10

<210> SEQ ID NO 98
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 98

Arg Met Lys Ser Ile Ser Asp Gly Ala Thr Ile Asp Tyr Ala Pro Pro
1 5 10 15

Val Gln Asp

<210> SEQ ID NO 99
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 99

Glu Asn Asn Tyr Glu Ser Gly Arg Arg Phe Gly Met Asp Val
1 5 10

<210> SEQ ID NO 100
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 100

Gly Phe Thr Phe Ser Ser Tyr Ala Met Ser
1 5 10

<210> SEQ ID NO 101
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 101

Ser Ile Ser Ala Ser Gly Gly Ser Thr Asp Tyr Ala Asp Ser Val Lys
1 5 10 15

Gly

<210> SEQ ID NO 102
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 102

Glu Arg Pro Asp Tyr Asp Phe Trp Ser Ala Phe Asp Pro
1 5 10

<210> SEQ ID NO 103
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 103

```
Ala Ile Ser Gly Ser Gly Gly Ser Thr Tyr Tyr Ala Asp Ser Val Lys
1               5                   10                  15

Gly
```

<210> SEQ ID NO 104
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 104

```
Asp Glu Asp Tyr Asp Tyr Val Trp Gly Ser Tyr Arg Gln Tyr Pro Ser
1               5                   10                  15

Arg Tyr
```

<210> SEQ ID NO 105
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 105

```
Asp Trp Gly Arg Asn Ile Ala Val Ala Gly Thr Leu Pro Tyr
1               5                   10
```

<210> SEQ ID NO 106
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 106

```
Gly Phe Thr Phe Ser Ser Tyr Ala Met His
1               5                   10
```

<210> SEQ ID NO 107
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 107

```
Val Ile Ser Tyr Asp Gly Ser Asn Lys Tyr Tyr Ala Asp Ser Val Lys
1               5                   10                  15

Gly
```

<210> SEQ ID NO 108
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 108

```
Pro Tyr Ser Ser Ser Trp Tyr Ser Val Gly Asn Tyr Gly Ile Asp Val
1               5                   10                  15
```

<210> SEQ ID NO 109
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 109

```
Gly Gly Ser Phe Ser Gly Tyr Tyr Trp Ser
1               5                   10
```

<210> SEQ ID NO 110
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 110

```
Val Gly Gly Ser Phe Ser Ser Tyr Tyr Trp Ser
1               5                   10
```

<210> SEQ ID NO 111
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 111

```
Tyr Ile Ser Asp Ser Gly Ser Thr Asn Tyr Asn Pro Ser Leu Gln Ser
1               5                   10                  15
```

<210> SEQ ID NO 112
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 112

```
Pro Pro Ile His Asp Tyr Val Trp Gly Ser Tyr Arg Arg Pro Ser Arg
1               5                   10                  15

Glu Tyr Asp Ile
            20
```

<210> SEQ ID NO 113
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 113

```
Gly Gly Ser Ile Ser Ser Ser Ser Tyr Tyr Trp Gly
1               5                   10
```

<210> SEQ ID NO 114
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 114

```
Ser Ile Tyr Tyr Ser Gly Ser Thr Tyr Tyr Asn Pro Ser Leu Lys Ser
```

1 5 10 15

<210> SEQ ID NO 115
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 115

Leu Asn Ala His Pro Ile Tyr Tyr Tyr Tyr Tyr Gly Met Asp Val
1 5 10 15

<210> SEQ ID NO 116
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 116

Arg Ser Ser Gln Leu Leu Arg Ser Asn Gly Tyr Asn Tyr Leu Asp
1 5 10 15

<210> SEQ ID NO 117
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 117

Arg Ser Ser Gln Ser Leu Leu Arg Asn Asn Gly Tyr Asn Tyr Leu Asp
1 5 10 15

<210> SEQ ID NO 118
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 118

Leu Gly Ser Asn Arg Ala Ser
1 5

<210> SEQ ID NO 119
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 119

Leu Gly Ser Thr Arg Ala Ser
1 5

<210> SEQ ID NO 120
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 120

Met Gln Ala Phe Gln Thr Pro Leu Thr
1 5

<210> SEQ ID NO 121
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 121

Arg Ser Ser Gln Ser Leu Leu Arg Ser Asn Gly Tyr Asn Leu Asp
1 5 10 15

<210> SEQ ID NO 122
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 122

Gln Ala Pro His Asp Ile Lys Asn Asn Leu Asn
1 5 10

<210> SEQ ID NO 123
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 123

Asp Ala Ser Asn Leu Glu Thr
1 5

<210> SEQ ID NO 124
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 124

Gln Gln Phe Asp Asp Leu Pro Leu Thr
1 5

<210> SEQ ID NO 125
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 125

Gln Ala Ser Gln Val Ile Asn Asn His Leu Asn
1 5 10

<210> SEQ ID NO 126
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 126

Gln Gln Ser Asp Asn Leu Pro Arg Thr
1 5

<210> SEQ ID NO 127
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 127

Gln Gln Ser Asp Asn Leu Pro Leu Thr
1               5

<210> SEQ ID NO 128
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 128

Arg Ala Ser Gln Thr Ile Ser Ser Ser Leu Ala
1               5                   10

<210> SEQ ID NO 129
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 129

Lys Ala Ser Thr Leu Glu Gly
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 130

Gln Gln Ser Tyr Thr Thr Pro Leu Thr
1               5

<210> SEQ ID NO 131
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 131

Thr Gly Ser Ser Ser Asn Ile Gly Ala Gly Phe Asp Val His
1               5                   10

<210> SEQ ID NO 132
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 132

Gly Asn Thr Asn Arg Pro Ser
1               5

```
<210> SEQ ID NO 133
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 133

Gln Ala Tyr Asp Asp Ser Leu Gln Gly Tyr Val
1               5                   10


<210> SEQ ID NO 134
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 134

Gln Ala Ser Gln Asp Ile Phe Asn Tyr Leu Asn
1               5                   10


<210> SEQ ID NO 135
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 135

Asp Ala Ser Asn Leu Ala Ser
1               5


<210> SEQ ID NO 136
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 136

Gln Gln His His Ser Leu Pro Pro Ala
1               5


<210> SEQ ID NO 137
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 137

Arg Ser Ser Gln Ser Leu Leu His Ser Asn Gly Tyr Asn Tyr Leu Asp
1               5                   10                  15


<210> SEQ ID NO 138
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 138

Met Gln Gly Thr His Trp Pro Pro Thr
1               5


<210> SEQ ID NO 139
```

<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 139

Ser Gly Asp Asn Leu Gly Tyr Lys Tyr Ala Ser
1               5                   10

<210> SEQ ID NO 140
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 140

Gln Asp Lys Lys Arg Pro Ser
1               5

<210> SEQ ID NO 141
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 141

Gln Ala Trp Asp Ser Ser Thr Ser Val Val
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 142

Ser Gly Asp Lys Leu Gly Gln Lys Tyr Val Ser
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 143

Gln Asp Asp Lys Arg Pro Ser
1               5

<210> SEQ ID NO 144
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 144

Gln Ala Trp Asp Ser Asn Thr Ala Pro Tyr Val
1               5                   10

<210> SEQ ID NO 145
<211> LENGTH: 14

<212> TYPE: PRT
<213> ORGANISM: Artificial Sequence
<220> FEATURE:
<223> OTHER INFORMATION: Synthetic polypeptide

<400> SEQUENCE: 145

Thr Leu Arg Arg Asp Ile Asp Ile Gly Thr Ala Arg Ile Tyr
1 5 10

<210> SEQ ID NO 146
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 146

Thr Glu Lys Ala Ser Gly Val
1 5

<210> SEQ ID NO 147
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 147

Leu Ile Trp His Asn Asn Ala Trp Val
1 5

<210> SEQ ID NO 148
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 148

Thr Arg Ser Ser Gly Ser Val Ala Ser Asn Tyr Val His
1 5 10

<210> SEQ ID NO 149
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 149

Pro Ser Gly Val Pro Asp Arg
1 5

<210> SEQ ID NO 150
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 150

Gln Ser Ser Val Asn Asn Leu Gln Trp
1 5

<210> SEQ ID NO 151
<211> LENGTH: 11
<212> TYPE: PRT

-continued

```
<213> ORGANISM: Artificial Sequence
<220> FEATURE:
<223> OTHER INFORMATION: Synthetic polypeptide

<400> SEQUENCE: 151

Arg Ala Ser Gln Ser Val Ser Ser Tyr Leu Ala
1               5                   10


<210> SEQ ID NO 152
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 152

Asp Ala Ser Asn Arg Ala Thr
1               5


<210> SEQ ID NO 153
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 153

Gln Gln Arg Ser Asn Trp Pro Pro Met Tyr Thr
1               5                   10
```

ANTIBODIES AND PHARMACEUTICAL COMPOSITIONS THEREOF WHICH BIND UROKINASE-TYPE PLASMINOGEN ACTIVATOR RECEPTOR (UPAR)

CROSS-REFERENCE TO RELATED APPLICATIONS

This application claims priority benefit of U.S. provisional application Ser. No. 61/304,334, filed Feb. 12, 2010, which application is incorporated herein by reference in its entirety.

STATEMENT REGARDING FEDERALLY SPONSORED RESEARCH

This invention was made with government support under Grant Nos. CA072006 and CA128765 awarded by the National Institutes of Health and Grant No. 073210 awarded by the National Institute of General Medical Sciences. The government has certain rights in the invention

INTRODUCTION

The urokinase plasminogen activator receptor (uPAR or CD87 (Cluster of Differentiation 87)) is a glycosylated protein of 45-55 kDa consisting of three homologous cysteine-rich domains. The protein is localized to the extracellular leaf of the plasma membrane through a glycosylphosphatidylinositol anchor. UPAR mediates a wide variety of cellular processes including inflammation, metastasis and invasion, tissue remodeling, angiogenesis, and cell adhesion.

Many of these processes are initiated by the highly specific binding of various ligands to membrane-bound uPAR at the cell surface. One such interaction is between uPAR and uPA, which mediates both extracellular and intracellular signaling events.

Binding of extracellular pro-uPA to uPAR facilitates its activation. In turn, uPA activates proteases, such as plasmin, which directly and indirectly degrade the extracellular matrix (ECM). Furthermore, plasmin can activate pro-uPA leading to a positive feedback loop that accelerates ECM degradation. uPAR is also able to act intracellularly by activating proliferative signal transduction pathways. uPAR is believed to directly associate with integrin family adhesion receptors in complexes that mediate RGD-independent cell signaling and migration. Accordingly, uPAR plays a role in the development of cancer and the metastasis of cancer.

SUMMARY

The present disclosure relates to agents (e.g. antibodies) that bind to and modulate the activity of urokinase plasminogen activator receptor (uPAR/CD87), compositions comprising the agents, and methods involving use of the compositions.

Also provided by the disclosure is an antibody comprising a heavy chain variable region comprising one or more Compelementary Determining Regions (CDRs); and/or a light chain variable region comprising one or more CDRs, in which the antibody competes with a ligand such as uPA and/or an integrin protein for uPAR binding. Methods for using the antibodies, combinations of different antibodies, and compositions thereof are also provided.

DETAILED DESCRIPTION OF EMBODIMENTS

Figure 1:
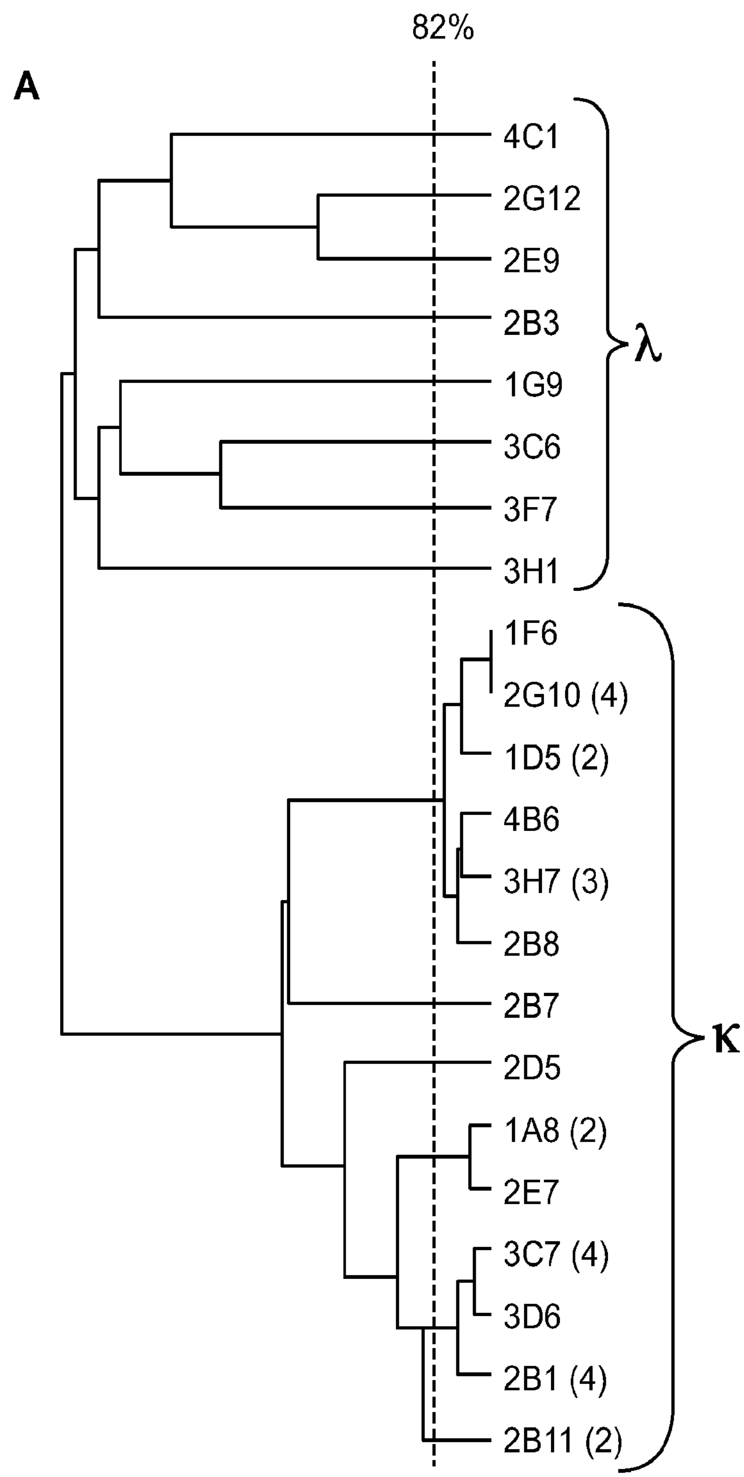
FIGS. 1A-1B: Sequence homology for uPAR-binding Fabs identified by phage display. Panel A, The heavy and light chain protein sequences of the 22 unique clones were aligned to generate a percent identity tree diagram. Panel B, The sequences of the CDR loops of each unique Fab were aligned and shaded to indicate sequence identity. H1 (SEQ ID NOs: 88, 89, 40, 92, 97, 100, 106, 109, 110 and 113), H2 (SEQ ID NOs:42, 90, 95, 98, 101, 103, 107, 41, 111 and 114), and H3 (SEQ ID NOs:44, 91, 93, 94, 96, 99, 102, 104, 105, 108, 43, 112, 115) refer to heavy chain ($V_H$) CDR1, CDR2, and CDR3, respectively. Similarly, L1 (SEQ ID NOs:116, 34, 117, 121, 122, 125, 128, 131, 134, 137, 139, 142, 145, 33, 148, 151), L2 (SEQ ID NOs:36, 118, 119, 123, 129, 132, 135, 140, 143, 146, 35, 149, 152), and L3 (SEQ ID NOs:38, 120, 124, 126, 127, 130, 133, 136, 138, 141, 144, 147, 37, 150, 153) refer to light chain ($V_L$) CDR1, CDR2, and CDR3, respectively.

The present disclosure relates to agents (e.g. antibodies, aptamers, and/or peptides, etc.) that bind to urokinase plasminogen activator receptor (uPAR), compositions comprising the agents, and methods involving use of the compositions. The agents disclosed herein and methods of use can modulate uPAR by disrupting binding of uPAR to other proteins.

Certain antibodies disclosed herein were found by screening a human Fab phage display library for uPAR binding. Several studies of the antibody and uPAR reveal that the antibody comprises features that prevent binding of ligand such as uPA and/or integrin proteins to uPAR as well as other features that render the antibodies specific for cells expressing uPAR. The data presented herein support the application of the agents (e.g. antibodies) that disrupt uPAR binding in methods and compositions, including the diagnosis and treatment of multiple types of human diseases (e.g. cancer).

Methods of screening are also provided to identify or engineer a uPAR-binding agent that specifically inhibits/disrupt uPAR binding to its partners.

Kits containing one or more compositions of the present disclosure, as well as those with instructions for use in a method of the present disclosure also are provided.

Before the present invention and specific embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. That the upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "an antigen" includes a plurality of such antigens and reference to "the peptide" includes reference to one or more peptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

When describing the compositions, pharmaceutical formulations containing such, and methods of producing and using such compositions, the following terms have the following meanings unless otherwise indicated. It should also be understood that any of the moieties defined forth below may be substituted with a variety of substituents, and that the respective definitions are intended to include such substituted moieties within their scope.

The terms "polypeptide" and "protein" are used interchangeably throughout the application and mean at least two covalently attached amino acids, which includes proteins, polypeptides, oligopeptides, peptides, and fragments thereof. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. Normally, the amino acids are in the (S) or L-configuration, except for glycine. If non-naturally occurring side chains are used, non-amino acid substituents may be used, for example to prevent or retard in vivo degradation. Naturally occurring amino acids may be used and the protein may be a cellular protein that is either endogenous or expressed recombinantly. In some cases, the proteins of the present invention may be synthesized using any protein in vivo or in vitro protein synthesis technique understood in the art. The terms "polypeptide" and "protein" include fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Polypeptides may be of any size, and the term "peptide" refers to polypeptides that are 5-50 residues (e.g., 8-20 residues) in length. In some cases, proteins may be modified by covalent or non-covalent attachment of other peptide or non-peptide molecules including but not limited to one or more molecules or compositions comprised of fluorescent dyes, polyethylene glycol or other polymer, biotin, enzymes, radionuclides, MRI contrast agents, therapeutics, or chemotherapeutics as described in more detail below.

By "nucleic acid" herein is meant either DNA or RNA, or molecules which contain both deoxy- and ribonucleotides. Nucleic acid may be naturally occurring or synthetically made, and as such, includes analogs of naturally occurring polynucleotides in which one or more nucleotides are modified over naturally occurring nucleotides.

The term, "endogenous", as used herein, refers to biomolecules, such as proteins, that are naturally-occurring within an organism.

The term "carrier" as used in the context of a carrier conjugated to an antibody includes a peptide or protein carrier, a non-peptide or protein carrier (e.g. a non-peptide polymer).

The term "cell surface antigen" (or "cell surface epitope") refers to an antigen (or epitope) on surface of a cell that is extracellularly accessible during at least one cell cycle or developmental stage of the cell, including antigens that are extracellularly accessible during all stages of the cell cycle. "Extracellularly accessible" in this context refers to an antigen that can be bound by an antibody provided outside the cell without need for permeabilization of the cell membrane.

The term "chemotherapy" as used herein refers to use of an agent (e.g., drug, antibody, etc.), particularly an agent(s) that is selectively destructive to a cancerous cell, in treatment of a disease, with treatment of cancer being of particular interest.

A "cancer cell" as used herein refers to a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell" or "cancerous cell", and encompasses cancer cells of a solid tumor, a semi-solid tumor, a primary tumor, a metastatic tumor, and the like.

The term "conjugated" generally refers to a chemical linkage, either covalent or non-covalent, usually covalent, that proximally associates one molecule of interest with second molecule of interest.

The terms "antigen" and "epitope" are well understood in the art and refer to the portion of a macromolecule (e.g., a polypeptide) which is specifically recognized by a component of the immune system, e.g., an antibody or a T-cell antigen receptor. As used herein, the term "antigen" encompasses antigenic epitopes, e.g., fragments of an antigen which are antigenic epitopes. Epitopes can be recognized by antibodies in solution, e.g. free from other molecules. Epitopes can be recognized by T-cell antigen receptor when the epitope is associated with a class I or class II major histocompatibility complex molecule.

The terms "derivative" and "variant" refer to without limitation any compound or antibody which has a structure or sequence derived from the compounds and antibodies of the present disclosure and whose structure/sequence is sufficiently similar to those disclosed herein and based upon that similarity, would be expected, by one skilled in the art, to exhibit the same or similar activities and utilities as the claimed and/or referenced compounds or antibody. In some cases, variants may be 50%, 55%, 60%, 65%, 70%, 75%, 80%, 85%, 90%, 95%, 99%, or more homologous or identical at least one compound or antibody of the present disclosure.

The term "effective amount" of a composition as provided herein is intended to mean a non-lethal but sufficient amount of the composition to provide the desired utility. For instance, for eliciting a favorable response in a subject to treat a disorder or infection, the effective amount is the amount which eliminates or diminishes the symptoms associated with the disorder, e.g., so as to provide for control of cancer metastasis, to eliminate cancer cells, decrease bacterial or viral infection. As will be pointed out below, the exact amount required will vary from subject to subject, depending on the species, age, and general condition of the subject, the severity of the condition or disease that is being treated, the particular composition used, its mode of administration, and the like. Thus, it is not possible to specify an exact "effective amount." However, an appropriate effective amount may be determined by one of ordinary skill in the art using only routine experimentation.

The term "immunotherapy" refers to treatment of disease (e.g., viral or bacterial infection, or cancer) by modulating an immune response to a disease antigen. In the context of the present application, immunotherapy refers to providing an antibacterial and/or anti-cancer immune response in a subject by administration of an antibody (e.g., a monoclonal antibody).

The term "in combination with" as used herein refers to uses where, for example, a first therapy is administered during the entire course of administration of a second therapy; where the first therapy is administered for a period of time that is overlapping with the administration of the second therapy, e.g. where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same or different routes, and in the same or different dosage form type.

The term "isolated" is intended to mean that a compound is separated from all or some of the components that accompany it in nature. "Isolated" also refers to the state of a compound separated from all or some of the components that accompany it during manufacture (e.g., chemical synthesis, recombinant expression, culture medium, and the like).

The term "antibody" refers to a polypeptide composed of complementarity determining regions (CDRs) that confer specific binding affinity of the polypeptide for an antigen. "Antibody" encompasses polyclonal and monoclonal antibody preparations where the antibody may be of any class of interest (e.g., IgM, IgG, and subclasses thereof), as well as preparations including hybrid antibodies, altered antibodies, covalently modified antibodies, $F(ab')_2$ fragments, F(ab) molecules, Fv fragments, single chain fragment variable displayed on phage (scFv), single chain antibodies (e.g. single-chain Fab), single domain antibodies, affibodies, diabodies, chimeric antibodies, human antibodies, humanized antibodies, and functional fragments thereof which exhibit immunological binding properties of the parent antibody molecule. The antibodies described herein may be detectably labeled, e.g., with a radioisotope, an enzyme which generates a detectable product, a fluorescent protein, and the like. The antibodies may be further conjugated to other moieties, such as a cytotoxic molecule or other molecule (e.g., to provide for delivery of an anti-cancer drug to a cancer cell), members of specific binding pairs, e.g., biotin (member of biotin-avidin specific binding pair), and the like. The antibodies may also be bound to a support (e.g., a solid support), such as a polystyrene plate or bead, test strip, and the like.

Antibodies can include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (usually of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

Light or heavy chain variable regions are generally composed of a "framework" region (FR) interrupted by three hypervariable regions, also called CDRs. The extent of the framework region and CDRs have been precisely defined (see, "Sequences of Proteins of Immunological Interest," E. Kabat et al., U.S. Department of Health and Human Services, 1991, and Lefranc et al. IMGT, the international ImMunoGeneTics information System®. Nucl. Acids Res., 2005, 33, D593-D597)). A detailed discussion of the Kabat numbering system is provided on the World Wide Web at kabatdatabase.com/index.html. CDR and framework sequences may also be defined by the Chothia numbering system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

The term "monoclonal antibody" refers to an antibody composition having a homogeneous antibody population. The term is not limited by the manner in which it is made. The term encompasses whole immunoglobulin molecules, as well as Fab molecules, F(ab')2 fragments, Fv fragments, single chain fragment variable displayed on phage (scFv), fusion proteins comprising an antigen-binding portion of an antibody and a non-antibody protein, and other molecules that exhibit binding properties of the parent monoclonal antibody molecule. Methods of making polyclonal and monoclonal antibodies are known in the art and described more fully below.

The term "specific binding of an antibody" or "antigen-specific antibody" in the context of a characteristics of an antibody refers to the ability of an antibody to preferentially bind to a particular antigen that is present in a homogeneous mixture of different antigens. In certain embodiments, a specific binding interaction will discriminate between desirable and undesirable antigens (or "target" and "non-target" antigens) in a sample, in some embodiments more than about 10 to 100-fold or more (e.g., more than about 1000- or 10,000-fold). The affinity between an antibody and antigen when they are specifically bound in an antibody-antigen complex can be characterized by a $K_D$ (dissociation constant) of less than $10^{-6}$M, less than $10^{-7}$ M, less than $10^{-8}$M, less than $10^{-9}$M, less than $10^{-9}$ M, less than $10^{-11}$ M, or less than about $10^{12}$ M or less.

"Conservative amino acid substitution" refers to a substitution of one amino acid residue for another sharing chemical and physical properties of the amino acid side chain (e.g., charge, size, hydrophobicity/hydrophilicity). "Conservative substitutions" are intended to include but are not limited to substitution within the following groups of amino acid residues: gly, ala; val, ile, leu; asp, glu; asn, gln; ser, thr; lys, arg; and phe, tyr. Conservative amino acid substitutions in the context of an antibody disclosed herein are selected so as to preserve the interaction between the antibody and the protease of interest. Other conservative substitutions that can preserve size, chemical property, and/or shape includes val, thr; asp, asn, glu, gln; leu, phe, tyr, trp; lys, leu; trp, phe, and tyr; and ala, val, tyr.

The term "pharmaceutically acceptable" refers to a material that is not biologically or otherwise undesirable, i.e., the material is of a medically acceptable quality and composition that may be administered to an individual along with the selected active pharmaceutical ingredient without causing any undesirable biological effects or interacting in a deleterious manner with any of the other components of the pharmaceutical composition in which it is contained.

The term "pharmaceutically acceptable excipient" as used herein refers to any suitable substance which provides a pharmaceutically acceptable vehicle for administration of a compound(s) of interest to a subject. "Pharmaceutically acceptable excipient" can encompass substances referred to as pharmaceutically acceptable diluents, pharmaceutically acceptable additives and pharmaceutically acceptable carriers.

The term "purified" is intended to mean a compound of interest has been separated from components that accompany it in nature and provided in an enriched form. "Purified" also refers to a compound of interest separated from components that can accompany it during manufacture (e.g., in chemical synthesis, recombinant expression, culture medium, and the like) and provided in an enriched form. Typically, a compound is substantially pure when it is at least 50% to 60%, by weight, free from organic molecules with which it is naturally associated or with which it is associated during manufacture. Generally, the preparation is at least 75%, more usually at least 90%, and generally at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample having a compound that binds an antibody of interest. Purity can be measured by any appropriate method, e.g., chromatography, mass spectroscopy, HPLC analysis, polyacrylamide gel electrophoresis, etc.

The term "subject" is intended to cover humans, mammals and other animals which contain uPAR in any fashion. The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

In the context of cancer therapies and diagnostics described herein, "subject" or "patient" is used interchangeably herein to refer to a subject having, suspected of having, or at risk of developing a tumor. In some cases, the cancer is one associated with cancerous cells expressing an active and/or dysregulated uPAR. Samples obtained from such subject are likewise suitable for use in the methods of the present disclosure.

As used herein, the terms "determining," "measuring," and "assessing," and "assaying" are used interchangeably and include both quantitative and qualitative determinations.

It is further noted that the claims may be drafted to exclude any optional or alternative element. As such, this statement is intended to serve as antecedent basis for use of such exclusive terminology as "solely", "only" and the like in connection with the recitation of claim elements, or the use of a "negative" limitation.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed. To the extent a definition of a term set out in a document incorporated herein by reference conflicts with the definition of a term explicitly defined herein, the definition set out herein controls.

Examples of methods and compositions employable therein are described first in greater detail, followed by a review of the various specific compositions, formulations, kits and the like that may find use in the methods of the present disclosure, as well as a discussion of representative applications in which the methods and compositions of the present disclosure find use.

UPAR-Binding Agents

The present disclosure provides uPAR-binding agents (e.g. anti-uPAR antibodies, also referred to as "uPAR antibodies"). Examples of uPAR-binding agents include but are not limited to aptamers (nucleic acids and/or peptides), antibodies, small molecules, and other biomolecules. Where the agent is an antibody, the antibody includes a whole antibody (e.g. IgG), an antigen-binding fragment thereof, single-chain Fabs, single chain Fv (e.g. diabodies or $V_H$H), Fab'2, minibody, and synthetic uPAR antibody that comprise portions of an antibody. uPAR, the target of the subject agents, is also known as urokinase plasminogen activator receptor, urokinase receptor, uPA receptor, or CD87 (Cluster of Differentiation 87). UPAR is composed of three different domains of the Ly-6/uPAR/alpha-neurotoxin family. All three domains are involved in high affinity binding of the primary ligand, urokinase. Besides the primary ligand urokinase, uPAR interacts with several other proteins, including vitronectin, the uPAR associated protein (uPARAP) and the integrin family of membrane proteins.

As used herein, "uPAR" refers to urokinase plasminogen activator receptor, including those whose amino acid sequences that are at least about 80%, at least about 85%, at least about 90%, at least about 95%, at least about 98%, at least about 99%, or 100% identical to the amino acid sequence of a naturally-occurring allelic variant and/or isoform thereof. Variants can also include mutations whose expression is associated with cancer. Many mammalian uPARs and their corresponding isoforms are known in the art. For example, the amino acid sequence of the longest human isoform is available as GenBank Accession No. NP_002650.1 and UniProt Accession No. Q03405.

Binding of ligands and/or integrins to uPAR is involved in signaling that can lead to proliferation. Certain signaling cascades that are initiated by activated uPAR mediate the regulation of cellular shape, adhesion, and mobility, and thus play a role in cell invasion. Accordingly, preventing ligands such as uPA and/or integrins (e.g. β1 integrins, such as α5β1 or α3β1) from binding to uPAR can reduce the effects of proliferative signaling cascades and those signals leading to angiogenesis. A subject binding agent can exhibit features that allow not only competitive binding with proteins (e.g. integrins and/or ligands) that bind to uPAR but also potent inhibition of uPAR-mediated cell signaling. UPAR-binding agents of the present disclosure can find use in a variety of applications, including use in various methods of treating a host suffering from a disease or condition associated with uPAR signaling, as well as in diagnosis of various diseases and conditions associated with uPAR expression. For example, a subject agent, such as an antibody, is specific for the integrin-binding site on uPAR and may be used to inhibit the proliferation or metastasis of cancer cells. More uses of a subject agent will be described later.

UPAR-expressing cells can serve as targets for the uPAR antibodies of the present disclosure. For example, uPAR-binding agents (e.g. antibodies) of the present disclosure can be used to bind human cells that express surface exposed uPAR. The binding may be specific so that cells that express uPAR are labeled using the subject antibody but cells that do not express uPAR are not. The uPAR expressed in cells may be endogenous, recombinants, naturally-occurring variants and isoforms, and/or a homolog of human uPAR (murine, rat, bovine, primates, etc.). Particularly, uPAR molecules that are expressed by cancer cells can be bound by the subject antibody. Such antibody may be useful in specifically labeling cancer cells (e.g. uPAR-positive cancer) for use in a diagnostic method, described in more detail below.

As a reference, an amino acid sequence of uPAR is provided below and can also be found in RSCB Protein Data Bank identified as 3BT1. Numbering system used in the present disclosure to refer to an amino acid residue position in uPAR would be in the context of the following amino acid sequence:

(SEQ ID NO: 1)

LRCMQCKTNGDCRVEECALGQDLCRTTIVRLWEEGEELELVEKSCTHS

EKTNRTLSYRTGLKITSLTEVVCGLDLCNQGNSGRAVTYSRSRYLECI

SCGSSDMSCERGRHQSLQCRSPEEQCLDVVTHWIQEGEEGRPKDDRH

LRGCGYLPGCPGSNGFHNNDTFHFLKCCNTTKCNEGPILELENLPQNG

RQCYSCKGNSTHGCSSEETFLIDCRGPMNQCLVATGTHEPKNQSYMVR

GCATASMCQHAHLGDAFSMNHIDVSCCTKSGCNHPDLDVQYR

The present disclosure provides uPAR agents (e.g. antibodies) that compete with and/or disrupt integrin binding to uPAR. Integrins encompass β1 integrins, such as α5β1 or α3β1. The agents thus find use in inhibiting integrin binding to cells (e.g., human cells expressing uPAR). For example, antibodies of clone 3C6 inhibit α5β1 and α3β1 integrin binding to uPAR. This inhibition may be due to the binding of the antibody to an epitope involved in the interaction between integrin and uPAR (e.g. integrin binding site) or to an epitope outside of the binding site so that uPAR is modified in a way to decrease uPAR's affinity to integrin (e.g. allosteric site). As such, a uPAR antibody of the present disclosure can compete with an antibody that binds to an epitope located in the integrin-binding site (e.g. α5β1 and/or α3β1 integrin binding site). One or more epitopes of an antibody of the present disclosure can be found in domain III, which corresponds to the amino acid sequence of uPAR from about amino acid residue position 192 to about position 275. Other epitopes outside of domain III may also contribute to the binding affinity of integrin or an antibody of the present disclosure to uPAR.

Antibodies of the present disclosure include those that can compete with an antibody that binds to an epitope including one or more of the following residues: D262, E208, E230, H249, and S156, all of which are located in domain III except for S156, which is located in domain II. For example, an antibody can bind to an epitope or compete with an antibody that binds to an epitope including residue E208. In another example, the epitope can include residue H249 and D262. Alternatively, the epitope includes E230 or S156. See example 16 and FIG. 16 for detail.

The present disclosure also provides agents that compete with and/or inhibit uPA binding to uPAR. Urokinase-type plasminogen activator (uPA, also known as urokinase), an endogenous ligand of uPAR, is a member of a family of enzymes that exhibit protease activity described as EC 3.4.21.73 according to the IUMBM enzyme nomenclature. UPAR antibodies can decrease binding of uPA to uPAR by competitive inhibition, where the antibody binds to the same site of uPAR as uPA binds or at a different site outside of the uPA binding site (e.g. allosteric site), or by noncompetitive inhibition. Examples of antibodies that can inhibit uPA binding to uPAR include antibodies from clone 2E9 and antibodies from clone 2G10.

As such, a uPAR antibody of the present disclosure can compete with an antibody that binds to an epitope located in the uPA-binding site. One or more epitopes of a uPA-binding site can be found in domain I and/or domain II of uPAR. Domain I corresponds to an amino acid sequence of uPAR from about amino acid residue position 1 to about position 80. Domain II corresponds to an amino acid sequence of uPAR from about amino acid residue position 91 to about position 191.

As noted above, antibody affinity for uPAR may be described by the dissociation constant, $K_D$. Antibodies of the present disclosure, for example, include those having a $K_D$ for uPAR of less than about 1000 nM, less than about 500 nM, less than about 300 nM, less than about 200 nM, less than about 100 nM, less than about 80 nM, less than about 60 nM, less than about 55 nM, less than about 50 nM, less than about 40 nM, less than about 30 nM, less than about 25 nM, less than about 20 nM, less than about 10 nM, less than about 5 nM, less than about 2 nM, less than about 1 nM, less than about 750 pM, less than about 500 pM, less than about 300 pM, less than about 200 pM, less than about 100 pM, or less than about 50 pM. For example, the divalent IgG antibody derived from clone 2G10 has a $K_D$ of about 40.5 nM. See FIG. 4 for $K_D$ values for other examples of antibodies of the present disclosure.

UPAR antibodies of the present disclosure include antibodies that facilitate a decrease in cellular signaling associated with uPAR ligand or integrin binding. Such antibodies can find use in, for example, decreasing cellular proliferation by binding to uPAR. Cellular signaling effects can be assessed by modulation of (e.g., a decrease in) phosphorylation levels of kinases associated with uPAR signaling, such as extracellular signal-regulated kinases (ERKs), mitogen activated kinases (MAPK), and/or microtubule-associated protein kinase. For example, antibodies of the present disclosure include those that can inhibit uPAR-dependent ERK phosphorylation and in turn, inhibit ERK activation. Antibodies of the present disclosure include those that can inhibit fibronectin-dependent ERK phosphorylation. Antibodies of the present disclosure include those that can facilitate inhibition of proliferation of cells by binding to cell-surface uPAR.

Antibodies of the present disclosure include those that can facilitate a decrease in invasion of uPAR-expressing cells into extracellular matrix and/or facilitate a decrease in adhesion of uPAR-expressing cells (e.g. fibronectin- or vitronecting-dependent adhesion). The ability of cells to invade is a phenotype correlated with the metastatic potential of cancer cells. For example, antibodies in FIG. 1 (e.g. antibodies from clones 2E9, 2G10, and 3C6) facilitate inhibition of cancer cell invasion. Antibodies from clone 3C6 also facilitate a decrease in fibronectin- or vitronectin-dependent cell adhesion. Antibodies of the present disclosure include those that can find use in reducing migration of uPAR-expressing cancer cells.

Amino Acid Sequences

UPAR binding agents of the present disclosure include antibodies that bind an epitope in the ligand-binding region and/or integrin-binding region of uPAR. Several examples of a subject antibody are presented in FIG. 1 and described below.

Antibodies of the present disclosure include antibodies having one, two, or three heavy chain CDRs about 85%, 90%, 95%, 98%, 99%, or 100% identical to $V_H$ CDR1, $V_H$ CDR2, or $V_H$ CDR3, designated as H1, H2, and H3, respectively in FIG. 1. Antibodies of the present disclosure include antibodies having one, two, or three light chain CDRs about 85%, 90%, 95%, 98%, 99%, or 100% identical to $V_L$ CDR1, $V_L$ CDR2, or $V_L$ CDR3 designated as L1, L2, L3, respectively in FIG. 1. All CDRs may be derived from the same antibody or be independently selected from different antibodies listed in FIG. 1 and/or described below.

The $V_H$ and $V_L$ CDRs are separated by framework regions (FR). Amino acid sequences for FRs are exemplified by the FRs of the uPAR antibodies disclosed herein. uPAR antibodies include those containing FRs or other linkers having amino acid sequence that are different from the framework regions disclosed herein. Conservative amino acid substitutions may also be contemplated for any amino acid residue of CDR, framework regions, or linker regions. Other substitutions may be contemplated based on alignments provided in FIG. 1, Panel B.

Optional linkers within a heavy chain or light chain polypeptide of an antibody may comprise amino acid residues or non-peptide polymers. The linkers may have a length of from about 1 to about 100 monomers, e.g., from about 2 to about 5, from about 7 to about 10, from about 10 to about 15, from about 15 to about 20, from about 20 to about 25, from about 25 to about 30, from about 30 to about 50, from about 50 to about 75, or from about 75 to about 100 monomers.

Examples of uPAR antibodies of the present disclosure include an antibody comprising a light chain polypeptide having an amino acid sequence having at least about 85%, at least about 90%, at least about 95%, at least about 98%, or at least about 99%, or 100% amino acid sequence identity to a contiguous stretch of the amino acid sequence set forth as 3C6 $V_L$.

Examples of uPAR antibodies of the present disclosure include an antibody comprising a light chain polypeptide having an amino acid sequence having at least about 85%, at least about 90%, at least about 95%, at least about 98%, or at least about 99%, or 100% amino acid sequence identity to a contiguous stretch of the amino acid sequence set forth as 2E9 $V_L$.

Examples of uPAR antibodies of the present disclosure include an antibody comprising a light chain polypeptide having an amino acid sequence having at least about 85%, at least about 90%, at least about 95%, at least about 98%, or at least about 99%, or 100% amino acid sequence identity to a contiguous stretch of the amino acid sequence set forth as 2G10 $V_L$.

Examples of uPAR antibodies of the present disclosure include an antibody comprising a heavy chain polypeptide having an amino acid sequence having at least about 85%, at least about 90%, at least about 95%, at least about 98%, or at least about 99%, or 100% amino acid sequence identity to a contiguous stretch of the amino acid sequence set forth as 3C6 $V_H$.

Examples of uPAR antibodies of the present disclosure include an antibody comprising a heavy chain polypeptide having an amino acid sequence having at least about 80%, at least about 85%, at least about 90%, at least about 95%, at least about 98%, or at least about 99%, or 100% amino acid sequence identity to a contiguous stretch of the amino acid sequence set forth as 2E9 $V_H$.

Examples of uPAR antibodies of the present disclosure include an antibody comprising a heavy chain polypeptide having an amino acid sequence having at least about 80%, at least about 85%, at least about 90%, at least about 95%, at least about 98%, or at least about 99%, or 100% amino acid sequence identity to a contiguous stretch of the amino acid sequence set forth as 2G10 $V_H$.

Examples of uPAR antibodies of the present disclosure include an antibody comprising a light or a heavy chain polypeptide sequence as depicted in any of the antibodies listed in FIG. 1. Such antibodies can also include any CDRs and framework regions (FRs) as the antibodies listed in FIG. 1.

Examples of uPAR antibodies of the present disclosure include an antibody comprising a light chain polypeptide comprising one or more CDRs (CDR1, CDR2 or CDR3) of the variable region of a light chain polypeptide in FIG. 1 and a heavy chain polypeptide comprising one or more CDRs (CDR1, CDR2, or CDR3) of the variable region of any heavy chain polypeptide in FIG. 1. One or more amino acid residues in one or more of the CDRs set forth above may be deleted, inserted, or substituted in the subject antibody. Conservative substitutions may also be present.

UPAR antibodies of the present disclosure may be of any subclass (e.g. IgG, IgE, IgD, IgA, or IgM). The antibody may be fully human or may be a humanized monoclonal antibody. Chimeric antibodies composed of human and non-human amino acid sequences are also contemplated by the present disclosure. Antibodies of the present disclosure encompass antibodies and antibody fragments that are capable of exhibiting immunological binding properties of the antibodies described herein, e.g., antibodies that compete for binding of an epitope bound by any of the antibodies exemplified herein. Example of antibody fragments include, but are not limited to, Fab, Fab' and $F(ab')_2$, Fd, single-chain Fvs (scFv), single-chain immunoglobulins (e.g., wherein a heavy chain, or portion thereof, and light chain, or portion thereof, are fused), disulfide-linked Fvs (sdFv), diabodies, triabodies, tetrabodies, scFv, affibodies, minibodies, Fab minibodies, and dimeric scFv and any other fragments comprising a $V_L$ and a $V_H$ domain in a conformation such that a specific antigen binding region is formed. Antibody fragments, including single-chain antibodies, may comprise the variable region(s) alone or in combination with the entire or partial of the following: a heavy chain constant domain, or portion thereof, e.g., a CH1, CH2, CH3, transmembrane, and/or cytoplasmic domain, on the heavy chain, and a light chain constant domain, e.g., a $C_{kappa}$ or $C_{lambda}$ domain, or portion thereof on the light chain. Also included in the present disclosure are any combinations of variable region(s) and CH1, CH2, CH3, $C_{kappa}$, $C_{lambda}$, transmembrane and cytoplasmic domains. One or more fragments of the antibody may also be provided as cyclized forms.

The disclosure also provides agents (e.g. antibodies) that are modified by conjugation to a moiety that can provide for a desired characteristic (e.g., increase in serum half-life, anti-cancer activity, etc.). Such antibody conjugates are described in more detail below.

Amino Acid and Nucleic Acid Sequences

UPAR-binding agents can comprise a contiguous amino acid sequence that is at least 80% identical to (e.g., at least 85%, at least 90%, at least 95%, at least 98%, or 100%) to a contiguous sequence of any sequences listed in FIG. 1 and below.

2B3 $V_H$:

(SEQ ID NO: 2)

QLQLQESGGGVVQPGRSLRLSCAASGFTFSSYAMHWVRQAPGKGLEWVAVISYDGSNKYYADS

VKGRFTISRDNSKNTLYLQMNSLRAEDTAVYYCARPYSSSWYSVGNYGIDVWGQGITVTVSSA

STKGPSVFPLAPSSKSTSGGTAALGCLVKDYFPEPVTVSWNSGALTSGVHTFPAVLQSSGLYS

LSSVVTVPSSSLGTQTYICNVNHKPSNTKVDKKVEPKSC

2B3 $V_L$:

(SEQ ID NO: 3)

QAVLTQPSSLSASPGASASLTCTLRRDIDIGTARIYWYQQKPGSPPQYLLNYKSDLYTEKASGVPS

RFSGSKDASANAGILLISGLQSEDEADYYCLIWHNNAWVFGGGTKLTVLGQPKAAPSVTLFPPSS

EELQANKATLVCLISDFYPGAVTVAWKADGSPVKAGVETTKPSKQSNNKYAASSYLSLTPEQW

KSHRSYSCQVTHEGSTVEKTVAPTECS

-continued

2B7 $V_H$:

(SEQ ID NO: 4)

QVQLQQSGPGLVKPSQTLSLTCAISGDSVSSNSAAWNWIRQSPSRGLEWLGRTYYRSKWYNDY

AESVKSRIVINVDTSKNQFSLQLNSVTPEDTAAYYCARDPGGPLDDSFDIWGQGTMVTVSSASTK

GPSVFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSC

2B7 $V_L$:

(SEQ ID NO: 5)

QSVVTQPPSVSGAPGQRVIISCTGSSSNIGAGFDVHWYQQLPGTVPKWYGNTNRPSGVPDRFSG

SKAGTSASLAITGLQAEDEADYYCQAYDDSLQGYVFGTGTKLTVVGQPKANPTVTLFPPSSEEL

QANKATLVCLISDFYPGAVTVAWKADGSPVKAGVETTKPSKQSNNKYAASSYLSLTPEQWKSH

RSYSCQVTHEGSTVEKTVAPTECS

2B8 $V_H$:

(SEQ ID NO: 6)

QVQLQQSGPGLVKPSQTLSLTCAISGDSVSSKSAAWNWIRQSPSRGLEWLGRTYYRSKWYNDY

AVSVKSRITINPDTSKNQFSLQLNSVTPEDTAVYYCARDPGGPLDDSFDIWGQGTMVTVSSASTK

GPSVFPLAPSSKSTSGGTAALGCLVKDYFPEPVTVSWNSGALTSGVHTFPAVLQSSGLYSLSSVV

TVPSSSLGTQTYICYVNHKPSNTKVDKKVEPKSC

2B8 $V_L$:

(SEQ ID NO: 7)

LDVVMTQSPLSLPVTPGEPASISCRSSQSLLRSNGYNYLDWYLQKPGQSPQLLIYLGSTRASGVPD

RFSGSGSGTDFTLKISRVEAEDVGVYYCMQAFQTPLTFGGGTKMEIKRTVAAPSVFIFPPSDEQLK

SGTASVVCLLNNFYPREAKVQWKVDNALQSGNSQESVTEQDSKDSTYSLSSTLTLSKADYEKHK

VYACEVTHQGLSSPVTKSFNRGEC

2B11 $V_H$:

(SEQ ID NO: 8)

QVQLQQSGPGLVKPSQTLSLTCAISGDSVSSNSAAWNWIRQSPSRGLEWLGRTYYRSKWYNDY

AVSVKSRITINPDTSKNQFSLQLNSVTPEDTAVYYCARDSGLGSDYFDYWGQGTLVTVSSASTK

GPSVFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSC

2B11 $V_L$:

(SEQ ID NO: 9)

LDIQMTQSPPSLSASVGDRVTITCQAPHDIKNNLNWYQQKPGKAPKLLIFDASNLETGVPSRFSGS

GSGTNFVLTISSLQPEDIATYYCQQFDDLPLTFGGGTKVDMKRTVAAPSVFIFPPSDEQLESGTAS

VVCLLNNFYPREAKVQWKVDNALQSGNSQESVTEQDSKDSTYSLSSTLTLSKADYEKHKVYAC

EVTHQGLSSPVTKSFNRGEC

2D5 $V_H$:

(SEQ ID NO: 10)

QVQLQQSGPGLVKPSQTLSLTCAISGDSVSSNSAAWNWIRQSPSRGLEWLGRTYYRSKWYNDY

AVSVKSRIIINPDTSKNQFSLQLNSVTPEDTAVYYCARDPGGPLDDSFDIWGQGTMVTVSSASTK

GPSVFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSC

2D5 $V_L$:

(SEQ ID NO: 11)

LDIQLTQSPSTLSASVGDRVTITCRASQTISSSLAWYQQKPGKAPNLLIYKASTLEGGVPSRFSGSG

SGTEFTLTISSLQPEDFATYYCQQSYTTPLTFGGGTKVEIKRTVAAPSVFIFPPSDEQLKSGTASVV

CLLNNFYPREAKVQWKVDNALQSGNSQESVTEQDSKDSTYSLSSTLTLSKADYEKHKVYACEV

THQGLSSPVTKSFNRGEC

-continued

2E7 $V_H$:

(SEQ ID NO: 12)
QVQLQQSGPGLVKPSQTLSLTCAISGDSVSSNSAAWNWIRQSPSRGLEWLGRTYYRSKWYNDY
AVSVKSRIIINPDTSKNQFSLQLNSVTPEDTAVYYCARDPGGPLDDSFDIWGQGTMVTVSSASTK
GPSVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSC

2E7 $V_L$:

(SEQ ID NO: 13)
LDIQLTQSPPSLSASVGDRVTITCQAPHDIKNNLNWYQQKPGKAPKLLIFDASNLETGVPSRFSGS
GSGTNFVLTISSLQPEDIATYYCQQFHDLPLTFGGGTKVDMKRTVAAPSVFIFPPSDEQLKSGTAS
VVCLLNNFYPREAKVQWKVDNALQSGNSQESVTEQDSKDSTYSLSSTLTLSKADYEICHKVYAC
EVTHQGLSSPVTKSFNRGEC

2E9 $V_H$:

(SEQ ID NO: 14)
QVQLQESGGGLVQPGGSLRLSCAASGFTFSSYAMSWVRQAPGKGLEWVSAISGSGGSTYYADS
VKGRETISRDNSKNTLYLQMNSLRAEDTAVYYCAKDEDYDYVWGSYRQYPSRYWGQGTLVTV
SSASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSC

2E9 $V_L$:

(SEQ ID NO: 15)
QSVLTQPPSVSVSPGQTASITCSGDNLGYKYASWYQQKPGQSPVLIIYQDKKRPSGIPERFSGSNS
GNTATLTISGTQAMDEADYYCQAWDSSTSVVFGGGTKLTVLGQPKAAPSVTLFPPSSEELQANK
ATLVCLISDFYPGAVTVAWKADSSPVKAGVETTTPSKQSNNKYAASSYLSLTPEQWKSHRSYSC
QVTHEGSTVEKTVAPTECS

2G10 $V_H$:

(SEQ ID NO: 16)
QVQLQQSGPGLVKPSQTLSLTCAISGDSVSSNSAAWNWIRQSPSRGLEWLGRTYYRSKWYNDY
AVSVKSRIIINPDTSKNQFSLQLNSVTPEDTAVYYCARDPGGPLDDSFDIWGQGTMVTVSSASTK
GPSVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSC

2G10 $V_L$:

(SEQ ID NO: 17)
LDVVMTQSPLSLPVTPGEPASISCRSSQSLLRSNGYNYLDWYLQKPGQSPQLLIYLGSIRASGVPD
RFSGSGSGTDFTLRISRVEAEDVGVYYCMQALQTPFTFGQGTKLEIKRTVAAPSVFIFPPSDEQLK
SGTASVVCLLNNFYPREAKVQWKVDNALQSGNSQESVTEQDSICDSTYSLSSTLTLSKADYEKHK
VYACEVTHQGLSSPVTKSFNRGEC

2G12 $V_H$:

(SEQ ID NO: 18)
EVQLVDTGGGLVQPGGSLRLSCAASGFTFSSYAMSWVRQAPGKGLEWVSAISGSGGSTYYADS
VKGRFTISRDNSKNTLYLQMNSLRAEDTAVYYCAKDWGRNIAVAGTLDYWGQGTLVTVSSAST
KGPSVFPLAPSSKSTSGGTAALGCLVKDYFPEPVTVSWNSGALTSGVHTFPAVLQSSGLYSLSSV
VTYPSSSLGTQTYICNVNHKPSNTKVDKKVEPKSC

2G12 $V_L$:

(SEQ ID NO: 19)
LSYELTQPPSVSVSPGQTASITCSGDKLGQKYVSWYQQRPGQSPLLVIFQDDKRPSGIPERISGSNS
GHTATLTISATQAMDEAEYFCQAWDSNTAPYVFGTGTQVTVLSQPICANPTVTLFPPSSEELQAN
KATLVCLISDFYPGAVTVAWKADGSPVICAGVETTKPSKQSNNKYAASSYLSLTPEQWKSHRSYS
CQVTHEGSTVEKTVAPTECS

-continued

3C6 $V_H$:

(SEQ ID NO: 20)

QVQLQQWGAGLLKPSETLSLTCAVYGGSFSGYYWSWIRQPPGKGLEWIGEINHSGSTNYNPSLK

SRVTISVDTSKNQFSLKLSSVTAADTAVYYCARGRRFGDFDYWGQGTLVTVSSASTKGPSVFPL

APSSKSTSGGTAALGCLVKDYFPEPVTVSWNSGALTSGVHTFPAVLQSSGLYSLSSVVTVPSSSL

GTQTYICNVNHKPSNTKVDKKVEPKSC

3C6 $V_L$:

(SEQ ID NO: 21)

QPVLTQPPSVSVAPGKTARITCGGNNIGSKSVHWYQQKPGQAPVLVVYDDSDRPPGIPERFSGSN

SGNTATLTISRVEAGDEADYYCQVWDSSSDHSPFGTGTKVTVLGQPKANPTVTLFPPSSEELQAN

KATLVCLISDFYPGAVTVAWKADGSPVKAGVETTKPSKQSNNKYAASSYLSLTPEQWKSHRSYS

CQVTHEGSTVEKTVAPTECS

3C7 $V_H$:

(SEQ ID NO: 22)

QVQLQQSGPGLVKPSQTLSLTCAISGDSVSSNSAAWNWIRQSPSRGLEWLGRTYYRSKVVYNDY

AVSVKSRIIINPDTSKNQFSLQLNSVTPEDTAVYYCARDPGGPLDDSFDIWGQGTMVTVSSASTK

GPSVFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSC

3C7 $V_L$:

(SEQ ID NO: 23)

LDIQLTQSPPSLSASVGDRVTITCQAPHDIKNNLNWYQQKPGKAPKLLIFDASNLETGVPSRFSGS

GSGTNFVLTISSLQPEDIATYYCQQFDDLPLTFGGGTKVDMKRTVAAPSVFIFPPSDEQLKSGTAS

VVCLLNNFYPREAKVQWKVDNALQSGNSQESVTEQDSKDSTYSLSSTLTLSKADYEKHEVYAC

EVTHQGLSSPVTKSFNRGEC

3D6 $V_H$:

(SEQ ID NO: 24)

QVQLQQSGPGLVNPSQTLSVTCAISGDSVSSNSAAWNWIRQSPSRGLEWLGRTYYRSKWYNDY

AVSVKSRITIKPDTSKNQFSLQLNSVTPDDTAVYYCARDPGGSLDDSFDIWGQMTVTVSSASTK

GPSVFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSC

3D6 $V_L$:

(SEQ ID NO: 25)

LDIQMTQSPPSLSASVGDRVTITCQAPHDIKNNLNWYQQKPGKAPKLLIFDASNLETGVPSRFSGS

GSGTNFVLTISSLQPEDIATYYCQQFDDLPLTFGGGTKVDMKRTVAAPSVETFPPSDEQLKSGTAS

VVCLLNNFYPREAKVQWKVDNALQSGNSQESVTEQDSKDSTYSLSSTLTLSKADYEKHKVYAC

EVTHQGLSSPVTKSFNRGEC

3H7 $V_H$:

(SEQ ID NO: 26)

QVQLQQSGPGLVKPSQTLSLTCAISGDSVSSNSAAWNWIRQSPSRGLEWLGRTYYRSKWYNDY

AVSVKSRITIKPDTSKNQFSLQLNSVTPDDTAVYYCARDPGGSLDDSFDIWGQGTMVTVSSASTK

GPSVFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSC

3H7 $V_L$:

(SEQ ID NO: 27)

LDVVMTQSPLSLPVTPGEPASISCRSSQSLLRSNGYNYLDWYLQKPGQSPQLLIYLGSTRASGVPD

RFSGSGSGTDFTLKISRVEAEDVGVYYCMQAFQTPLTFGGGTKMEIKRTVAAPSVFIFPPSDEQLK

SGTASVVCLLNNFYPREAKVQWKVDNALQSGNSQESVTEQDSKDSTYSLSSTLTLSKADYEKHK

VYACEVTHQGLSSPVTKSFNRGEC

-continued

4B6 $V_H$:

(SEQ ID NO: 28)

QVQLQQSGPGLVKPSQTLSLTCAISGDSVSSNSAAWNWIRQSPSRGLEWLGRTYYRSKWYNDY

AySVKSRIIINPDTSKNQFSLQLNSVTPEDTAVYYCARDPGGPLDDSYDIWGQGTMVTVSSASTK

GPSVFPLAPSSKSTSGGTAALGCLVKDYFPEPVTVSWNSGALTSGVHTFPAVLQSSGLYSLSSVV

TVPSSSLGTQTYICNVNHKPSNTKVDKKVEPKSC

4B6 $V_L$:

(SEQ ID NO: 29)

LEIVLTQSPLSLPVTPGEPASISCRSSQSLLRSNGYNYLDWYLQKPGQSPQLLIYLGSNRASGVPDR

FSGSGSGTDFTLKISRVEAEDVGVYYCMQAFQTPLTFGGGTKMEIKRTVAAPSVFIFPPSDEQLKS

GTASVVCLLNNFYPREAKVQWKVDNALQSGNSQESVTEQDSKDSTYSLSSTLTLSKADYEKHK

VYACEVTHQGLSSPVTKSFNRGEC

4C1 $V_H$:

(SEQ ID NO: 30)

QVQLVESGGGLVQPGGSLRLSCAASGFTFSSYAMSWVRQAPGKGLEWVSSISASGGSTDYADSV

KGRFTISRDNSKNTLYLQMSSLRAEDTAVYYCVKERPDYDFWSAFDPWGQGTLVTVSSASTKGP

SVFPLAPSSKSTSGGTAALGCLVKDYFPEPVTVSWNSGALTSGVHTFPAVLQSSGLYSLSSVVTV

PSSSLGTQTYICNVNHKPSNTKVDKKVEPKSC

4C1 $V_L$:

(SEQ ID NO: 31)

LDVVMTQSPLSLPVTPGEPASISCRSSQSLLHSNGYNYLDWYLQKPGQSPQLLIYLGSNRASGVP

DRFSGSGSGTDFTLKISRVEAEDVGVYYCMQGTHWPPTFGQGTKLEIKRTVAAPSVFIFPPSDEQ

LKSGTASVVCLLNNFYPREAKVQWKVDNALQSGNSQESVTEQDSKDSTYSLSSTLTLSKADYEK

HKLYACEVTHQGLSSPVTKSFNRGEC

Where the agent is an IgG antibody, the $V_H$ of the IgG may contain an additional Fc region at the C-terminus. The Fc region may comprise a contiguous amino acid sequence that is at least 80% identical to (e.g., at least 85%, at least 90%, at least 95%, at least 98%, or 100%) to a contiguous sequence of (SEQ ID NO: 32)

LLAPSSKSTSGGTAALGCLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVFLFPPKPKDTLMISRTPE

VTCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYTQKSLSLSPGK.

Certain CDRs are listed separately in the table below. Other CDRs can be found in FIG. 1, panel B.

TABLE 1

Complementarity determining regions of 3C6 and 2G10 according to the Kabat database.

| | 3C6 | 2G10 |
|---|---|---|
| **Light Chain** | | |
| CDR1 | GGNNIGSKSVH (SEQ ID NO: 33) | RSSQSLLRSNGYNYLD (SEQ ID NO: 34) |
| CDR2 | DDSDRPP (SEQ ID NO: 35) | LGSIRAS (SEQ ID NO: 36) |
| CDR3 | QVWDSSSDHSP (SEQ ID NO: 37) | MQALQTPFT (SEQ ID NO: 38) |
| **Heavy Chain** | | |
| CDR1 | GGSFSGYYWSW (SEQ ID NO: 39) | GDSVSSNSAAWN (SEQ ID NO: 40) |
| CDR2 | EINHSGSTNYNPSLKS (SEQ ID NO: 41) | RTYYRSKWYNDYAVSVKS (SEQ ID NO: 42) |

TABLE 1-continued

Complementarity determining regions of 3C6 and 2G10 according to the Kabat database.

| | 3C6 | 2G10 |
|---|---|---|
| CDR3 | GRRFGDFDY (SEQ ID NO: 43) | DPGGPLDDSFDI (SEQ ID NO: 44) |

Recombinant Antibody

The agents of the present disclosure may be an antibody produced by recombinant methods. Such antibodies can be produced by expression of a polynucleotide having a nucleotide sequence encoding a polypeptide that is at least 80% identical to (e.g., at least 85%, at least 90%, at least 95%, at least 98%) to a contiguous sequence of any antibody listed in FIG. 1 and/or of any sequence listed above. The percent identity of nucleic acids is based on the shorter of the sequences compared. Well known programs such as BLASTN (2.0.8) (Altschul et al. (1997) *Nucl. Acids. Res.* 25:3389-3402) using default parameters and no filter may be employed to make a sequence comparison. Examples of nucleic acids encoding the antibodies of the present disclosure are discussed later below.

Methods for producing recombinant antibodies are known in the art. For example, the nucleic acids encoding the antibody, or at least a CDR of a heavy chain polypeptide or at least a CDR of a light chain polypeptide, are introduced directly into a host cell, and the cell incubated under conditions sufficient to induce expression of the encoded antibody. The recombinant antibody may be glycosylated by an endogenous glycosyl-transferase in the host cells, unglycosylated, or may have an altered glycosylation pattern.

Recombinant antibodies include chimeric antibodies. Chimeric antibodies are immunoglobulin molecules comprising human and non-human portions. More specifically, the antigen combining region (or variable region) of a humanized chimeric antibody is derived from a non-human source (e.g. murine), and the constant region of the chimeric antibody (which confers biological effector function to the immunoglobulin) is derived from a human source. The chimeric antibody can have the antigen binding specificity of the non-human antibody molecule and the effector function conferred by the human antibody molecule. A large number of methods of generating chimeric antibodies are well known to those of skill in the art. An alternative approach is the generation of humanized antibodies by linking the CDR regions of non-human antibodies to human constant regions by recombinant DNA techniques. See Queen et al., *Proc. Natl. Acad. Sci. USA* 86: 10029-10033 (1989).

Human Antibodies

The uPAR-binding agent may be a fully human antibody. Human antibodies are primarily composed of characteristically human polypeptide sequences. A subject human antibody can be produced by a wide variety of methods (see, e.g., Larrick et al., U.S. Pat. No. 5,001,065). Human antibodies may be derived from a fully human Fab phage display library, as described in de Haard et al. (1999) *Journal of Biological Chemistry.* 274, 18218-18230

Human antibodies can also be produced initially in trioma cells (descended from three cells, two human and one mouse). Genes encoding the antibodies are then cloned and expressed in other cells, particularly non-human mammalian cells. The general approach for producing human antibodies by trioma technology has been described by Ostberg et al. *Hybridoma* 1983, 2: 361-367, Ostberg, U.S. Pat. No. 4,634,664, and Engelman et al., U.S. Pat. No. 4,634,666. Triomas have been found to produce antibody more stably than ordinary hybridomas made from human cells. Accordingly, the present disclosure contemplates a DNA molecule comprising a nucleic acid sequence encoding an antibody that binds to uPAR (e.g. a nucleic acid encoding 2E9, 2G10, or 3C6). Nucleic acid sequences will be described later below.

Conjugates uPAR-binding agents of the present disclosure can be modified by chemical conjugation to a moiety of interest. For example, an agent may be conjugated to a second molecule of a different type (e.g. nucleic acid to a non-nucleic acid, or a peptide to a non-peptide). Where the agent is an antibody, the antibody conjugated to a second molecule is referred to as an "antibody conjugate." A subject antibody conjugate may be useful for modifying the growth of cells, particularly cancer cells. The compositions containing the agents can encompass aggregates of conjugates, as they are readily taken up by cells.

Conjugated agents retain a desired activity, while exploiting properties of the second molecule of the conjugate to impart an additional desired characteristic. For example, a subject agent (e.g. antibody) can be conjugated to a second molecule that aids in solubility, storage or other handling properties, cell permeability, half-life, controls release and/or distribution such as by targeting a particular cell (e.g., neurons, leucocytes etc.) or cellular location (e.g., lysosome, endosome, mitochondria etc.), tissue or other bodily location (e.g., blood, neural tissue, particular organs etc.). Other examples include the conjugation of a dye, fluorophore or other detectable labels or reporter molecules for assays, tracking and the like. More specifically, a subject antibody can be conjugated to a second molecule such as a peptide, polypeptide, dye, fluorophore, luciferase, nucleic acid, carbohydrate, lipid and the like, such as the attachment of a lipid moiety, including N-fatty acyl groups such as N-lauroyl, N-oleoyl, fatty amines such as dodecyl amine, oleoyl amine, and the like.

The present disclosure further provides a conjugated agent that comprises a moiety that modifies cellular uptake relative to unconjugated material. The conjugate may exhibit increased cellular uptake relative to unconjugated material. In alternative embodiments, the conjugate exhibits decreased cellular uptake relative to unconjugated material. In this aspect, the efficiency of cellular uptake can be increased or decreased by linking to small organic or inorganic molecules, polymers, peptides or proteins that facilitate, or inhibit endocytosis. For example, a given antibody can be linked to a ligand for a target receptor or large molecule that is more easily engulfed by endocytotic mechanisms, such as another antibody. The antibody or other ligand can then be internalized by endocytosis and the payload released by acid hydrolysis or enzymatic activity when the endocytotic vesicle fuses with lysosomes. As such, the conjugate may be one that increases endocytosis relative to unconjugated agent. To decrease cellular uptake, the conjugate can include a ligand that retains the antibody on the surface of a cell, which can be useful as a control for cellular uptake, or in some instances decrease uptake in one cell type while increasing it in others.

Other features of a conjugated agent may include one where the conjugate reduces toxicity relative to unconjugated agent. Another feature is that the conjugate may target a cancer cell more efficiently than an unconjugated material. Additional examples include an antibody of the present disclosure conjugated with one or more molecules that complement, potentiate, enhance or can otherwise operate synergistically in connection with the antibody of the present disclosure. For instance, where the agent is an antibody, the antibody can optionally have attached an anti-cancer drug for delivery to a site of a cancer or bacterial cell to further facilitate cell killing or clearance, e.g., an anti-proliferation moiety (e.g., VEGF antagonist, e.g., an anti-VEGF antibody or aptamer), a toxin (e.g., an anti-cancer toxin, e.g., ricin, *Pseudomonas* exotoxin A, and the like), radionuclide (e.g. 90Y, 131I, 177L, 10B for boron neutron capture, and the like), anti-cancer drugs (e.g. doxorubicin, calicheamicin, maytansinoid DM1, auristatin caupecitabine, 5-fluorouricil, leucovorin, irinotercan, and the like), and/or can optionally be modified to provide for improved pharmacokinetic profile (e.g., by PEGylation, hyperglycosylation, and the like).

The present disclosure contemplates uPAR-binding agents to encompass recombinant fusion antibody that is modified to include a heterologous protein, i.e., is linked to a polypeptide that is not part of the antibody derived from a clone. For example, a 3C6 heavy chain polypeptide or 2G10 light chain polypeptide, a 2E9 antibody fragment, or any combination thereof may be joined to a reporter protein or to a protein having a desired anti-cancer effect. The reporter protein may be a fluorescent protein or a luciferase. The antibody may also be conjugated to a second antibody (or at least an antigen-binding portion thereof), e.g., an antibody that specifically binds an angiogenic or proliferative factor, such as an antibody that is directed against vascular enthothelial growth factor (VEGF), which is key mediator of angiogenesis, where the antibody targets the conjugate to specific cancer cells and the anti-VEGF antibody inactivates VEGF thus inhibiting angiogenesis. Methods for producing a fusion protein of interest when provided a nucleic acid sequence are well known in the art.

UPAR-binding agents may also be detectably labeled, either directly or indirectly. Direct labels include radioisotopes (e.g., $^{125}$I; $^{35}$S, $^{111}$In, $^{99m}$Tc, and the like); enzymes whose products generate a signal (e.g., luciferase, β-galactosidase, horse radish peroxidase, alkaline phosphatase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins; or MRI contrast agents and the like. Indirect labels include second antibodies specific for a subject antibody, wherein the second antibody is labeled as described above; and members of specific binding pairs, e.g., biotin-avidin, and the like.

Polyethylene Glycol (PEG)-Modified Antibodies

Examples of conjugates include agents (e.g. antibodies) modified to contain one or more poly(ethylene glycol) (PEG) moieties. Such antibodies are referred to as "PEGylated agents." Wherein the agent is an antibody, the antibodies include PEGylated antibodies, e.g., PEGylated recombinant antibodies that bind specifically to uPAR. Methods and reagents suitable for PEGylation of an antibody are well known in the art. In general, PEG suitable for conjugation to an antibody is generally soluble in water at room temperature, and has the general formula $R(O—CH_2—CH_2)_nO—R$, where R is hydrogen or a protective group such as an alkyl or an alkanol group, and where n is an integer from 1 to 1000. Where R is a protective group, it generally has from 1 to 8 carbons.

The PEG may have at least one hydroxyl group modified to generate a functional group that is reactive with an amino group, e.g., an epsilon amino group of a lysine residue, a free amino group at the N-terminus of a polypeptide, or any other amino group such as an amino group of asparagine, glutamine, arginine, or histidine.

PEG may also be derivatized so that it is reactive with free carboxyl groups in the antibody polypeptide. Suitable derivatives of PEG that are reactive with the free carboxyl group at the carboxyl-terminus of a heavy chain or light chain polypeptide include, but are not limited to PEG-amine, and hydrazine derivatives of PEG (e.g., PEG-NH—$NH_2$).

Additional derivatives of PEG comprises a terminal thiocarboxylic acid group, —COSH, which selectively reacts with amino groups to generate amide derivatives. In other embodiments, the PEG comprises a reactive ester such as an N-hydroxy succinimidate at the end of the PEG chain. Such an N-hydroxysuccinimidate-containing PEG molecule reacts with select amino groups at particular pH conditions such as neutral 6.5-7.5.

The PEG can be conjugated directly to an amino acid residue of the antibody, or through a linker. In some embodiments, a linker is added to an antibody polypeptide, forming a linker-modified antibody polypeptide. Such linkers provide various functionalities, e.g., reactive groups such sulfhydryl, amino, or carboxyl groups to couple a PEG reagent to the linker-modified antibody polypeptide. The PEG may be conjugated to the antibody polypeptide is linear. In other embodiments, the PEG conjugated to the antibody polypeptide is branched. Branched PEG derivatives such as those known in the art, e.g., "star-PEG's" and multi-armed PEG's.

Pharmaceutical Compositions

The present disclosure provides pharmaceutical compositions containing one or more uPAR-binding agents (e.g. antibodies). The compositions of the present disclosure encompass those that contain more than one type of agents (e.g. antibodies). The composition may contain at least two, at least three, at least four or more different types of agents (e.g. antibodies). Where the agents in the subject compositions are antibodies, the antibodies may differ in their amino acid sequence, modification by conjugation, affinity, epitopes of uPAR bound, and/or effects on cell signaling mediated by uPAR. For example, the composition may contain a first antibody that competes with integrins (e.g. β1 integrins) binding to uPAR and a second antibody that competes with urokinase for binding to uPAR. Alternatively, a composition may contain a first antibody that binds to uPAR and competes with urokinase binding to uPAR and a second antibody that binds to uPAR and competes with urokinase binding to uPAR and does or does not compete with the binding of the first antibody. An example of a composition with combined antibodies is one that contains both antibodies from clone 3C6 and antibodies from clone 2G10 and/or 2E9.

In a related example, the composition can contain a first binding agent (e.g. anti-uPAR antibody) that inhibits a first uPAR signaling pathway; and a second binding agent (e.g. anti-uPAR antibody) inhibits a second uPAR signaling pathway. The different signaling pathways of uPAR affected by the one or more binding agents may cross-talk. "Cross-talk" as used herein, refers to different signaling pathways in which one or more signal components are shared, such that a signal inducing condition can activate multiple responses and/or signaling pathways. A subject composition containing one or more agents that inhibit one or more signaling pathways can synergistically inhibit cell adhesion, proliferation, and/or migration of cancer cells. For example, one signaling pathway that can be inhibited by a binding agent is mediated by uPA binding to uPAR, while another pathway is mediated by integrin (e.g. a β1 integrin) binding to uPAR.

Other agents that may be included in the subject compositions include agents useful for treating a condition. For example, combination therapies discussed later below may use subject compositions containing one or more drug in addition to the one or more subject antibodies.

Pharmaceutical compositions can include a pharmaceutically acceptable excipient, which can be a solution such as an aqueous solution (e.g., a saline solution). The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

An antibody of the present disclosure can be formulated for parenteral administration for use in the methods described below. Where an antibody is administered as a liquid injectable (such as in those embodiments where they are administered intravenously, intraarterially, or directly into a tissue), an antibody formulation may be provided as a ready-to-use dosage form, or as a reconstitutable storage-stable powder or liquid composed of pharmaceutically acceptable carriers and excipients.

Pharmaceutical compositions can also contain one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

The concentration of an agent (e.g. antibody) in the pharmaceutical formulations can vary from less than about 0.1%, usually at or at least about 2% to as much as 20% to 50% or more by weight, and will be selected primarily by fluid volumes, viscosities, etc., in accordance with the particular mode of administration selected and the patient's needs. The resulting compositions may be in the form of a solution, suspension, tablet, pill, capsule, powder, gel, cream, lotion, ointment, aerosol or the like.

Compositions of the present disclosure can include a therapeutically effective amount of a subject agent (e.g. antibody), as well as any other compatible components, as needed. By "therapeutically effective amount" is meant that the administration of that amount to an individual, either in a single dose, as part of a series of the same or different antibody or compositions, is effective to provide a desired effect (e.g., inhibition of cell proliferation). The therapeutically effective amount can be adjusted in connection with dosing regimen and diagnostic analysis of the subject's condition (e.g., monitoring for the present or absence of a cell surface epitopes using an antibody specific for uPAR) and the like.

The amount of composition administered to an animal, e.g., a human, in the context of the present disclosure should be sufficient to effect a prophylactic or therapeutic response in the animal over a reasonable time frame, and varies depending upon the goal of the administration, the health and physical condition of the individual to be treated, age, the degree of resolution desired, the formulation of the antibody composition, the treating clinician's assessment of the medical situation, and other relevant factors. One skilled in the art will also recognize that dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound. Thus it is expected that the amount will fall in a relatively broad range, but can nevertheless be routinely determined through various features of the subject such as those features noted above.

Also, suitable doses and dosage regimens can be determined by comparisons to anticancer agents that are known to affect the desired growth inhibitory response. Such dosages include dosages which result in the low dose inhibition of cell growth, without significant side effects. In proper doses and with suitable administration of certain compounds, the compounds of the present disclosure can provide for a wide range of intracellular effects, e.g., from partial inhibition to essentially complete inhibition of cell growth. Dosage treatment may be a single dose schedule or a multiple dose schedule (e.g., including ramp and maintenance doses). As indicated below, a subject composition may be administered in conjunction with other agents, and thus doses and regiments can vary in this context as well to suit the needs of the subject.

Methods of Production

Wherein the agent is an antibody, the antibodies can be prepared using a wide variety of techniques known in the art including the use of hybridoma, recombinant, and phage display technologies, or a combination thereof. For example, antibody may be made from *E. coli* or mammalian cells containing expression cassettes encoding whole antibodies or Fabs. The antibody may also be isolated from hybridoma cells derived from an animal host immunized with an immunogenic composition containing uPAR.

Anti-uPAR antibodies, including antigen binding fragments of anti-uPAR antibodies, may also be produced by genetic engineering. Where the protein is produced using recombinant techniques, the proteins may be produced as an intracellular protein or as an secreted protein, using any suitable construct and any suitable host cell, which can be a prokaryotic or eukaryotic cell, such as for example a bacterial (e.g. *E. coli*) or a yeast host cell, respectively.

Examples of eukaryotic cells that may be used as host cells include yeast cells, insect cells, mammalian cells, and/or plant cells. Where mammalian host cells are used, the cells may include one or more of the following: human cells (e.g. Hela, 293, H9 and Jurkat cells); mouse cells (e.g., NIH3T3, L cells, and C127 cells); primate cells (e.g. Cos 1, Cos 7 and CV1) and hamster cells (e.g., Chinese hamster ovary (CHO) cells).

Vectors, each containing one heavy chain gene and one light chain gene retaining the initial antigen specificity, may be produced by insertion of appropriate sections of the nucleic acids encoding the antibodies into the expression vectors. A library of clones which co-express a heavy and light chain (comprising for example an intact antibody, an Fab fragment or an antigen binding fragment of an antibody molecule) can also be generated. The vectors that carry these genes may be co-transfected into a host (e.g. bacteria, insect cells, mammalian cells, or other suitable protein production host cell). Alternatively, the heavy and light chain may be inserted into a single vector and transfected into a host (e.g. bacteria, insect cells, mammalian cells, or other suitable protein production host cell).

Methods for introduction of genetic material into host cells include, for example, transformation, electroporation, conjugation, calcium phosphate methods, cationic peptide-based methods, polyethyleneimine-based methods, and the like. The method for transfer can be selected so as to provide for stable expression of the introduced antibody-encoding nucleic acid, such as by for example allowing selection for an antibiotic resistance marker (e.g. using gentimycin, ampicillin, kanamycin, G418 and the like), or a metabolism marker (e.g. selection for glutamine synthesis in glutamine free medium with or without methionine sulfoximine, or selection for DHFR with or without methotrexate). The antibody-encoding nucleic acid can be provided as an inheritable episomal element (e.g., plasmid) or can be genomically integrated. A variety of appropriate vectors for use in production of an antibody of interest are available commercially. When antibody gene synthesis is induced in the transfected host, the heavy and light chain proteins self-assemble to produce active antibodies that can be detected by assaying binding with the antigen or immunogen and isolated using techniques known in the art.

Further examples of techniques which can be used to produce single-chain Fvs and other antibodies include those described in Huston et al., *Methods in Enzymology* 1991, 203:46-88; and Skerra et al. (1988) *Science* 240:1038-1040. Antibodies can be humanized using a variety of techniques known in the art, veneering or resurfacing, and chain shuffling. Isolation and purification of antibodies can be accomplished using techniques known in the art, and can provide for antibody-containing preparations at least 50% to 60%, by weight, free from organic molecules with which the antibody is naturally associated or with which it is associated during manufacture.

Nucleic Acid

The present disclosure contemplates cells expressing a uPAR antibody as disclosed herein, e.g., by expression of heavy and light chain-encoding, or heavy and light chain fragment encoding, expression cassettes. Examples of encoding nucleic acids include a nucleic acid encoding a polypeptide comprising one or more CDRs at least about 85%, 90%, 95%, 98%, 99%, or 100% identical to those CDRs depicted in FIG. 1. In another example, the antibody has one or more light and heavy chain complementarity determining region (CDR) polypeptide sequences at least about 85%, 90%, 95%, 98%, 99%, or 100% identical to those light and heavy chain CDR polypeptide sequences depicted in FIG. 1.

An example of nucleic acid sequence encoding a heavy chain of an antibody that binds to uPAR includes SEQ ID NO:\\ and NO:\\. An example of nucleic acid sequence encoding a light chain of an antibody that binds to uPAR includes SEQ ID NO:\\ and NO:\\. The disclosure further contemplates recombinant host cells containing an exogenous polynucleotide encoding at least a CDR of a heavy chain polypeptide or at least a CDR of a light chain polypeptide of the subject antibody.

Wherein the subject agents are encoded by a nucleic acid (e.g. to produce a recombinant antibody), the nucleic acid can comprise a contiguous nucleic acid sequence that is at least 80% identical to (e.g., at least 85%, at least 90%, at least 95%, at least 98%, or 100%) to a contiguous sequence of any sequences listed below.

1A8 $V_H$:

(SEQ ID NO: 45)

```
GCCCAGGTACAGCTGCAGCAGTCAGGTCCAGGACTGGTGAAGCCCTCGCAGACCCTCTCACT

CACCTGTGCCATCTCCGGGGACAGTGTCTCTAGCAACAGTGCTGCTTGGAACTGGATCAGGC

AGTCCCCATCGAGAGGCCTTGAGTGGCTGGGAAGGACATACTACAGGTCCAAGTGGTATAA

TGATTATGCAGTATCTGTGAAAAGTCGAATAACCATCAACCCAGACACATCCAAGAACCAGT

TCTCCCTGCAGCTGAACTCTGTGACTCCCGAGGACACGGCTGTGTATTACTGTACAAGAGAT

CCGGGGGGGGCTCTCGATGATAGTTTTGATATCTGGGGCCAAGGGACAATGGTCACCGTCTC

AAGCGCCTCCACCAAGGGCCCATCGGTCTTCCCCCTGGCACCCTCCTCCAAGAGCACCTCTG

GGGGCACAGCGGCCCTGGGCTGCCTGGTCAAGGACTACTTCCCCGAACCGGTGACGGTGTC

GTGGAACTCAGGCGCCCTGACCAGCGGCGTCCACACCTTCCCGGCTGTCCTACAGTCCTCAG

GACTCTACTCCCTCAGCAGCGTAGTGACCGTGCCCTCCAGCAGCTTGGGCACCCAGACCTAC

ATCTGCAACGTGAATCACAAGCCCAGCAACACCAAGGTGGACAAGAAAGTTGAGCCCAAAT

CTTGT
```

1A8 $V_L$:

(SEQ ID NO: 46)

```
CTTGATGTTGTGATGACTCAGTCTCCAGCCTCCCTGTCTGTATCTGTAGGAGACAGAGTCACC

CTCACTTGCCAGGCGAGTCAGGTCATTAACAACCACTTAAATTGGTATCAACAACAACCAGG

GAAAGCCCCTAAGCTCCTGGTCTACGATGCATCCAATCTGGAAACAGGGGTCCCATCAAGGT

TCAGTGGAAGTGGATCTGGGACAGATTTTACTTTCACCATCAGCGGCCTGCAGCCTGAAGAT

ATTGCAACATATTACTGTCAACAGTCTGATAATCTCCCGCTCACTTTCGGCGGAGGGACCAA

GCTAGAGATCAAACGAACTGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGAGAGTGTCACAG

AGCAGGACAGCAAGGACAGCACCTACAGCCTCAGCAGCACCCTGACGCTGAGCAAAGCAGA

CTACGAGAAACACAAAGTCTACGCCTGCGAAGTCACCCATCAGGGCCTGAGCTCGCCCGTC

ACAAAGAGCTTCAACAGGGGAGAGTGT
```

-continued

1D5 $V_H$:

(SEQ ID NO: 47)
CAGGTACAGCTGCAGCAGTCAGGTCCAGGACTGGTGAAGCCCTCGCAGACCCTCTCACTCAC
CTGCGCCATCTCCGGGGACAGTGTCTCTAGCAACAGTGCTGCTTGGAACTGGATCAGGCAGT
CCCCATCGAGAGGCCTTGAGTGGCTGGGAAGGACATATTACAGGTCCAAGTGGTATAATGA
TTATGCAGAATCTGTGAAAAGTCGAATAGTCATCAACGTAGACACATCCAAGAACCAGTTCT
CCCTGCAGTTGAACTCTGTGACTCCCGAGGACACGGCTGTGTATTACTGTGCAAGAGATCCG
GGGGGGCCTCTCGATGATAGTTTTGATATCTGGGGCCAAGGGACAATGGTCACCGTCTCAAG
CGCCTCCACCAAGGGCCCATCGGTCTTCCCCCTGGCACCCTCCTCCAAGAGCACCTCTGGGG
GCACAGCGGCCCTGGGCTGCCTGGTCAAGGACTACTTCCCCGAACCGGTGACGGTGTCGTGG
AACTCAGGCGCCCTGACCAGCGGCGTCCACACCTTCCCGGCTGTCCTACAGTCCTCAGGACT
CTACTCCCTCAGCAGCGTAGTGACCGTGCCCTCCAGCAGCTTGGGCACCCAGACCTACATCT
GCAACGTGAATCACAAGCCCAGCAACACCAAGGTGGACAAGAAAGTTGAGCCCAAATCTTG
T

1D5 $V_L$:

(SEQ ID NO: 48)
CTTGAAATTGTGATGACACAGTCTCCAGTCTCCCTGCCCGTCACCCCTGGAGAGCCGGCCTC
CATCTCCTGCAGGTCTAGTCAGAGCCTCCTGCGTAATAATGGATACAACTATTTGGATTGGT
ACCTGCAGAAGCCAGGGCAGTCTCCACAGCTCCTGATCTATTTGGGTTCTAATCGGGCCTCC
GGGGTCCCTGACAGGTTCAGTGGCAGTGGATCAGGCACAGATTTTACACTGAAAATCAGCA
GAGTGGAGGCTGAGGATGTTGGGGTTTATTACTGCATGCAAGCTCTACAAACTCCATTCACT
TTCGGCCCTGGGACCAAAGTGGATATCAAACGAACTGTGGCTGCACCATCTGTCTTCATCTT
CCCGCCATCTGATGAGCAGTTGAAATCTGGAACTGCCTCTGTTGTGTGCCTGCTGAATAACTT
CTATCCCAGAGAGGCCAAAGTACAGTGGAAGGTGGATAACGCCCTCCAGTCGGGTAACTCC
CAGGAGAGTGTCACAGAGCAGGACAGCAAGGACAGCACCTACAGCCTCAGCAGCACCCTGA
CGCTGAGCAAAGCAGACTACGAGAAACACAAAGTCTACGCCTGCGAAGTCACCCATCAGGG
CCTGAGCTCGCCCGTCACAAAGAGCTTCAACAGGGGAGAGTGT

1F6 $V_H$:

(SEQ ID NO: 49)
CAGGTACAGCTGCAGCAGTCAGGTCCAGGACTGGTGAAGCCCTCGCAGACCCTCTCACTCAC
CTGTGCCATCTCCGGGGACAGTGTCTCTAGCAACAGTGCTGCTTGGAACTGGATCAGGCAGT
CCCCATCGAGAGGCCTTGAGTGGCTGGGAAGGACATACTACAGGTCCAAGTGGTATAATGA
TTATGCAGTATCCGTGAAAAGTCGAATAATTATCAACCCAGACACATCCAAGAACCAGTTCT
CCCTGCAGCTGAACTCTGTGACTCCCGAGGACACGGCTGTGTATTACTGTGCAAGAGATCCG
GGGGGGCCTCTCGATGATAGTTTTGATATCTGGGGCCAAGGGACAATGGTCACCGTCTCAAG
CGCCTCCACCAAGGGCCCATCGGTCTTCCCCCTGGCACCCTCCTCCAAGAGCACCTCTGGGG
GCACAGCGGCCCTGGGCTGCCTGGTCAAGGACTACTTCCCCGAACCGGTGACGGTGTCGTGG
AACTCAGGCGCCCTGACCAGCGGCGTCCACACCTTCCCGGCTGTCCTACAGTCCTCAGGACT
CTACTCCCTCAGCAGCGTAGTGACCGTGCCCTCCAGCAGCTTGGGCACCCAGACCTACATCT
GCTACGTGAATCACAAGCCCAGCAACACCAAGGTGGACAAGAAAGTTGAGCCCAAATCTTG
T

-continued

1F6 $V_L$:

(SEQ ID NO: 50)

CTTGATGTTGTGATGACTCAGTCTCCACTCTCCCTGCCCGTCACCCCTGGAGAGCCGGCCTCC

ATCTCCTGCAGGTCTAGTCAGAGCCTCCTGCGTAGTAATGGATACAACTATTTGGATTGGTA

CCTGCAGAAGCCAGGGCAGTCTCCACAGCTCCTGATCTATTTGGGTTCTATTCGGGCCTCCG

GGGTCCCTGACAGGTTCAGTGGCAGTGGATCGGGCACAGATTTTACACTGAGAATTAGCAG

AGTGGAGGCTGAGGATGTTGGGGTTTATTACTGCATGCAAGCTCTACAAACCCCGTTCACTT

TTGGCCAGGGGACCAAGCTGGAGATCAAGCGAACTGTGGCTGCACCATCTGTCTTCATCTTC

CCGCCATCTGATGAGCAGTTGAAATCTGGAACTGCCTCTGTTGTGTGCCTGCTGAATAACTTC

TATCCCAGAGAGGCCAAAGTACAGTGGAAGGTGGATAACGCCCTCCAATCGGGTAACTCCC

AGGAGAGTGTCACAGAGCAGGACAGCAAGGACAGCACCTACAGCCTCAGCAGCACCCTGAC

GCTGAGCAAAGCAGACTACGAGAAACACAAAGTCTACGCCTGCGAAGTCACCCATCAGGGC

CTGAGCTCGCCCGTCACAAAGAGCTTCAACAGGGGAGAGTGT

1G9 $V_H$:

(SEQ ID NO: 51)

CAGGTGCAGCTGCAGGAGTCCGGCCCAGGACTGGTGAAGCCTTCGGAGACCCTGTCCCTCAC

CTGCACTGTCTCTGGTGGCTCCATCAGCAGTAGTAGTTACTACTGGGGCTGGATCCGCCAGC

CCCCAGGGAAGGGGCTGGAGTGGATTGGGAGTATCTATTATAGTGGGAGCACCTACTACAA

CCCGTCCCTCAAGAGTCGAGTCACCATATCCGTAGACACGTCCAAGAACCAGTTCTCCCTGA

AGCTGACCTCTGTGACCGCCGCAGACACGGCTGTGTATTACTGTGCGAGACTAAACGCCCAC

CCGATTTACTACTACTACTACGGTATGGACGTCTGGGGCCAAGGGACCACGGTCACCGTCTC

AAGCGCCTCCACCAAGGGCCCATCGGTCTTCCCCCTGGCACCCTCCTCCAAGAGCACCTCTG

GGGGCACAGCGGCCCTGGGCTGCCTGGTCAAGGACTACTTCCCCGAACCGGTGACGGTGTC

GTGGAACTCAGGCGCCCTGACCAGCGGCGTCCACACCTTCCCGGCTGTCCTACAGTCCTCAG

GACTCTACTCCCTCAGCAGCGTAGTGACCGTGCCCTCCAGCAGCTTGGGCACCCAGACCTAC

ATCTGCAACGTGAATCACAAGCCCAGCAACACCAAGGTGGACAAGAAAGTTGAGCCCAAAT

CTTGT

1G9 $V_L$:

(SEQ ID NO: 52)

CTTGAAATTGTGCTGACTCAGTCTCCAGGCACCCTGTCTTTGTCTCCAGGGGAAAGAGCCAC

CCTCTCCTGCAGGGCCAGTCAGAGTGTTAGCAGCTACTTAGCCTGGTACCAACAGAAACCTG

GCCAGGCTCCCAGGCTCCTCATCTATGATGCATCCAACAGGGCCACTGGCATCCCAGCCAGG

TTCAGTGGCAGTGGGTCTGGGACAGACTTCACTCTCACCATCAGCAGCCTAGAGCCTGAAGA

TTTTGCAGTTTATTACTGTCAGCAGCGTAGCAACTGGCCTCCGATGTACACTTTTGGCCAGGG

GACCAAGCTGGAGATCAAACGAACTGTGGCTGCACCATCTGTCTTCATCTTCCCGCCATCTG

ATGAGCAGTTGAAATCTGGAACTGCCTCTGTTGTGTGCCTGCTGAATAACTTCTATCCCAGA

GAGGCCAAAGTACAGTGGAAGGTGGATAACGCCCTCCAATCGGGTAACTCCCAGGAGAGTG

TCACAGAGCAGGACAGCAAGGACAGCACCTACAGCCTCAGCAGCACCCTGACGCTGAGCAA

AGCAGACTACGAGAAACACAAAGTCTACGCCTGCGAAGTCACCCATCAGGGCCTGAGCTCG

CCCGTCACAAAGAGCTTCAACAGGGGAGAGTGT

2B1 $V_H$:

(SEQ ID NO: 53)

CAGGTACAGCTGCAGCAGTCAGGTCCAGGACTGGTGAAGCCCTCGCAGACCCTCTCACTCAC

CTGTGCCATCTCCGGGGACAGTGTCTCTAGTAACAGTGCTGCTTGGAACTGGATCAGGCAGT

CCCCATCGAGAGGCCTTGAGTGGCTGGGGAGGACATACTACAGGTCCAAGTGGTATTATGAT

-continued

TATGCAGTCTCTGTGAAAGGTCGAATAACCTTCACCCCAGACACATCCAAGAACCAGGTCTC

CCTGCACCTGAACGCTGTGACTCCCGAGGACACGGCTATGTATTACTGTGCAAGAGATCCGG

GGGGGCCTCTCGATGATAGTTTTGATATCTGGGGCCAAGGGACAATGGTCACCGTCTCAAGC

GCCTCCACCAAGGGCCCATCGGTCTTCCCCCTGGCACCCTCCTCCAAGAGCACCTCTGGGGG

CACAGCGGCCCTGGGCTGCCTGGTCAAGGACTACTTCCCCGAACCGGTGACGGTGTCGTGGA

ACTCAGGCGCCCTGACCAGCGGCGTCCACACCTTCCCGGCTGTCCTACAGTCCTCAGGACTC

TACTCCCTCAGCAGCGTAGTGACCGTGCCCTCCAGCAGCTTGGGCACCCAGACCTACATCTG

CAACGTGAATCACAAGCCCAGCAACACCAAGGTGGACAAGAAAGTTGAGCCCAAATCTTGT

2B1 $V_L$:

(SEQ ID NO: 54)

CTTGACATCCAGTTGACCCAGTCTCCACCCTCCCTGTCTGCATCTGTAGGAGACAGAGTCACT

ATCACTTGCCAGGCGCCTCACGACATTAAGAACAATTTAAATTGGTATCAACAGAAACCAGG

GAAAGCCCCTAAACTCCTGATCTTCGACGCATCTAATTTGGAGACGGGAGTCCCATCAAGAT

TCAGTGGAAGTGGATCTGGGACAAATTTTGTGCTCACCATCAGCAGCCTGCAGCCTGAAGAT

ATTGCAACTTATTACTGTCAACAGTTTCATGATCTCCCGCTCACTTTCGGCGGAGGGACCAA

GGTAGACATGAAACGAACTGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGAGAGTGTCACAG

AGCAGGACAGCAAGGACAGCACCTACAGCCTCAGCAGCACCCTGACGCTGAGCAAAGCAGA

CTACGAGAAACACAAAGTCTACGCCTGCGAAGTCACCCATCAGGGCCTGAGCTCGCCCGTC

ACAAAGAGCTTCAACAGGGGAGAGTGT

2B3 $V_H$:

(SEQ ID NO: 55)

CAGCTGCAGCTGCAGGAGTCGGGGGGAGGCGTGGTCCAGCCTGGGAGGTCCCTGAGACTCT

CCTGTGCAGCCTCTGGATTCACCTTCAGTAGCTATGCTATGCACTGGGTCCGCCAGGCTCCA

GGCAAGGGGCTGGAGTGGGTGGCAGTTATATCATATGATGGAAGCAATAAATACTACGCAG

ACTCCGTGAAGGGCCGATTCACCATCTCCAGAGACAATTCCAAGAACACGCTGTATCTGCAA

ATGAACAGCCTGAGAGCTGAGGACACGGCTGTGTATTACTGTGCGAGACCCTATAGCAGCA

GCTGGTACAGCGTTGGGAACTACGGTATAGACGTCTGGGGCCAAGGGACCACGGTCACCGT

CTCAAGCGCCTCCACCAAGGGCCCATCGGTCTTCCCCCTGGCACCCTCCTCCAAGAGCACCT

CTGGGGGCACAGCGGCCCTGGGCTGCCTGGTCAAGGACTACTTCCCCGAACCGGTGACGGT

GTCGTGGAACTCAGGCGCCCTGACCAGCGGCGTCCACACCTTCCCGGCTGTCCTACAGTCCT

CAGGACTCTACTCCCTCAGCAGCGTAGTGACCGTGCCCTCCAGCAGCTTGGGCACCCAGACC

TACATCTGCAACGTGAATCACAAGCCCAGCAACACCAAGGTGGACAAGAAAGTTGAGCCCA

AATCTTGT

2B3 $V_L$:

(SEQ ID NO: 56)

CAGGCTGTGCTGACTCAGCCGTCTTCCCTCTCTGCATCTCCTGGAGCATCAGCCAGTCTCACC

TGCACCTTACGCAGAGACATTGATATTGGAACCGCCAGGATTTACTGGTACCAACAGAAGCC

AGGGAGCCCCCCCCAGTATCTCCTGAACTACAAATCAGACTTGTACACGGAGAAGGCCTCTG

GAGTCCCCAGCCGCTTCTCTGGATCCAAGGATGCTTCGGCCAATGCAGGCATTTTGCTCATCT

CTGGGCTCCAGTCTGAGGATGAGGCTGACTATTACTGTCTGATTTGGCACAACAATGCTTGG

GTGTTCGGCGGAGGGACCAAGCTGACCGTCCTAGGTCAGCCCAAGGCTGCCCCCTCGGTCAC

-continued

TCTGTTCCCGCCCTCCTCTGAGGAGCTTCAAGCCAACAAGGCCACACTGGTGTGTCTCATAA

GTGACTTCTACCCGGGAGCCGTGACAGTGGCCTGGAAGGCAGATGGCAGCCCCGTCAAGGC

GGGAGTGGAGACCACCAAACCCTCCAAACAGAGCAACAACAAGTACGCGGCCAGCAGCTAC

CTGAGCCTGACGCCCGAGCAGTGGAAGTCCCACAGAAGCTACAGCTGCCAGGTCACGCATG

AAGGGAGCACCGTGGAGAAGACAGTGGCCCCTACAGAATGTTCA

2B7 $V_H$:

(SEQ ID NO: 57)

CAGGTACAGCTGCAGCAGTCAGGTCCAGGACTGGTGAAGCCCTCGCAGACCCTCTCACTCAC

CTGCGCCATCTCCGGGGACAGTGTCTCTAGCAACAGTGCTGCTTGGAACTGGATCAGGCAGT

CCCCATCGAGAGGCCTTGAGTGGCTGGGAAGGACATATTACAGGTCCAAGTGGTATAATGA

TTATGCAGAATCTGTGAAAAGTCGAATAGTCATCAACGTAGACACATCCAAGAACCAGTTCT

CCCTGCAGTTGAACTCTGTGACTCCCGAGGACACGGCTGCGTATTACTGTGCAAGAGATCCG

GGGGGGCCTCTCGATGATAGTTTTGATATCTGGGGCCAAGGGACAATGGTCACCGTCTCAAG

CGCCTCCACCAAGGGCCCATCGGTCTTCCCCCTGGCACCCTCCTCCAAGAGCACCTCTGGGG

GCACAGCGGCCCTGGGCTGCCTGGTCAAGGACTACTTCCCCGAACCGGTGACGGTGTCGTGG

AACTCAGGCGCCCTGACCAGCGGCGTCCACACCTTCCCGGCTGTCCTACAGTCCTCAGGACT

CTACTCCCTCAGCAGCGTAGTGACCGTGCCCTCCAGCAGCTTGGGCACCCAGACCTACATCT

GCAACGTGAATCACAAGCCCAGCAACACCAAGGTGGACAAGAAAGTTGAGCCCAAATCTTG

T

2B7 $V_L$:

(SEQ ID NO: 58)

CAGTCTGTCGTGACGCAGCCGCCCTCAGTGTCTGGGGCGCCAGGTCAGAGGGTCATCATCTC

CTGCACTGGGAGCAGCTCCAACATCGGGGCAGGCTTTGATGTACACTGGTATCAGCAGCTTC

CAGGAACAGTCCCCAAACTCCTCATCTATGGTAACACAAATCGGCCCTCAGGGGTCCCTGAC

CGATTCTCTGGCTCCAAGGCTGGCACCTCAGCCTCCCTGGCCATCACTGGGCTCCAGGCTGA

GGATGAGGCTGATTATTACTGCCAGGCTTATGACGACTCCCTGCAAGGTTATGTCTTCGGCA

CAGGGACCAAGTTAACCGTCGTCGGTCAGCCCAAGGCCAACCCCACTGTCACTCTGTTCCCG

CCCTCCTCTGAGGAGCTCCAAGCCAACAAGGCCACACTAGTGTGTCTGATCAGTGACTTCTA

CCCGGGAGCTGTGACAGTGGCCTGGAAGGCAGATGGCAGCCCCGTCAAGGCGGGAGTGGAG

ACCACCAAACCCTCCAAACAGAGCAACAACAAGTACGCGGCCAGCAGCTACCTGAGCCTGA

CGCCCGAGCAGTGGAAGTCCCACAGAAGCTACAGCTGCCAGGTCACGCATGAAGGGAGCAC

CGTGGAGAAGACAGTGGCCCCTACAGAATGTTCA

2B8 $V_H$:

(SEQ ID NO: 59)

CAGGTACAGCTGCAGCAGTCAGGTCCAGGACTGGTGAAGCCCTCGCAGACCCTCTCACTCAC

CTGTGCCATCTCCGGGGACAGTGTCTCTAGCAAGAGTGCTGCTTGGAACTGGATCAGGCAGT

CCCCATCGAGAGGCCTTGAGTGGCTGGGAAGGACATACTACAGGTCCAAGTGGTATAATGA

TTATGCAGTATCTGTGAAAAGCCGAATAACCATCAACCCAGACACATCCAAGAACCAGTTCT

CCCTGCAGCTGAACTCTGTGACTCCCGAGGACACGGCTGTGTATTACTGTGCAAGAGATCCG

GGGGGGCCTCTCGATGATAGTTTTGATATCTGGGGCCAAGGGACAATGGTCACCGTCTCAAG

CGCCTCCACCAAGGGCCCATCGGTCTTCCCCCTGGCACCCTCCTCCAAGAGCACCTCTGGGG

GCACAGCGGCCCTGGGCTGCCTGGTCAAGGACTACTTCCCCGAACCGGTGACGGTGTCGTGG

-continued

```
AACTCAGGCGCCCTGACCAGCGGCGTCCACACCTTCCCGGCTGTCCTACAGTCCTCAGGACT

CTACTCCCTCAGCAGCGTAGTGACCGTGCCCTCCAGCAGCTTGGGCACCCAGACCTACATCT

GCTACGTGAATCACAAGCCCAGCAACACCAAGGTGGACAAGAAAGTTGAGCCCAAATCTTG

T
```

2B8 $V_L$:

(SEQ ID NO: 60)

```
CTTGATGTTGTGATGACTCAGTCTCCACTCTCCCTGCCCGTCACCCCTGGAGAGCCGGCCTCC

ATCTCCTGCAGGTCTAGTCAGAGCCTCCTGCGTAGTAATGGATACAACTATTTAGATTGGTA

CCTGCAGAAGCCAGGGCAGTCTCCACAGCTCCTGATCTATTTGGGTTCTACTCGGGCCTCCG

GGGTCCCTGACAGGTTCAGTGGCAGTGGATCGGGCACAGATTTTACACTGAAAATCAGCAG

AGTGGAGGCTGAGGATGTTGGGGTTTATTACTGCATGCAAGCTTTTCAAACTCCGCTCACTTT

CGGCGGAGGGACCAAGATGGAGATCAAACGAACTGTGGCTGCACCATCTGTCTTCATCTTCC

CGCCATCTGATGAGCAGTTGAAATCTGGAACTGCCTCTGTTGTGTGCCTGCTGAATAACTTCT

ATCCCAGAGAGGCCAAAGTACAGTGGAAGGTGGATAACGCCCTCCAATCGGGTAACTCCCA

GGAGAGTGTCACAGAGCAGGACAGCAAGGACAGCACCTACAGCCTCAGCAGCACCCTGACG

CTGAGCAAAGCAGACTACGAGAAACACAAAGTCTACGCCTGCGAAGTCACCCATCAGGGCC

TGAGCTCGCCCGTCACAAAGAGCTTCAACAGGGGAGAGTGT
```

2B11 $V_H$:

(SEQ ID NO: 61)

```
CAGGTACAGCTGCAGCAGTCAGGTCCAGGACTGGTGAAGCCCTCGCAGACCCTCTCACTCAC

CTGTGCCATCTCCGGGGACAGTGTCTCTAGCAACAGTGCTGCTTGGAACTGGATCAGGCAGT

CCCCATCGAGAGGCCTTGAGTGGCTGGGAAGGACATACTACAGGTCCAAGTGGTATAATGA

TTATGCAGTATCTGTGAAAAGTCGAATAACCATCAACCCAGACACATCCAAGAACCAGTTCT

CCCTGCAGCTGAACTCTGTGACTCCCGAGGACACGGCTGTGTATTACTGTGCAAGAGATTCG

GGACTGGGGTCAGACTACTTTGACTACTGGGGCCAGGGCACCCTGGTCACCGTCTCAAGCGC

CTCCACCAAGGGCCCATCGGTCTTCCCCCTGGCACCCTCCTCCAAGAGCACCTCTGGGGGCA

CAGCGGCCCTGGGCTGCCTGGTCAAGGACTACTTCCCCGAACCGGTGACGGTGTCGTGGAAC

TCAGGCGCCCTGACCAGCGGCGTCCACACCTTCCCGGCTGTCCTACAGTCCTCAGGACTCTA

CTCCCTCAGCAGCGTAGTGACCGTGCCCTCCAGCAGCTTGGGCACCCAGACCTACATCTGCA

ACGTGAATCACAAGCCCAGCAACACCAAGGTGGACAAGAAAGTTGAGCCCAAATCTTGT
```

2B11 $V_L$:

(SEQ ID NO: 62)

```
CTTGACATCCAGATGACCCAGTCTCCACCCTCCCTGTCTGCATCTGTAGGAGACAGAGTCAC

TATCACTTGCCAGGCGCCTCACGACATTAAGAACAATTTAAATTGGTATCAACAGAAACCAG

GGAAAGCCCCTAAACTCCTGATCTTCGACGCATCTAATTTGGAGACGGGAGTCCCATCAAGA

TTCAGTGGAAGTGGATCTGGGACAAATTTTGTGCTCACCATCAGCAGCCTGCAGCCTGAAGA

TATTGCAACTTATTACTGTCAACAGTTTGATGATCTCCCGCTCACTTTCGGCGGAGGGACCAA

GGTAGACATGAAACGAACTGTGGCTGCACCATCTGTCTTCATCTTCCCGCCATCTGATGAGC

AGTTGGAATCTGGAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGAGAGTGTCACAG

AGCAGGACAGCAAGGACAGCACCTACAGCCTCAGCAGCACCCTGACGCTGAGCAAAGCAGA

CTACGAGAAACACAAAGTCTACGCCTGCGAAGTCACCCATCAGGGCCTGAGCTCGCCCGTC

ACAAAGAGCTTCAACAGGGGAGAGTGT
```

-continued

2D5 $V_H$:

(SEQ ID NO: 63)

CAGGTACAGCTGCAGCAGTCAGGTCCAGGACTGGTGAAGCCCTCGCAGACCCTCTCACTCAC

CTGTGCCATCTCCGGGGACAGTGTCTCTAGCAACAGTGCTGCTTGGAACTGGATCAGGCAGT

CCCCATCGAGAGGCCTTGAGTGGCTGGGAAGGACATACTACAGGTCCAAGTGGTATAATGA

TTATGCAGTATCCGTGAAAAGTCGAATAATTATCAACCCAGACACATCCAAGAACCAGTTCT

CCCTGCAGCTGAACTCTGTGACTCCCGAGGACACGGCTGTGTATTACTGTGCAAGAGATCCG

GGGGGGCCTCTCGATGATAGTTTTGATATCTGGGGCCAAGGGACAATGGTCACCGTCTCAAG

CGCCTCCACCAAGGGCCCATCGGTCTTCCCCCTGGCACCCTCCTCCAAGAGCACCTCTGGGG

GCACAGCGGCCCTGGGCTGCCTGGTCAAGGACTACTTCCCCGAACCGGTGACGGTGTCGTGG

AACTCAGGCGCCCTGACCAGCGGCGTCCACACCTTCCCGGCTGTCCTACAGTCCTCAGGACT

CTACTCCCTCAGCAGCGTAGTGACCGTGCCCTCCAGCAGCTTGGGCACCCAGACCTACATCT

GCAACGTGAATCACAAGCCCAGCAACACCAAGGTGGACAAGAAAGTTGAGCCCAAATCTTG

T

2D5 $V_L$:

(SEQ ID NO: 64)

CTTGACATCCAGTTGACCCAGTCTCCTTCCACCCTGTCTGCATCTGTAGGGGACAGAGTCACC

ATTACTTGCCGGGCCAGTCAGACTATAAGTAGTTCGTTGGCCTGGTATCAGCAGAAACCAGG

GAAAGCCCCTAACCTCCTGATCTATAAGGCGTCTACATTAGAAGGTGGGGTCCCCTCGCGTT

TCAGCGGCAGTGGATCTGGGACAGAATTCACTCTCACCATCAGCAGCCTGCAGCCTGAAGAT

TTTGCAACTTACTACTGTCAACAGAGTTACACTACCCCGCTCACTTTCGGCGGAGGGACCAA

GGTGGAGATCAAACGAACTGTGGCTGCACCATCTGTCTTCATCTTCCCGCCATCTGATGAGC

AGTTGAAATCTGGAACTGCCTCTGTTGTGTGCCTGCTGAATAACTTCTACCCCAGAGAGGCC

AAAGTACAGTGGAAGGTGGATAACGCCCTCCAATCGGGTAACTCCCAGGAGAGTGTCACAG

AGCAGGACAGCAAGGACAGCACCTACAGCCTCAGCAGCACCCTGACGCTGAGCAAAGCAGA

CTACGAGAAACACAAAGTCTACGCCTGCGAAGTCACCCATCAGGGCCTGAGCTCGCCCGTC

ACAAAGAGCTTCAACAGGGGAGAGTGT

2E7 $V_H$:

(SEQ ID NO: 65)

CAGGTACAGCTGCAGCAGTCAGGTCCAGGACTGGTGAAGCCCTCGCAGACCCTCTCACTCAC

CTGTGCCATCTCCGGGGACAGTGTCTCTAGTAACAGTGCTGCTTGGAACTGGATCAGGCAGT

CCCCATCGAGAGGCCTTGAGTGGCTGGGGAGGACATACTACAGGTCCAAGTGGTATTATGAT

TATGCAGTCTCTGTGAAAGGTCGAATAACCTTCACCCCAGACACATCCAAGAACCAGGTCTC

CCTGCACCTGAACGCTGTGACTCCCGAGGACACGGCTATGTATTACTGTGCAAGAGATCCGG

GGGGGCCTCTCGATGATAGTTTTGATATCTGGGGCCAAGGGACAATGGTCACCGTCTCAAGC

GCCTCCACCAAGGGCCCATCGGTCTTCCCCCTGGCACCCTCCTCCAAGAGCACCTCTGGGGG

CACAGCGGCCCTGGGCTGCCTGGTCAAGGACTACTTCCCCGAACCGGTGACGGTGTCGTGGA

ACTCAGGCGCCCTGACCAGCGGCGTCCACACCTTCCCGGCTGTCCTACAGTCCTCAGGACTC

TACTCCCTCAGCAGCGTAGTGACCGTGCCCTCCAGCAGCTTGGGCACCCAGACCTACATCTG

CAACGTGAATCACAAGCCCAGCAACACCAAGGTGGACAAGAAAGTTGAGCCCAAATCTTGT

2E7 $V_L$:

(SEQ ID NO: 66)

CTTGACATCCAGTTGACCCAGTCTCCACCCTCCCTGTCTGCATCTGTAGGAGACAGAGTCACT

ATCACTTGCCAGGCGCCTCACGACATTAAGAACAATTTAAATTGGTATCAACAGAAACCAGG

GAAAGCCCCTAAACTCCTGATCTTCGACGCATCTAATTTGGAGACGGGAGTCCCATCAAGAT

-continued

TCAGTGGAAGTGGATCTGGGACAAATTTTGTGCTCACCATCAGCAGCCTGCAGCCTGAAGAT

ATTGCAACTTATTACTGTCAACAGTTTCATGATCTCCCGCTCACTTTCGGCGGAGGGACCAA

GGTAGACATGAAACGAACTGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGAGAGTGTCACAG

AGCAGGACAGCAAGGACAGCACCTACAGCCTCAGCAGCACCCTGACGCTGAGCAAAGCAGA

CTACGAGAAACACAAAGTCTACGCCTGCGAAGTCACCCATCAGGGCCTGAGCTCGCCCGTC

ACAAAGAGCTTCAACAGGGGAGAGTGT

2E9 $V_H$:

(SEQ ID NO: 67)

CAGGTGCAGCTGCAGGAGTCGGGGGGAGGCTTGGTACAGCCTGGGGGGTCCCTGAGACTCT

CCTGTGCAGCCTCTGGATTCACCTTTAGCAGCTATGCCATGAGCTGGGTCCGCCAGGCTCCA

GGGAAGGGGCTGGAGTGGGTCTCAGCTATTAGTGGTAGTGGTGGTAGCACATACTACGCAG

ACTCCGTGAAGGGCCGGTTCACCATCTCCAGAGACAATTCCAAGAACACGCTGTATCTGCAA

ATGAACAGCCTGAGAGCCGAGGACACGGCCGTATATTACTGTGCGAAAGATGAGGATTATG

ATTACGTTTGGGGGAGTTATCGACAATACCCCAGTCGCTACTGGGGCCAGGGAACCCTGGTC

ACCGTCTCAAGCGCCTCCACCAAGGGCCCATCGGTCTTCCCCCTGGCACCCTCCTCCAAGAG

CACCTCTGGGGGCACAGCGGCCCTGGGCTGCCTGGTCAAGGACTACTTCCCCGAACCGGTGA

CGGTGTCGTGGAACTCAGGCGCCCTGACCAGCGGCGTCCACACCTTCCCGGCTGTCCTACAG

TCCTCAGGACTCTACTCCCTCAGCAGCGTAGTGACCGTGCCCTCCAGCAGCTTGGGCACCCA

GACCTACATCTGCAACGTGAATCACAAGCCCAGCAACACCAAGGTGGACAAGAAAGTTGAG

CCCAAATCTTGT

2E9 $V_L$:

(SEQ ID NO: 68)

CAGTCTGTGCTGACTCAGCCACCCTCAGTGTCCGTGTCCCCAGGACAGACAGCCAGCATCAC

CTGCTCTGGAGATAATTTGGGGTATAAATATGCTTCCTGGTATCAGCAGAAGCCAGGCCAGT

CCCCTGTGCTGATCATCTATCAAGATAAGAAGCGGCCCTCTGGGATCCCTGAGCGATTCTCT

GGCTCCAACTCTGGGAACACAGCCACTCTGACCATCAGCGGGACCCAGGCTATGGATGAGG

CTGACTATTACTGTCAGGCGTGGGACAGCAGCACTTCTGTGGTATTCGGCGGAGGGACCAAG

CTGACCGTCCTAGGTCAGCCCAAGGCTGCCCCCTCGGTCACTCTGTTCCCACCCTCCTCTGAG

GAGCTTCAAGCCAACAAGGCCACACTGGTGTGTCTCATAAGTGACTTCTACCCGGGAGCCGT

GACAGTGGCCTGGAAGGCAGATAGCAGCCCCGTCAAGGCGGGAGTGGAGACCACCACACCC

TCCAAACAAAGCAACAACAAGTACGCGGCCAGCAGCTATCTGAGCCTGACGCCTGAGCAGT

GGAAGTCCCACAGAAGCTACAGCTGCCAGGTCACGCATGAAGGGAGCACCGTGGAGAAGAC

AGTGGCCCCTACAGAATGTTCA

2G10 $V_H$:

(SEQ ID NO: 69)

CAGGTACAGCTGCAGCAGTCAGGTCCAGGACTGGTGAAGCCCTCGCAGACCCTCTCACTCAC

CTGTGCCATCTCCGGGGACAGTGTCTCTAGCAACAGTGCTGCTTGGAACTGGATCAGGCAGT

CCCCATCGAGAGGCCTTGAGTGGCTGGGAAGGACATACTACAGGTCCAAGTGGTATAATGA

TTATGCAGTATCCGTGAAAAGTCGAATAATTATCAACCCAGACACATCCAAGAACCAGTTCT

CCCTGCAGCTGAACTCTGTGACTCCCGAGGACACGGCTGTGTATTACTGTGCAAGAGATCCG

GGGGGGCCTCTCGATGATAGTTTTGATATCTGGGGCCAAGGGACAATGGTCACCGTCTCAAG

-continued

CGCCTCCACCAAGGGCCCATCGGTCTTCCCCCTGGCACCCTCCTCCAAGAGCACCTCTGGGG

GCACAGCGGCCCTGGGCTGCCTGGTCAAGGACTACTTCCCCGAACCGGTGACGGTGTCGTGG

AACTCAGGCGCCCTGACCAGCGGCGTCCACACCTTCCCGGCTGTCCTACAGTCCTCAGGACT

CTACTCCCTCAGCAGCGTAGTGACCGTGCCCTCCAGCAGCTTGGGCACCCAGACCTACATCT

GCAACGTGAATCACAAGCCCAGCAACACCAAGGTGGACAAGAAAGTTGAGCCCAAATCTTG

T

2G10 $V_L$:

(SEQ ID NO: 70)

CTTGATGTTGTGATGACTCAGTCTCCACTCTCCCTGCCCGTCACCCCTGGAGAGCCGGCCTCC

ATCTCCTGCAGGTCTAGTCAGAGCCTCCTGCGTAGTAATGGATACAACTATTTGGATTGGTA

CCTGCAGAAGCCAGGGCAGTCTCCACAGCTCCTGATCTATTTGGGTTCTATTCGGGCCTCCG

GGGTCCCTGACAGGTTCAGTGGCAGTGGATCGGGCACAGATTTTACACTGAGAATTAGCAG

AGTGGAGGCTGAGGATGTTGGGGTTTATTACTGCATGCAAGCTCTACAAACCCCGTTCACTT

TTGGCCAGGGGACCAAGCTGGAGATCAAGCGAACTGTGGCTGCACCATCTGTCTTCATCTTC

CCGCCATCTGATGAGCAGTTGAAATCTGGAACTGCCTCTGTTGTGTGCCTGCTGAATAACTTC

TATCCCAGAGAGGCCAAAGTACAGTGGAAGGTGGATAACGCCCTCCAATCGGGTAACTCCC

AGGAGAGTGTCACAGAGCAGGACAGCAAGGACAGCACCTACAGCCTCAGCAGCACCCTGAC

GCTGAGCAAAGCAGACTACGAGAAACACAAAGTCTACGCCTGCGAAGTCACCCATCAGGGC

CTGAGCTCGCCCGTCACAAAGAGCTTCAACAGGGGAGAGTGT

2G12 $V_H$:

(SEQ ID NO: 71)

GAGGTGCAGCTGGTGGACACTGGGGGAGGCTTGGTACAGCCTGGGGGGTCCCTGAGACTCT

CCTGTGCAGCCTCTGGATTCACCTTTAGCAGCTATGCCATGAGCTGGGTCCGCCAGGCTCCA

GGGAAGGGGCTGGAGTGGGTCTCAGCTATTAGTGGTAGTGGTGGTAGCACATACTACGCAG

ACTCCGTGAAGGGCCGGTTCACCATCTCCAGAGACAATTCCAAGAACACGCTGTATCTGCAA

ATGAACAGCCTGAGAGCCGAGGACACGGCCGTATATTATTGTGCGAAAGATTGGGGAAGAA

ATATAGCAGTGGCTGGTACCCTTGACTACTGGGGCCAGGGCACCCTGGTCACCGTCTCAAGC

GCCTCCACCAAGGGCCCATCGGTCTTCCCCCTGGCACCCTCCTCCAAGAGCACCTCTGGGGG

CACAGCGGCCCTGGGCTGCCTGGTCAAGGACTACTTCCCCGAACCGGTGACGGTGTCGTGGA

ACTCAGGCGCCCTGACCAGCGGCGTCCACACCTTCCCGGCTGTCCTACAGTCCTCAGGACTC

TACTCCCTCAGCAGCGTAGTGACCGTGCCCTCCAGCAGCTTGGGCACCCAGACCTACATCTG

CAACGTGAATCACAAGCCCAGCAACACCAAGGTGGACAAGAAAGTTGAGCCCAAATCTTGT

2G12 $V_L$:

(SEQ ID NO: 72)

CTTTCCTATGAGCTGACTCAGCCACCCTCAGTGTCGGTGTCCCCAGGACAGACAGCCAGCAT

TACCTGCTCTGGAGATAAATTGGGACAAAAGTATGTTTCATGGTATCAGCAGAGGCCAGGCC

AGTCTCCTCTACTGGTCATCTTTCAAGATGACAAGCGGCCCTCAGGGATCCCTGAGCGAATC

TCTGGCTCCAACTCTGGGCACACAGCCACTCTGACCATCAGCGCGACCCAGGCTATGGATGA

GGCTGAGTATTTCTGTCAGGCGTGGGACAGTAACACTGCCCCTTATGTCTTCGGAACTGGGA

CCCAGGTCACCGTCCTAAGTCAGCCCAAGGCCAACCCCACTGTCACTCTGTTCCCGCCCTCCT

CTGAGGAGCTCCAAGCCAACAAGGCCACACTAGTGTGTCTGATCAGTGACTTCTACCCGGGA

GCTGTGACAGTGGCCTGGAAGGCAGATGGCAGCCCCGTCAAGGCGGGAGTGGAGACCACCA

-continued

AACCCTCCAAACAGAGCAACAACAAGTACGCGGCCAGCAGCTACCTGAGCCTGACGCCCGA

GCAGTGGAAGTCCCACAGAAGCTACAGCTGCCAGGTCACGCATGAAGGGAGCACCGTGGAG

AAGACAGTGGCCCCTACAGAATGCTCT

3C6 $V_H$:

(SEQ ID NO: 73)

CAGGTGCAGCTACAGCAGTGGGGCGCAGGACTGTTGAAGCCTTCGGAGACCCTGTCCCTCAC

CTGCGCTGTCTATGGTGGGTCCTTCAGTGGTTACTACTGGAGCTGGATCCGCCAGCCCCCAG

GGAAGGGGCTGGAGTGGATTGGGGAAATCAATCATAGTGGAAGCACCAACTACAACCCGTC

CCTCAAGAGTCGAGTCACCATATCAGTAGACACGTCCAAGAACCAGTTCTCCCTGAAGCTGA

GCTCTGTGACCGCCGCGGACACGGCTGTGTATTACTGTGCGAGAGGCAGAAGGTTCGGGGA

TTTTGACTACTGGGGCCAGGGAACCCTGGTCACCGTCTCAAGCGCCTCCACCAAGGGCCCAT

CGGTCTTCCCCCTGGCACCCTCCTCCAAGAGCACCTCTGGGGGCACAGCGGCCCTGGGCTGC

CTGGTCAAGGACTACTTCCCCGAACCGGTGACGGTGTCGTGGAACTCAGGCGCCCTGACCAG

CGGCGTCCACACCTTCCCGGCTGTCCTACAGTCCTCAGGACTCTACTCCCTCAGCAGCGTAGT

GACCGTGCCCTCCAGCAGCTTGGGCACCCAGACCTACATCTGCAACGTGAATCACAAGCCCA

GCAACACCAAGGTGGACAAGAAAGTTGAGCCCAAATCTTGT

3C6 $V_L$:

(SEQ ID NO: 74)

CAGCCTGTGCTGACTCAGCCCCCCTCGGTGTCAGTGGCCCCAGGAAAGACGGCCAGGATTAC

CTGTGGGGGAAACAACATTGGAAGTAAAAGTGTGCACTGGTACCAGCAGAAGCCAGGCCAG

GCCCCTGTGCTGGTCGTCTATGATGATAGCGACCGGCCCCCAGGGATCCCTGAGCGATTCTC

TGGCTCCAATTCTGGGAACACGGCCACCCTGACCATCAGCAGGGTCGAAGCCGGGGATGAG

GCCGACTATTACTGTCAGGTGTGGGATAGTAGTAGTGATCACTCCCCCTTCGGAACTGGGAC

CAAGGTCACCGTCCTAGGTCAGCCCAAGGCCAACCCCACTGTCACTCTGTTCCCGCCCTCCT

CTGAGGAGCTCCAAGCCAACAAGGCCACACTAGTGTGTCTGATCAGTGACTTCTACCCGGGA

GCTGTGACAGTGGCCTGGAAGGCAGATGGCAGCCCCGTCAAGGCGGGAGTGGAGACCACCA

AACCCTCCAAACAGAGCAACAACAAGTACGCGGCCAGCAGCTACCTGAGCCTGACGCCCGA

GCAGTGGAAGTCCCACAGAAGCTACAGCTGCCAGGTCACGCATGAAGGGAGCACCGTGGAG

AAGACAGTGGCCCCTACAGAATGCTCT

3C7 $V_H$:

(SEQ ID NO: 75)

CAGGTACAGCTGCAGCAGTCAGGTCCAGGACTGGTGAAGCCCTCGCAGACCCTCTCACTCAC

CTGTGCCATCTCCGGGGACAGTGTCTCTAGCAACAGTGCTGCTTGGAACTGGATCAGGCAGT

CCCCATCGAGAGGCCTTGAGTGGCTGGGAAGGACATACTACAGGTCCAAGTGGTATAATGA

TTATGCAGTATCCGTGAAAAGTCGAATAATTATCAACCCAGACACATCCAAGAACCAGTTCT

CCCTGCAGCTGAACTCTGTGACTCCCGAGGACACGGCTGTGTATTACTGTGCAAGAGATCCG

GGGGGGCCTCTCGATGATAGTTTTGATATCTGGGGCCAAGGGACAATGGTCACCGTCTCAAG

CGCCTCCACCAAGGGCCCATCGGTCTTCCCCCTGGCACCCTCCTCCAAGAGCACCTCTGGGG

GCACAGCGGCCCTGGGCTGCCTGGTCAAGGACTACTTCCCCGAACCGGTGACGGTGTCGTGG

AACTCAGGCGCCCTGACCAGCGGCGTCCACACCTTCCCGGCTGTCCTACAGTCCTCAGGACT

CTACTCCCTCAGCAGCGTAGTGACCGTGCCCTCCAGCAGCTTGGGCACCCAGACCTACATCT

GCAACGTGAATCACAAGCCCAGCAACACCAAGGTGGACAAGAAAGTTGAGCCCAAATCTTG

T

-continued

3C7 $V_L$:

(SEQ ID NO: 76)

CTTGACATCCAGTTGACCCAGTCTCCACCCTCCCTGTCTGCATCTGTAGGAGACAGAGTCACT

ATCACTTGCCAGGCGCCTCACGACATTAAGAACAATTTAAATTGGTATCAACAGAAACCAGG

GAAAGCCCCTAAACTCCTGATCTTCGACGCATCTAATTTGGAGACGGGAGTCCCATCAAGAT

TCAGTGGAAGTGGATCTGGGACAAATTTTGTGCTCACCATCAGCAGCCTGCAGCCTGAAGAT

ATTGCAACTTATTACTGTCAACAGTTTGATGATCTCCCGCTCACTTTCGGCGGAGGGACCAA

GGTAGACATGAAACGAACTGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGAGAGTGTCACAG

AGCAGGACAGCAAGGACAGCACCTACAGCCTCAGCAGCACCCTGACGCTGAGCAAAGCAGA

CTACGAGAAACACGAAGTCTACGCCTGCGAAGTCACCCATCAGGGCCTGAGCTCGCCCGTC

ACAAAGAGCTTCAACAGGGGAGAGTGT

3D6 $V_H$:

(SEQ ID NO: 77)

CAGGTACAGCTGCAGCAGTCAGGTCCAGGACTGGTGAACCCCTCGCAGACCCTCTCAGTCAC

ATGTGCCATCTCCGGGGACAGTGTCTCTAGCAACAGTGCTGCTTGGAACTGGATCAGGCAGT

CCCCATCGAGAGGCCTTGAGTGGCTGGGGAGGACATACTACAGGTCGAAGTGGTATAATGA

TTATGCAGTATCTGTGAAAAGTCGAATAACCATCAAACCAGACACATCCAAGAACCAGTTCT

CCCTGCAGCTGAACTCTGTGACTCCCGACGACACGGCTGTGTATTACTGTGCAAGAGATCCG

GGGGGGTCTCTCGATGATTCTTTTGATATCTGGGGCCAAGGGACCACGGTCACCGTCTCAAG

CGCCTCCACCAAGGGCCCATCGGTCTTCCCCCTGGCACCCTCCTCCAAGAGCACCTCTGGGG

GCACAGCGGCCCTGGGCTGCCTGGTCAAGGACTACTTCCCCGAACCGGTGACGGTGTCGTGG

AACTCAGGCGCCCTGACCAGCGGCGTCCACACCTTCCCGGCTGTCCTACAGTCCTCAGGACT

CTACTCCCTCAGCAGCGTAGTGACCGTGCCCTCCAGCAGCTTGGGCACCCAGACCTACATCT

GCAACGTGAATCACAAGCCCAGCAACACCAAGGTGGACAAGAAAGTTGAGCCCAAATCTTG

T

3D6 $V_L$:

(SEQ ID NO: 78)

CTTGACATCCAGATGACCCAGTCTCCACCCTCCCTGTCTGCATCTGTAGGAGACAGAGTCAC

TATCACTTGCCAGGCGCCTCACGACATTAAGAACAATTTAAATTGGTATCAACAGAAACCAG

GGAAAGCCCCTAAACTCCTGATCTTCGACGCATCTAATTTGGAGACGGGAGTCCCATCAAGA

TTCAGTGGAAGTGGATCTGGGACAAATTTTGTGCTCACCATCAGCAGCCTGCAGCCTGAAGA

TATTGCAACTTATTACTGTCAACAGTTTGATGATCTCCCGCTCACTTTCGGCGGAGGGACCAA

GGTAGACATGAAACGAACTGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCC

AAAGTACAGTGGAAGGTGGATAACGCCCTCCAATCGGGTAACTCCCAGGAGAGTGTCACAG

AGCAGGACAGCAAGGACAGCACCTACAGCCTCAGCAGCACCCTGACGCTGAGCAAAGCAGA

CTACGAGAAACACAAAGTCTACGCCTGCGAAGTCACCCATCAGGGCCTGAGCTCGCCCGTC

ACAAAGAGCTTCAACAGGGGAGAGTGT

3F7 $V_H$:

(SEQ ID NO: 79)

CAGGTGCAGCTGCAGGAGTCGGGCCCAGGACTGGTGAAGCCCTCGGAGACCCTGTCCCTCA

CTTGCACTGTCTCTGGTGGCTCCTTCAGCAGTTACTACTGGAGCTGGATCCGGCAGCCCCCA

GGGAAGGGACTGGAGTGGATTGGGTATATTTCTGACAGTGGGAGCACCAACTACAACCCCT

-continued

CCCTCCAGTCTCGAGTCACCATATCATTAGACACGTCCAAGAACCAGTTCTCCCTGAAACTG

AACTCTGTGACCGCCACAGACACGGCCGTGTATTACTGTGCGAGAGGCCCGCCTATTCATGA

TTACGTTTGGGGGAGTTATCGCCGCCCCTCGCGAGAATATGATATCTGGGGCCAAGGGACAA

TGGTCACCGTCTCAAGCGCCTCCACCAAGGGCCCATCGGTCTTCCCCCTGGCACCCTCCTCCA

AGAGCACCTCTGGGGGCACAGCGGCCCTGGGCTGCCTGGTCAAGGACTACTTCCCCGAACC

GGTGACGGTGTCGTGGAACTCAGGCGCCCTGACCAGCGGCGTCCACACCTTCCCGGCTGTCC

TACAGTCCTCAGGACTCTACTCCCTCAGCAGCGTAGTGACCGTGCCCTCCAGCAGCTTGGGC

ACCCAGACCTACATCTGCAACGTGAATCACAAGCCCAGCAACACCAAGGTGGACAAGAAAG

TTGAGCCCAAATCTTGT

3F7 $V_L$:

(SEQ ID NO: 80)

CTTAATTTTATGCTGACTCAGCCCCACTCTGTGTCGGAGTCTCCGGGGAAGACGGTTACTATC

TCCTGCACCCGCAGCAGTGGCAGCGTTGCCAGCAACTATGTCCACTGGTACCAGCAGCGACC

GGGCAGTTCCCCCTCCATTCTAATCCATGAGTTTAACATAAGACCCTCTGGGGTCCCTGATCG

GTTCTCAGGCTCCATCGACAGCTCCTCCAACTCTGCCTCCCTCACCATCTCTGGACTGACGAC

TGAGGACGAGGCTGATTACTATTGTCAGTCTTCTGTCAACAACCTTCAATGGGTGCTCGGCG

GAGGGACCAAGCTGACCGTCCTGGGTCAGCCCAAGGCTGCCCCCTCGGTCACTCTGTTCCCA

CCCTCCTCTGAGGAGCTTCAAGCCAACAAGGCCACACTGGTGTGTCTCATAAGTGACTTCTA

CCCGGGAGCCGTGACAGTGGCCTGGAAGGCAGATAGCAGCCCCGTCAAGGCGGGAGTGGAG

ACCACCACACCCTCCAAACAAAGCAACAACAAGTACGCGGCCAGCAGCTACCTGAGCCTGA

CGCCTGAGCAGTGGAAGTCCCACAAAAGCTACAGCTGCCAGGTCACGCATGAAGGGAGCAC

CGTGGAGAAGACAGTGGCCCCTACAGAATGTTCA

3H7 $V_H$:

(SEQ ID NO: 81)

CAGGTACAGCTGCAGCAGTCAGGTCCAGGACTGGTGAAGCCCTCGCAGACCCTCTCACTCAC

CTGTGCCATCTCCGGGGACAGTGTCTCTAGCAACAGTGCTGCTTGGAACTGGATCAGGCAGT

CCCCATCGAGAGGCCTTGAGTGGCTGGGAAGGACATACTACAGGTCGAAGTGGTATAATGA

TTATGCAGTATCTGTGAAAAGTCGAATAACCATCAAACCAGACACATCCAAGAACCAGTTCT

CCCTGCAGCTGAACTCTGTGACTCCCGACGACACGGCTGTGTATTACTGTGCAAGAGATCCG

GGGGGGTCTCTCGATGATTCTTTTGATATCTGGGGCCAAGGGACAATGGTCACCGTCTCAAG

CGCCTCCACCAAGGGCCCATCGGTCTTCCCCCTGGCACCCTCCTCCAAGAGCACCTCTGGGG

GCACAGCGGCCCTGGGCTGCCTGGTCAAGGACTACTTCCCCGAACCGGTGACGGTGTCGTGG

AACTCAGGCGCCCTGACCAGCGGCGTCCACACCTTCCCGGCTGTCCTACAGTCCTCAGGACT

CTACTCCCTCAGCAGCGTAGTGACCGTGCCCTCCAGCAGCTTGGGCACCCAGACCTACATCT

GCAACGTGAATCACAAGCCCAGCAACACCAAGGTGGACAAGAAAGTTGAGCCCAAATCTTG

T

3H7 $V_L$:

(SEQ ID NO: 82)

CTTGATGTTGTGATGACTCAGTCTCCACTCTCCCTGCCCGTCACCCCTGGAGAGCCGGCCTCC

ATCTCCTGCAGGTCTAGTCAGAGCCTCCTGCGTAGTAATGGATACAACTATTTAGATTGGTA

CCTGCAGAAGCCAGGGCAGTCTCCACAGCTCCTGATCTATTTGGGTTCTACTCGGGCCTCCG

GGGTCCCTGACAGGTTCAGTGGCAGTGGATCGGGCACAGATTTTACACTGAAAATCAGCAG

AGTGGAGGCTGAAGATGTTGGGGTTTATTACTGCATGCAAGCTTTTCAAACTCCGCTCACTTT

-continued

CGGCGGAGGGACCAAGATGGAGATCAAACGAACTGTGGCTGCACCATCTGTCTTCATCTTCC

CGCCATCTGATGAGCAGTTGAAATCTGGAACTGCCTCTGTTGTGTGCCTGCTGAATAACTTCT

ATCCCAGAGAGGCCAAAGTACAGTGGAAGGTGGATAACGCCCTCCAATCGGGTAACTCCCA

GGAGAGTGTCACAGAGCAGGACAGCAAGGACAGCACCTACAGCCTCAGCAGCACCCTGACG

CTGAGCAAAGCAGACTACGAGAAACACAAAGTCTACGCCTGCGAAGTCACCCATCAGGGCC

TGAGCTCGCCCGTCACAAAGAGCTTCAACAGGGGAGAGTGT

4B6 $V_H$:

(SEQ ID NO: 83)

CAGGTACAGCTGCAGCAGTCAGGTCCAGGACTGGTGAAGCCCTCGCAGACCCTCTCACTCAC

CTGTGCCATCTCCGGGGACAGTGTCTCTAGCAACAGTGCTGCTTGGAACTGGATCAGGCAGT

CCCCATCGAGAGGCCTTGAGTGGCTGGGAAGGACATACTACAGGTCCAAGTGGTATAATGA

TTATGCAGTATCCGTGAAAAGTCGAATAATTATCAACCCAGACACATCCAAGAACCAGTTCT

CCCTGCAGCTGAACTCTGTGACTCCCGAGGACACGGCTGTGTATTACTGTGCAAGAGATCCG

GGGGGGCCTCTCGATGATAGTTATGATATCTGGGGCCAAGGGACAATGGTCACCGTCTCAAG

CGCCTCCACCAAGGGCCCATCGGTCTTCCCCCTGGCACCCTCCTCCAAGAGCACCTCTGGGG

GCACAGCGGCCCTGGGCTGCCTGGTCAAGGACTACTTCCCCGAACCGGTGACGGTGTCGTGG

AACTCAGGCGCCCTGACCAGCGGCGTCCACACCTTCCCGGCTGTCCTACAGTCCTCAGGACT

CTACTCCCTCAGCAGCGTAGTGACCGTGCCCTCCAGCAGCTTGGGCACCCAGACCTACATCT

GCAACGTGAATCACAAGCCCAGCAACACCAAGGTGGACAAGAAAGTTGAGCCCAAATCTTG

T

4B6 $V_L$:

(SEQ ID NO: 84)

CTTGAAATTGTGCTGACTCAGTCTCCACTCTCCCTGCCCGTCACCCCTGGAGAGCCGGCCTCC

ATCTCCTGCAGGTCTAGTCAGAGCCTCCTGCGTAGTAATGGATACAACTATTTAGATTGGTA

CCTGCAGAAGCCAGGGCAGTCTCCACAGCTCCTGATCTATTTGGGTTCTAATCGGGCCTCCG

GGGTCCCTGACAGGTTCAGTGGCAGTGGATCAGGCACAGATTTTACACTGAAAATCAGCAG

AGTGGAGGCTGAGGATGTTGGGGTTTATTACTGCATGCAAGCTTTTCAAACTCCGCTCACTTT

CGGCGGAGGGACCAAGATGGAGATCAAACGAACTGTGGCTGCACCATCTGTCTTCATCTTCC

CGCCATCTGATGAGCAGTTGAAATCTGGAACTGCCTCTGTTGTGTGCCTGCTGAATAACTTCT

ATCCCAGAGAGGCCAAAGTACAGTGGAAGGTGGATAACGCCCTCCAATCGGGTAACTCCCA

GGAGAGTGTCACAGAGCAGGACAGCAAGGACAGCACCTACAGCCTCAGCAGCACCCTGACG

CTGAGCAAAGCAGACTACGAGAAACACAAAGTCTACGCCTGCGAAGTCACCCATCAGGGCC

TGAGCTCGCCCGTCACAAAGAGCTTCAACAGGGGAGAGTGT

4C1 $V_H$:

(SEQ ID NO: 85)

CAGGTGCAGCTGGTGGAGTCTGGGGGAGGCTTGGTACAGCCTGGGGGGTCCCTGAGACTCT

CCTGTGCAGCCTCTGGATTCACCTTTAGCAGCTATGCCATGAGCTGGGTCCGCCAGGCTCCA

GGGAAGGGGCTGGAGTGGGTCTCAAGTATTAGTGCTAGTGGTGGTAGCACAGACTACGCAG

ACTCCGTGAAGGGCAGATTCACCATCTCCAGAGACAATTCCAAGAACACTCTGTATCTTCAA

ATGAGCAGTCTGAGAGCTGAGGACACGGCTGTGTATTACTGTGTGAAAGAGCGTCCGGATT

ACGATTTTTGGAGTGCGTTCGACCCCTGGGGCCAGGGAACCCTGGTCACCGTCTCAAGCGCC

TCCACCAAGGGCCCATCGGTCTTCCCCCTGGCACCCTCCTCCAAGAGCACCTCTGGGGGCAC

AGCGGCCCTGGGCTGCCTGGTCAAGGACTACTTCCCCGAACCGGTGACGGTGTCGTGGAACT

CAGGCGCCCTGACCAGCGGCGTCCACACCTTCCCGGCTGTCCTACAGTCCTCAGGACTCTAC

-continued

```
TCCCTCAGCAGCGTAGTGACCGTGCCCTCCAGCAGCTTGGGCACCCAGACCTACATCTGCAA

CGTGAATCACAAGCCCAGCAACACCAAGGTGGACAAGAAAGTTGAGCCCAAATCTTGT
```

4C1 $V_L$:

```
                                                      (SEQ ID NO: 86)
CTTGATGTTGTGATGACTCAGTCTCCACTCTCCCTGCCCGTCACCCCTGGAGAGCCGGCCTCC

ATCTCCTGCAGGTCTAGTCAGAGCCTCCTGCATAGTAATGGATACAACTATTTGGATTGGTA

CCTGCAGAAGCCGGGGCAGTCTCCACAGCTCCTGATCTATTTGGGTTCTAATCGGGCCTCCG

GGGTCCCTGACAGGTTCAGTGGCAGTGGATCAGGCACAGATTTTACACTGAAAATCAGCAG

AGTGGAGGCTGAGGATGTTGGGGTTTATTACTGCATGCAAGGTACACACTGGCCTCCGACTT

TTGGCCAGGGGACCAAGCTGGAGATCAAACGAACTGTGGCTGCACCATCTGTCTTCATCTTC

CCGCCATCTGATGAGCAGTTGAAATCTGGAACTGCCTCTGTTGTGTGCCTGCTGAATAACTTC

TATCCCAGAGAGGCCAAAGTACAGTGGAAGGTGGATAACGCCCTCCAATCGGGTAACTCCC

AGGAGAGTGTCACAGAGCAGGACAGCAAGGACAGCACCTACAGCCTCAGCAGCACCCTGAC

GCTGAGCAAAGCAGACTACGAGAAACACAAACTCTACGCCTGCGAAGTCACCCATCAGGGC

CTGAGCTCGCCCGTCACAAAGAGCTTCAACAGGGGAGAGTGT
```

The Fc region optionally present at the C-terminus of the heavy chain can be encoded by a contiguous nucleotide sequence having 80% identity to (e.g., at least 85%, at least 90%, at least 95%, at least 98%, or 100%) to a contiguous sequence of the following DNA sequence:

```
                                                      (SEQ ID NO: 87)
TTGCTAGCACCcTcCTCCAAGAGCACCTCTGGGGGCACAGCGGCCCTGGGCTGCCTGGTCAA

GGACTACTTCCCCGAACCGGTGACGGTGTCGTGGAACTCAGGCGCCcTGACCAGCGGCGTCC

ACACCTTCCCGGCTGTcCTACAGTCCTCCGGACTCTACTCCCTCAGCAGCGTAGTGACCGTGC

CCTCCAGCAGCTTGGGCACCCAGACCTACATCTGCAACGTGAATCACAAGCCCAGCAACACC

AAGGTGGACAAGAAAGTTGAGCCCAAATCTTGTGACAAAACTCACACATGCCCACCGTGCC

CAGCACCTGAACTCCTGGGGGGACCGTCAGTCTTCCTCTTCCCCCCAAAACCCAAGGACACC

CTCATGATCTCCCGGACCCCTGAGGTCACATGCGTGGTGGTGGACGTGAGCCACGAAGACCC

TGAGGTCAAGTTCAACTGGTACGTGGACGGCGTGGAGGTGCATAATGCCAAGACAAAGCCG

CGGGAGGAGCAGTACAACAGCACGTACCGTGTGGTCAGCGTCCTCACCGTCCTGCACCAGG

ACTGGCTGAATGGCAAGGAGTACAAGTGCAAGGTCTCCAACAAAGCCCTCCCAGCCCCCAT

CGAGAAAACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAAGGCTTCTA

TCCCAGCGACATCGCCGTGGAGTGGGAGAGCAATGGGCAGCCGGAGAACAACTACAAGACC

ACGCCTCCCGTGCTGGACTCCGACGGCTCCTTCTTCCTCTACAGCAAGCTCACCGTGgACAAG

AGCAGGTgGCAGCAGGGGAACGTCTTCTCATGCTCCGTGATGCATGAGgCTCTGCACaAcCAC

TACACGCAGAAGAGCCTCTCCCTGTCTCCGGGTAAA.
```

Diagnostic Methods

The present disclosure provides methods of detecting uPAR in a biological sample in situ or isolated from a subject. Since certain cancers (e.g. metastatic cancer) overexpress uPAR, detection of uPAR can aid in diagnosis, choice of therapy, and prognosis. The subject method generally involves contacting a sample containing a cell with a subject agent (e.g. antibody); and directly or indirectly detecting binding of the subject agent (e.g. antibody) to a cell in the sample. The cell can be in vitro, where the cell is in a biological sample obtained from a patient suspected of having, or known to have uPAR-positive cells (e.g. cancer cells), a patient undergoing treatment, or a patient being tested for susceptibility to treatment. The cell can be in vivo, e.g., the cell is in a patient suspected for having cancer cells, a patient undergoing treatment, or a patient being tested for susceptibility to treatment.

Antibodies that bind uPAR can be used to detect uPAR-expressing cells in a biological sample of a subject having or suspected of having cells expressing a detectable level of uPAR (e.g. cancer cells) using anti-uPAR antibodies in immunodiagnostic techniques known in the art. The present disclosure provides antibodies suitable for the purpose of detection of uPAR-expressing cancer cells. Some examples of cancer cells that can be detected using the subject antibodies include cancer cells of the breast. An example of a breast cancer cell that can be detected by the subject method includes triple negative cancer cells that are negative for Her2/neu, estrogen receptor, and progesterone receptor (Pal S K et al. (2009) *Maturitas* 63:269-274; Ahmad A et al. (2009) *Journal of Cellular Biochemistry* 108:916-925). Other cancer that can be detected include cancers in the ovaries, prostate, testes, colon, rectum, lung, brain, blood, bone, marrow, or any other organ or tissue in the body, including but not limited to leukaemias, fibrosarcomas, and glioblastomas.

Such diagnostics can be useful to identify patients amenable to the therapies disclosed herein, and/or to monitor response to therapy.

Suitable immunodiagnostic techniques include, but are not necessarily limited to, both in vitro and in vivo methods (e.g. imaging). The phrase "in vivo imaging" as used herein refers to methods of detecting the presence of a detectable protein (e.g. detectably labeled 3C6) in whole, live mammal. Optically detectable, such as fluorescent antibodies and luciferases-conjugated antibodies, or radioactively labeled agents may be detected by in vivo imaging. In vivo imaging may be used provide 2-D as well as 3-D images of a mammal. Charge-coupled device cameras, photodiodes, avalanche photodiodes, photomultiplier tubes, CMOS, or 3D tomographers may used to carry out in vivo imaging. For example, Burdette J E (2008) *Journal of Mol. Endocrin.* 40: 253-261 reviews the uses of computed tomography, magnetic resonance imaging, ultrasonography, positron emission tomography, single-photon emission computed tomography, etc., for in vivo imaging. Methods for using a detectable label for real-time imaging of luciferase expression in live animals can be readily adapted for use in the subject methods disclosed herein (e.g., Greer L F et al. (2002) *Luminescence* 17: 43-74). In vivo imaging of fluorescent proteins in live animals is described in, e.g., Hoffman (2002) *Cell Death and Differentiation* 9:786-789. In some embodiments, in vivo imaging may be performed by detecting a label that emits light at a wavelength designed to penetrate living tissue. Such labels include long wavelength emitting fluorescent dyes or proteins such as infrared and near infrared dyes or proteins including but not limited to dyes or proteins that emit in the range of about 600 nm to about 800 nm, about 650 nm to about 800 nm, or about 700 nm to about 800 nm. Alternatively, labels designed to emit light that penetrates living tissue may include non fluorescent reagents including but not limited to red-shifted luciferases.

In vivo imaging can also involve computed tomography, magnetic resonance imaging, ultrasonography, positron emission tomography, single-photon emission computed tomography (SPECT), etc. (See Burdette J E (2008) *Journal of Mol. Endocrin.,* 40: 253-261 for detail). SPECT can also be used with an integrated x-ray CAT (CT) scanner (SPECT/CT) in the subject methods. The information from many in vivo imaging methods as those described above can provide 3D distribution of the antibodies in the subject. See Example 14 for more detail.

Where the cell detected using the subject method is in vivo, the method can determine the presence or absence of a particular uPAR-positive cell and/or the location of the uPAR-positive cell in a patient. For example, the subject method can help determine if a cancer cell positive for uPAR has migrated away from the original tumor, the presence or absence of a cancer cell positive for uPAR in the lymph nodes, and/or can help identify lymph nodes containing uPAR-positive cells. In some embodiments, the method may be used to track the progress of anti-cancer treatments including anti-cancer treatments directed toward uPAR positive cancer cells, for example by detecting any decrease or increase in tumor size in vivo. The method can involve administering the subject antibody via local injection, e.g. at a tumor site or site suspected of having cells expressing uPAR or by administering the antibody systemicly including but not limited to infusion (e.g. arterial or venous infusion), or injection (e.g. intravenous, intraarterial, intrathecal, intreacranial, subcutaneous, intramuscular, or other method of injection known in the art).

Where the methods are in vitro, the biological sample can be any sample in which uPAR may be present, including but not limited to tissues, whole cells, and extracts thereof. For example, the assay can involve detection of uPAR on cells in a histological tissue sample. For example, the tissue sample may be fixed (e.g., by formalin treatment) and may be provided embedded in a support (e.g., in paraffin) or frozen unfixed tissue.

Assays can take a wide variety of forms, such as competition, direct reaction, or sandwich type assays. Examples of assays include Western blots; agglutination tests; enzyme-labeled and mediated immunoassays, such as enzyme-linked immunosorbent assays (ELISAs); biotin/avidin type assays; radioimmunoassays; immunoelectrophoresis; immunoprecipitation, fluorescence activated cell sorting, and the like. The reactions generally include detectable labels such as fluorescent, chemiluminescent, radioactive, enzymatic labels or dye molecules, or other methods for detecting the formation of a complex between antigen in the sample and the antibody reacted therewith.

The assays can involve separation of unbound antibody in a liquid phase from a solid phase support to which antigen-antibody complexes are bound. Solid supports which can be used include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Where a solid support is used, the solid support is usually first reacted with a solid phase component (e.g., an anti-uPAR antibody) under suitable binding conditions such that the component is sufficiently immobilized to the support. Sometimes, immobilization to the support can be enhanced by first coupling the antibody to a protein with better binding properties, or that provides for immobilization of the antibody on the support with out significant loss of antibody binding activity or specificity. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind antibodies to a support include polysaccharides, polylactic acids, polyglycolic acids, polymeric amino acids, amino acid copolymers, and the like, with the proviso that the molecule used to immobilize the antibody does not adversely impact the ability of the antibody to specifically bind antigen. Such molecules and methods of coupling these molecules to the antibodies are well known to those of ordinary skill in the art.

After reacting the solid support with the solid phase component, any non-immobilized solid-phase components are removed from the support by washing, and the support-bound component is then contacted with a biological sample suspected of containing uPAR under suitable binding conditions.

After washing to remove any non-bound ligand, a secondary binder moiety is added under suitable binding conditions, wherein the secondary binder is capable of associating selectively with the bound ligand. The presence or absence of the secondary binder can then be detected using techniques well known in the art.

Alternatively, antibodies may be coupled to the beads non-covalently for example through contacting beads or other solid surface covalently attached to protein-A, protein-G, protein-L, or an antibody that recognizes the Fc region of one or more of the subject antibodies with one or more of the subject antibodies. The beads or other solid surface may then be contacted with the tissue, cell or extract to be tested, alternatively washed, collected (e.g. by centrifugation), and analyzed to determine the presence or absence of antibody-antigen complexes.

An ELISA method can be used, wherein the wells of a microliter plate are coated with a subject anti-uPAR antibody. A biological sample containing or suspected of containing uPAR (e.g., a tumor cell expressing active uPAR), is then added to the coated wells. After a period of incubation sufficient to allow antibody binding, the plate(s) can be washed to remove unbound moieties and a detectably labeled secondary binding molecule added. The secondary binding molecule is allowed to react with any captured antigen, the plate washed and the presence or absence of the secondary binding molecule detected using methods well known in the art.

Where desired, the presence or absence of bound uPAR from a biological sample (e.g., uPAR-expressing cells) can be readily detected using a secondary binder comprising an antibody directed against the antibody ligands. For example, a number of anti-bovine, anti-rabbit, anti-equine, anti-rat, anti-mouse, and anti-human immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the antibodies and uPAR form complexes under precipitating conditions. For example, the antibody can be attached to a solid phase particle (e.g., an agarose bead or the like) using coupling techniques known in the art, such as by direct chemical or indirect coupling. The antibody-coated particle is then contacted under suitable binding conditions with a biological sample suspected of containing uPAR to provide for formation of particle-antibody-uPAR complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

Assays can also be conducted in solution by fluorescence activated cell sorting FACS. For example, a biological sample known to comprise, or suspected of comprising, uPAR may be contacted with an antibody of the present invention. The subject antibody may be directly labeled (e.g. fluorescently labeled) or indirectly labeled (e.g. via a secondary antibody) as described herein or generally known in the art. The biological sample may then be counted, and in some cases sorted with a FACS machine. In some cases, fixed cells may be counted or sorted, in other cases, live cells may be counted or sorted.

The test sample used in the diagnostics assays can be any sample in which uPAR may be present, including but not limited to, cells and tissues, and extracts thereof. In some embodiments, particularly as in embodiments involving detection of cancer cells, it may be desirable to conduct the assay using a sample from the subject to be diagnosed that contains intact, living cells. uPAR detection can then be assessed on an extracellular surface of the cells.

Diagnostic assays can also be conducted in situ. For example, anti-uPAR antibodies can be detectably labeled, administered to a subject suspected of having a cancer characterized by cell surface expression of uPAR, and bound detectably labeled antibody detected using imaging methods available in the art, including but not limited to those in vivo imaging methods described herein.

The diagnostic assays described herein can be used to determine whether a subject has a cancer that is more or less amenable to therapy using antibody-based therapy, as well as monitor the progress of treatment in a subject. It also may be used to assess the course of other combination therapies. Thus, the diagnostic assays can inform selection of therapy and treatment regimen by a clinician.

UPAR can be detected by detection of specific binding of an antibody, e.g., a monoclonal antibody (mAb) that has the antigen-binding specificity of antibodies as those listed in FIG. 1. For example, the 3C6-reactive antigen, 2E9-reactive antigen, and/or 2G10-reactive antigen may be present on the cell surface of a cancer cell. The antigen can also be detected in a permeabilized test cell. For example, a test cancer cell that exhibits a pattern of staining with a 3C6 antibody (or an antibody having the antigen binding specificity of 3C6) that is distinct from a pattern of antibody staining in a normal cell is identified as a cancerous cell that exhibits a 3C6-reactive antigen. Such cancers are thus amenable to therapy with an antibody that specifically binds the 3C6-reactive antigen (e.g., the 3C6).

The above-described assay reagents, including the antibodies generated by immunization with uPAR according to the methods described previously, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Therapeutic Methods

The uPAR-binding agents (e.g. antibodies) of the present disclosure can find use as therapeutic for treatment of proliferative disorders that are mediated by uPAR-expressing cells. For example, one or more uPAR-binding agents (e.g. antibody) can be used in a therapy for a uPAR-expressing cancer (including prevention and post-diagnosis therapy) or diagnostics for cancers in which cancer cells express uPAR. Subjects having, suspected of having, or at risk of developing a uPAR-expressing cancer are contemplated for therapy and diagnosis described herein. Samples obtained from such subject are likewise suitable for use in the methods of the present disclosure.

By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease, e.g., so as to decrease tumor load, and/or to decrease the cancer metastases. Such treatment also includes situations where the pathological condition, or the progression of a pathological condition towards a more advanced disease state, or at least symptoms associated therewith, is reduced, or slowed down. In some cases, treatment includes situations wherein the mean time for survival between a patient population undergoing treatment comprising the administration of one or more subject antibodies and a control population not undergoing treatment is greater. In some cases, the increase in mean time for survival may be statistically significant.

A variety of hosts are treatable according to the methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans. In some cases, the host may be a rodent (e.g. mouse, rat, or guinea pig) that is athymic, nude, or otherwise immune impaired. In some cases, the host may represent a xenotrophic cancer model in which human or other mammalian cancer cells from another species are introduced into the host, and then one or more subject antibodies are administered to treat the resulting tumor.

In the methods of cancer treatment, administering of one or more agents (e.g. antibodies) specific for uPAR facilitates a reduction in proliferation of cancerous cells and/or in inhibition of metastasis of cancer cells exposed to the antibody. The method involves administering to the subject an effective amount of a pharmaceutically acceptable formulation that contains one or more agents (e.g. antibodies) specific for uPAR. The agent can have the effect of retarding or otherwise arresting cell growth and/or metastasis. The effects of the agent on cancer cells can be dose dependent, and thus adjustable.

In a related embodiment, the subject being treated possesses cells expressing overly active or overly abundant uPAR relative to a noncancerous cell. The uPAR can be expressed on the cell surface, such as on a cancer cell. This aspect can be beneficial in the context of the methods of the present disclosure in that cells expressing or presenting uPAR can be more amenable to treatment with a binding-antibody of the present disclosure. The antibody can be administered to a subject, for example, where therapy is initiated at a point where presence of the uPAR is not detectable, and thus is not intended to be limiting. It is also possible to initiate antibody therapy prior to the first sign of disease symptoms, at the first sign of possible disease, or prior to or after diagnosis of a disease.

Cancer

The uPAR-binding agent (e.g. antibody) compositions may be used in an anti-cancer therapy in treatment of cancers that express uPAR on an extracellularly accessible cell surface.

The presence of uPAR and other members of the plasminogen activation system in normal human tissue appear to be transient and low abundance. It is prevalent only in abnormal cells, such as cancer cells including metastasizing cancer cells. Since expression of high levels of uPAR exists predominantly in cancer cells, treatment with subject compositions can be used to detect the presence and localize cancer growth and can block cancer growth. It should be noted that while uPAR may be expressed at higher levels on a cancer cell compared to a non-cancerous cell, this is not a limitation of the therapies disclosed herein.

The subject compositions described herein can be administered to a subject (e.g. a human patient) to, for example, reduce proliferation cancerous cells, e.g., to reduce tumor size, reduce tumor load, decrease metastatic potential (e.g. reduce cancer cell migration) and/or improve the clinical outcome in patients. In other words, the compositions can be used to reduce cell growth, cell division, and/or decrease the invasiveness of cancer cells, e.g., by decreasing any signaling events leading up to cancer metastasis. Some ways of decreasing cancer invasiveness involve reducing the ability of cancer cells to leave the original cancerous site, reducing the ability of cancer cells to migrate, and the ability of cancer cells to adhere to areas of the body after migration.

Cancers particularly amenable to antibody therapy can be identified by examining markers of cellular proliferation (e.g., Ki-67 antigen) and/or by examining the presence/accessibility of the uPAR bound by one or more subject antibodies (e.g. 3C6, 2G10, 2E9) or by other antibodies specific for uPAR (e.g., as in an in vitro assay).

Types of Cancer

Where the anti-cancer therapy comprises administration of an antibody composition described previously, the anti-cancer therapy can be particularly directed to cancer cells. For example, one or more subject antibodies (e.g. 3C6, 2G10, 2E9) may bind a uPAR-expressing cancer cell. As illustrated in the examples, 3C6, 2G10, and 2E9 are highly effective in binding as well as inhibiting various functional activities of uPAR.

Examples of cancers presenting uPAR include but not limited to cancer cells of epithelial origin. Some examples are squamous carcinomas, hematological neoplasms, gastric cancer, lymph node, colorectal cancer, pancreatic cancer, hepatic cancer, and immunological disorders. Other more specific examples of cancer include breast (e.g. triple negative breast tumor), ovarian, prostate, lung, leukaemias, fibrosarcomas, glioblastomas, and prostate cancer, as discussed above.

Combination Therapies

The therapeutic methods described herein can include administration of a uPAR agent (e.g. antibody) in combination with one or more other therapies. The combination therapy below can provide for additive or synergistic benefits relative to a regimen in which only one therapy is administered.

An example of combination therapy involves administering more than one type of agent (e.g. antibody) to a subject. As described above for pharmaceutical compositions, the therapeutic method may involve administering at least one, at least two, at least three or more different types of antibodies simultaneously or sequentially, including for example one or more subject antibodies. The antibodies may differ in the epitopes of uPAR to which they bind. The method, for example, may involve administering antibodies from clone 3C6 and antibodies from clone 2G10 and/or 2E9 to a subject in need of therapy. The antibodies may also bind the same or overlapping epitopes of uPAR. The method for example may involve administering two or more antibodies that each inhibit the interaction between uPAR and uPA, or two or more antibodies that each inhibit the interaction between uPAR and an integrin, or two or more antibodies that each inhibit the interaction between uPAR and vitronectin, or two or more antibodies that each inhibit the interaction between uPAR and uPARAP, or the method may involve administering two or more antibodies that bind to uPAR but do not inhibit one or more of the foregoing interactions, or any combination thereof.

The combination therapy method can treat cancer in various ways. As noted above for the subject composition, the subject method can employ one or more agents that inhibit one or more uPAR signaling pathways. Where more than one signaling pathways are targeted by the agents, there can be a synergistic inhibition of cell adhesion, proliferation, and/or migration of cancer cells. For example, one signaling pathway that can be inhibited by a binding agent is mediated by uPA binding to uPAR, while another pathway is mediated by integrin (e.g. a β1 integrin, such as such as α5β1 or α3β1) binding to uPAR.

Additional standard anti-cancer therapeutics that may or may not be administered in conjunction with a subject antibody, include but not limited to immunotherapy, chemotherapeutic agents and surgery (e.g., as those described further below). In addition, therapeutic administration of a subject antibody can also be post-therapeutic treatment of the subject with an anti-cancer therapy, where the anti-cancer therapy can be, for example, surgery, radiation therapy, administration of chemotherapeutic agents, and the like. Cancer therapy using a subject antibody in combination with immunotherapy that employs anti-uPAR antibodies is of particular interest.

For example, a subject antibody can be administered in combination with one or more chemotherapeutic agents (e.g., cyclophosphamide, doxorubicin, vincristine and prednisone (CHOP)), and/or in combination with radiation treatment and/or in combination with surgical intervention (e.g., pre- or post-surgery to remove a tumor), radiation therapy, bone marrow transplantation, biological response modifier treatment, and certain combinations of the foregoing. Radiation therapy includes, but is not limited to, X-rays or gamma rays that are delivered from either an externally applied source such as a beam, or by implantation of small radioactive sources.

Chemotherapeutic agent's suitable for use in combination (formulated either separately or with a uPAR antibody) can include a variety of agents. Examples of such agents are discussed in more detail below.

Chemotherapeutic agents may be non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (CYTOXAN™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (TAXOL®), docetaxel (TAXOTERE®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (TAXOL®), TAXOL® derivatives, docetaxel (TAXOTERE®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and progestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and ZOLADEX®. Estrogens stimulate proliferation and differentiation; therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); IRESSA® (ZD 1839, 4-(3-chloro-4-fluorophenylamino)-7-methoxy-6-(3-(4-morpholinyl)propoxy)quinazoline); etc.

Proteosome Inhibitors, and Kinase Inhibitors,

"Taxanes" include paclitaxel, as well as any active taxane derivative or pro-drug. "Paclitaxel" (which should be understood herein to include analogues, formulations, and derivatives such as, for example, docetaxel, TAXOL®, TAXOTERE® (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art, or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., TAXOTERE docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives; piperazino; taxane derivatives; 6-thio derivatives; sulfenamide derivatives; and taxol derivative. It may further include prodrugs of paclitaxel.

Where a combination therapy is administered, the therapy or treatment other than administration of antibody composition can be administered anywhere from simultaneously to up to 5 hours or more, e.g., 10 hours, 15 hours, 20 hours or more, prior to or after administration of a subject antibody. A subject antibody and other therapeutic intervention can be administered or applied sequentially, e.g., where a subject antibody is administered before or after another therapeutic treatment. Alternatively, a subject antibody and other therapy are administered simultaneously, e.g., where a subject antibody and a second therapy are administered at the same time, e.g., when the second therapy is a drug it can be administered along with a subject antibody as two separate formulations or combined into a single composition that is administered to the subject. Regardless of whether administered sequentially or simultaneously, as illustrated above, the treatments are considered to be administered together or in combination for purposes of the present disclosure.

Dosage

In the methods, an effective amount of an agent (e.g. a uPAR antibody) is administered to a subject in need thereof. For example, in some embodiments, a uPAR-binding agent can facilitate inhibition of growth and/or proliferation of a uPAR-expressing cancer cell. The amount administered can vary depending upon the goal of the administration, the health and physical condition of the individual to be treated, age, the degree of resolution desired, the formulation of a subject agent, the treating clinician's assessment of the medical situation, and other relevant factors. It is expected that the amount will fall in a relatively broad range that can be determined through routine trials. For example, the amount of subject agent employed to inhibit cancer cell growth is not more than about the amount that could otherwise be irreversibly toxic to the subject (i.e., maximum tolerated dose). In other cases the amount is around or even well below the toxic threshold, but still in an effective concentration range, or even as low as threshold dose.

Individual doses are typically not less than an amount required to produce a measurable effect on the subject, and may be determined based on the pharmacokinetics and pharmacology for absorption, distribution, metabolism, and excretion ("ADME") of the antibody, and thus based on the disposition of the composition within the subject. This includes consideration of the route of administration as well as dosage amount, which can be adjusted for parenteral (applied by routes other than the digestive tract for systemic or local effects) applications, for example. For instance, administration of a subject antibody is typically via injection and often intravenous, intramuscular, intratumoral, intracranial, intraarterial, intraocular, intrathecal, or a combination thereof.

A uPAR-binding agent (e.g. antibody) may be administered by infusion or by local injection. It also can be administered prior, at the time of, or after other therapeutic interventions, such as surgical intervention to remove cancerous cells. As noted above, a uPAR antibody can also be administered as part of a combination therapy, in which at least one of an immunotherapy, a cancer chemotherapy or a radiation therapy is administered to the subject (as described in detail above).

Disposition of the agent and its corresponding biological activity within a subject is typically gauged against the fraction of agent present at a target of interest. For example, an antibody once administered can accumulate with uPAR or other biological target that concentrates the material in cancer cells and cancerous tissue. Thus dosing regimens in which the antibody is administered so as to accumulate in a target of interest over time can be part of a strategy to allow for lower individual doses. This can also mean that, for example, the dose of antibody that are cleared more slowly in vivo can be lowered relative to the effective concentration calculated from in vitro assays (e.g., effective amount in vitro approximates mM concentration, versus less than mM concentrations in vivo).

As an example, the effective amount of a dose or dosing regimen can be gauged from the $IC_{50}$ of a given antibody for inhibiting or binding uPAR. By "$IC_{50}$" is intended the concentration of a drug required for 50% inhibition in vitro. Alternatively, the effective amount can be gauged from the $EC_{50}$ of a given antibody concentration. By "$EC_{50}$" is intended the plasma concentration required for obtaining 50% of a maximum effect in vivo.

In general, with respect to the uPAR-binding agents of the present disclosure, an effective amount is usually not more than 200× the calculated $IC_{50}$. Typically, the amount of an antibody that is administered is less than about 200×, less than about 150×, less then about 100× and many embodiments less than about 75×, less than about 60×, 50×, 45×, 40×, 35×, 30×, 25×, 20×, 15×, 10× and even less than about 8× or 2× the calculated $IC_{50}$. In one embodiment, the effective amount is about 1× to 50× of the calculated $IC_{50}$, and sometimes about 2× to 40×, about 3× to 30× or about 4× to 20× of the calculated $IC_{50}$. In other embodiments, the effective amount is the same as the calculated $IC_{50}$, and in certain embodiments the effective amount is an amount that is more than the calculated $IC_{50}$.

An effective amount may not be more than 100× the calculated $EC_{50}$. For instance, the amount of antibody that is administered is less than about 100×, less than about 50×, less than about 40×, 35×, 30×, or 25× and many embodiments less than about 20×, less than about 15× and even less than about 10×, 9×, 8×, 7×, 6×, 5×, 4×, 3×, 2× or 1× than the calculated $EC_{50}$. In one embodiment, the effective amount is about 1× to 30× of the calculated $EC_{50}$, and sometimes about 1× to 20×, or about 1× to 10× of the calculated $EC_{50}$. In other embodiments, the effective amount is the same as the calculated $EC_{50}$, and in certain embodiments the effective amount is an amount that is more than the calculated $EC_{50}$.

Effective amounts can readily be determined empirically from assays, from safety and escalation and dose range trials, individual clinician-patient relationships, as well as in vitro and in vivo assays such as those described herein and illustrated in the Experimental section, below.

The $IC_{50}$ may be calculated by inhibiting the agent binding to uPAR (e.g. uPAR alone or complexed uPAR, such as uPAR with integrins) in vitro. This aspect can be carried out by assessing the ability of the agent of interest to inhibit 3C6 antibody binding to uPAR. In general, the procedure is carried out by standard ELISA in which the plates are coated with uPAR as described in the examples at a concentration of about 1 μg/ml, and then processed and employed as described in the experimental examples to determine inhibition of antibody binding and the $IC_{50}$. These agents and others suitable for various aspects of this purpose can be employed.

Routes of Administration

In practicing the methods, routes of administration (path by which a subject agent is brought into a subject in need of therapy or diagnosis) may vary, where representative routes of administration for a subject antibody are described in greater detail below. A subject agent alone or in combinations described above can be administered systemically (e.g., by parenteral administration, e.g., by an intravenous route) or locally (e.g., at a local tumor site, e.g., by intratumoral administration (e.g., into a solid tumor, into an involved lymph node in a lymphoma or leukemia), administration into a blood vessel supplying a solid tumor, etc.).

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The formulations of the present disclosure can also be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Suppository formulations are also provided by mixing with a variety of bases such as emulsifying bases or water-soluble bases. Formulations suitable for vaginal administration may be presented as pessaries, tampons, creams, gels, pastes, foams.

Unit dosage forms for rectal administration such as syrups, elixirs, and suspensions may be provided wherein each dosage unit contains a predetermined amount of the composition containing the antibody compositions. Similarly, unit dosage forms for injection or intravenous administration may comprise the antibody in a composition as a solution in sterile water, normal saline or another pharmaceutically acceptable carrier.

The term “unit dosage form,” as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms depend on the particular compound employed and the effect to be achieved, and the pharmacodynamics associated with each compound in the host.

Methods of Screening

A screening method of the present disclosure can be employed to screen for a binding-agent that binds uPAR. The method can involve contacting uPAR with a candidate agent and detecting binding of the candidate agent with uPAR. The method may also involve contacting uPAR with a candidate agent and contacting uPAR with one or more known ligands of uPAR before, after or during the step of contacting uPAR with a candidate agent and then detecting the binding of either the candidate agent with uPAR or the one or more ligands with uPAR or detecting the binding of both the candidate agent and the one or more uPAR ligands. The method may also involve the use of libraries of constructs encoding antibodies, aptamers, and/or libraries of small molecules to screen for a uPAR-binding agent. The binding agent may be selected for its potent inhibition of uPAR activities, inhibition of the expression of mature uPAR, and/or inhibition of the binding affinity for uPAR-interacting proteins (ligands and/or integrins, e.g. β1 integrins). The method may be executed according to methods known in the art.

Briefly, uPAR (e.g. uPAR alone or uPAR complexed with its ligand and/or integrins) is contacted with a candidate agent. The binding of the candidate agent to uPAR is measured to see if there is a binding affinity for uPAR. The ability of the candidate agent to disrupt uPAR binding to ligands (e.g. uPA, vitronectin, and/or uPARAP) or to the members of the integrin family is also assessed. Candidate agents that are effective in disrupting binding of uPAR to its interacting partners (e.g. β1 integrins) are selected to be potential agents to be used in diagnostic and therapeutic compositions and methods of use. Candidate agents that can disrupt binding of uPAR to its interacting partners encompass those that can decrease the binding affinity of uPAR to its interacting partners either competitively or noncompetitively.

UPAR that may be used to screen for potential agent include uPAR as described previously. Exemplary uPAR to be used in the subject screening methods include but are not limited to full-length uPAR, mature uPAR, fragments of uPAR, such as a fragment of uPAR lacking the GPi anchor, uPAR alone or uPAR bound to one or more ligand or to members of the integrin family.

In an example of a screening method, uPAR (e.g. uPAR in the presence or absence of uPA or β1 integrins) may be immobilized on an ELISA plate or on beads through a covalent or non-covalent interaction, such as hydrophobic adsorption, biotin-avidin interaction, and $Ni^{2+}$-6×His interaction. A population of candidate agents is then incubated with the immobilized uPAR, washed, and recovered. During selection, the bound candidate is recovered and identified. Multiple successive selection rounds ensure a selection of a candidate that acts as a specific binding agent for uPAR. Other methods such as plasma resonance, western blot, functional assays (e.g. invasiveness, protease activity, and/or phosphorylation of downstream targets), fluorescence activated cell sorting, etc. can also be used to screen and select for agents that can bind uPAR, or bind uPAR and inhibit its interaction to one or more ligands or β1 integrins. Where the method involves protease assay, a fluorgenic peptide or colorimetric substrate (e.g. spectrazyme UK) may be used in accordance with methods known in the art (e.g. Zimmerman et al. (1978) *PNAS* 75:750-753). By detecting a change in the amount of substrate cleaved or the rate at which the substrate is cleaved, an agent would be selected based on its ability to change the amount of protease activity bound to uPAR. Various assays employed in the screening method can involve comparing binding and/or activity of uPAR in the presence or absence of the candidate agents.

Candidate uPAR-binding agents may also be engineered so that the agent contains sites that are known to have affinity for either the ligand-binding site or the integrin-binding site.

Also contemplated by the present disclosure is a library of nucleic acid constructs encoding the candidate uPAR-binding agents described herein. The library encodes a plurality of candidate protease binding agents that may have one or more polypeptide regions in common with any antibody disclosed herein (e.g. framework region or a heavy chain CDR3)

Kits & Systems

Also provided are kits and systems that may find use in practicing the methods, as described above. For example, kits and systems may include one or more of the compositions described herein, such as an anti-uPAR antibody (e.g. 3C6, 2E9, or 2G10 or any antibody described herein), a nucleic acid encoding the same (especially a nucleic acid encoding a CDR of a heavy and/or light chain of 3C6, 2E9, or 2G10), or a recombinant cell containing the same. Other optional components of the kit include: buffers, etc., for administering the anti-uPAR antibody, and/or for performing a diagnostic assay. The recombinant nucleic acids of the kit may also have restrictions sites, multiple cloning sites, primer sites, etc to facilitate their ligation to constant regions of non-3C6, 2E9 or 2G10 encoding nucleic acids. The various components of the kit may be present in separate containers or certain compatible components may be precombined into a single container, as desired.

The kits and systems for practicing the methods may include one or more pharmaceutical formulations that include the antibody compositions described herein. As such, the kits may include a single pharmaceutical composition present as one or more unit dosages. In yet other embodiments, the kits may include two or more separate pharmaceutical compositions.

In addition to the above components, the kits may further include instructions for practicing the methods. These instructions may be present in the kits in a variety of forms, one or more of which may be present in or on the kit. One form in which these-instructions may be present is as printed information on a suitable medium or substrate, e.g., a piece or pieces of paper on which the information is printed, in or on the packaging of the kit, in a package insert, etc. Yet another means would be a computer readable medium, e.g., diskette, CD, flash drive, thumb drive, etc., on which the information has been recorded. Yet another means that may be present is a website address which may be used via the internet to access the information at a removed site. Any convenient means may be present in the kits.

A kit may be provided for use in treating a host suffering from a cellular proliferative disease. This kit includes a pharmaceutical composition comprising antibody specific for uPAR, and instructions for the effective use of the pharmaceutical composition in a method of treating a host suffering from a cancerous condition by inhibiting the growth and/or metastasis of a cancer cell in a subject. Such instructions may include not only the appropriate handling properties, dosing regiment and method of administration, and the like, but can further include instructions to optionally screen the subject for uPAR associated with the disease. This aspect can assist the practitioner of the kit in gauging the potential responsiveness of the subject to treatment with an antibody of the present disclosure, including timing and duration of treatment relative to the type and growth stage of the cancer. Thus in another embodiment, the kit may further include an antibody or other reagent, such as 3C6, 2E9, and/or 2G10, for detecting uPAR on an extracellularly accessible surface of a cancer cell. The kit may also include an antibody that contains a conjugate with a detectable label, such as a fluorophore.

The term "system" as employed herein refers to a collection of antibodies described herein and one or more second therapeutic agents, present in single or disparate compositions that are brought together for the purpose of practicing the methods. For example, separately obtained antibody specific to uPAR and chemotherapy dosage forms brought together and co-administered to a subject are a system according to the present disclosure.

The following examples further illustrate the present invention and should not be construed as in any way limiting its scope.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Materials and Methods

The following methods and materials were used in the Examples below.

uPAR expression and purification. Human soluble uPAR cDNA (residues 1-277) was ligated into the insect cell expression vector pACgp67 (BD Biosciences). pACgp67 and Baculogold DNA (BD Biosciences) were co-transfected into *Spodoptera frugiperda* 9 (Sf9) cells using Lipofectamine™ (Invitrogen) according to the manufacturer's protocol. Infected cell culture supernatant was harvested seven days post-transfection.

uPAR was captured by antibody affinity chromatography, eluted, and then dialyzed overnight before purificatopm by fast protein liquid chromatography on a MonoQ (GE Life Sciences) column using a linear gradient from 0 to 1 M NaCl for elution.

Phage Display Library Construction. A fully human naïve Fab phage display library was constructed using methods described by de Haard et al. (1999) *J Biol Chem* 274:18218-18230. Briefly, peripheral blood lymphocyte RNA was converted to cDNA. The resulting library was cloned into a phagemid vector, which fuses a C-terminal hexa-histidine and c-myc tag to the heavy chain. Large-scale phage rescue was performed using M13K07 helper phage.

Phage Display Panning. Human soluble uPAR was immobilized to a Nunc Maxisorp™ 96-well microplate (eBioScience) at 10 μg/ml in 50 mM sodium carbonate pH 9.5 and unbound uPAR was removed by washing. uPAR-coated wells were then blocked with milk, washed, and a pre-blocked aliquot of the phage library was divided between the wells. Unbound phage were washed away, and bound phage were recovered by adding *Escherichia coli* (*E. coli*) TG1 cells. Infected TG1 cells were spread onto selection plates, grown overnight, and harvested by plate scraping. Phage were amplified with M13K07 helper phage infection in liquid culture. Fab-displaying phage were harvested from the culture supernatant and concentrated by PEG precipitation.

The $2^{nd}$ and $3^{rd}$ rounds of panning were conducted similarly to the $1^{st}$ round, but were made increasingly stringent to remove weakly bound phage.

Expression of Fab into culture supernatants. Phage-infected *E. coli* TG1 colonies were grown in selection media, and Fab expression was induced by the addition of isopropyl β-D-1-thiogalactopyranoside (IPTG; 1 mM final) to cultures showing log phase growth. Cultures were shaken overnight to induce periplasmic Fab expression, a minor portion of which leaks into the culture supernatant. Following overnight incubation, TG1 culture supernatants containing leaked Fabs were collected by centrifugation.

Preparation of periplasmic fraction. Cell pellets from phage-infected TG1 cultures grown at the 96-well plate scale and induced for Fab expression by IPTG, were resuspended in 50 μl 100 mM Tris pH 8.0, 25% glucose, 100 μg/ml hen egg white lysozyme and shaken at room temperature for 30 minutes. 300 μl of ice-cold water was then added and mixed with vigorous pipeting. The periplasmic fraction was the clarified by centrifugation.

Fab purification. Individual Fab clones were expressed in *E. coli* BL21 cells (as described for TG1 cells). Periplasmic fractions were purified by immobilized nickel chelate chromatography using Chelating Sepharose™ (GE LifeScience) according to the manufacturer's prototol.

Purified protein was analyzed by SDS-PAGE, and the concentration was estimated with the BCA™ Protein Assay Kit (Pierce), using bovine serum albumin (BSA) standards. Each Fab was analyzed for expression by Western Blot using a Penta-His horseradish peroxidase (HRP) conjugate antibody (Qiagen) according to the manufacturer's protocol. The Western Blot was visualized on a Typhoon imager (GE LifeScience) using the ECL Plus™ chemiluminescent reagent (GE LifeScience).

uPAR ELISA. uPAR-binding Fabs were detected on a Nunc Maxisorp™ 96-well plate coated with 50 μl of 1 μg/ml uPAR. Fabs (either culture supernatant, periplasmic fraction, or purified protein at 22.5 μg/ml) were applied to the plate's wells, which were then washed. Bound Fabs were detected using 100 μg/ml of HRP-conjugated anti-myc antibody clone 9E10 (Roche). Three wells not coated with uPAR were included to control for nonspecific Fab binding. For ELISA assays using culture supernatants, bound 9E10-HRP was detected using 1-Step™ Turbo-TMB ELISA (Pierce) for endpoint analysis at 450 nm according to the manufacturer's protocol. For all other experiments, bound 9E10-HRP was detected as the rate of change of the absorbance at 650 nm in the presence of TMB substrate.

Sequence Analysis. The heavy and light chain expression cassettes of all 36 uPAR-binding clones were sequenced. The complementarity determining regions (CDRs) of the heavy and light chain sequences were aligned on the ClustalW2 server (Larkin et al. (2007) *Bioinformatics* 23:2947-2948).

Competitive ELISA. 95 μl of each Fab was combined with 6 nM high molecular weight uPA (HMW-uPA) (American Diagnostica). The resulting mixture was incubated with the uPAR-coated microplate wells described in the previous section. Wells not coated with uPAR were included to control for any nonspecific binding of HMW-uPA. Wells coated with uPAR and incubated against all Fabs without HMW-uPA were included to control for nonspecific protease activity. Maximal uPA binding was determined by incubating HMW-uPA with uPAR-coated wells, without any Fab. Unbound Fabs and HMW-uPA were removed by washing. The amount of bound HMW-uPA was measured by assaying proteolytic activity in the treated wells using the chromogenic uPA substrate Spectrazyme® UK (American Diagnostica) and monitoring the rate of change of the absorbance at 405 nm. The wells were further assayed to detect the presence of bound Fab using 9E10-HRP as described in the previous section.

uPA activity in presence of Fabs. Fabs were tested for direct inhibition of uPA in two ways. First, 1 μg/ml of HMW-uPA was incubated in uPAR-coated plates; unbound HMW-uPA was removed by washing, and Fabs were added to the wells at 25 μg/ml. The activity of HMW-uPA in the presence and absence of Fab was measured as described above. Second, 10 nM HMW-uPA and low molecular weight uPA (LMW-uPA) (American Diagnostica) were incubated in a microtiter plate in the presence and absence of 450 nM Fab. The activity of HMW- and LMW-uPA was measured in triplicate by assaying proteolytic activity as described above.

Human IgG1 Antibody Expression and Purification. Heavy and light chain Fab sequences were amplified by PCR and separately cloned into vector pTT5-SP-H1, a modification of the pTT5 vector (National Research Council of Canada). Heavy and light chain expression vectors were transformed into NEB Turbo Competent *E. coli* (NEB) and large-scale plasmid preparations were performed using the Pure Yield Plasmid Midiprep system (Promega). The sequences of all full-length antibody expression clones were confirmed.

HEK-293-EBNA1 cells, a generous gift from Yves Durocher of the Canadian National Research Council, were adapted to GIBCO® FreeStyle™ 293 Expression Medium (Invitrogen) supplemented with 50 μg/ml G418. Heavy and light chain encoding pTT5 plasmids were co-transfected into the cells with jetPEI™ (Polyplus) according to the manufacturer's protocol. Cells were incubated for four to five days post-transfection, after which the IgG-containing spent media was harvested. IgGs were purified on a Protein A agarose (Pierce) affinity column, eluted with 100 mM citrate pH 3.0, neutralized, dialyzed overnight against PBS, and stored at 4° C. IgG expression levels were determined using the Easy-Titer Human IgG Assay Kit (Pierce) and spectrophotometric readings at 280 nm.

Surface Plasmon Resonance. The interaction affinities between uPAR and 1A8, 2B1, 2G10, and 2E9 were determined by equilibrium surface plasmon resonance (SPR) using a Biacore 1000. In order to abrogate the effect of avidity, antibodies were immobilized on the surface of a Biacore CM5 chip and soluble uPAR was flowed as the analyte. Four Biacore CM5 chip flow cells were sequentially treated, according to the manufacturer's protocol, with 1-Ethyl-3-[3-dimethylaminopropyl]carbodiimide hydrochloride (EDC) and N-hydroxysuccinimide (NHS). 1A8, 2B1, 2E9 and 2G10 IgGs were each diluted to 5 μg/ml in 10 mM sodium acetate pH 5.0 and then immobilized to separate flow cells to obtain approximately 2700 relative response units. The flow cells were blocked with 1 M ethanolamine pH 8.5 after antibody immobilization. A flow cell on each CM5 chip was immediately treated with 1 M ethanolamine pH 8.5 after EDC/NHS activation to provide a reference surface.

Soluble human uPAR was injected over flow cells at the following concentrations: 450 nM, 225 nM, 112.5 nM, 56.25 nM, 28.13 nM, 14.1 nM, 7 nM, 3.5 nM, 1.8 nM, and 0 nM. Bound uPAR was removed with 10 mM glycine pH 1.5. Instrument response values were recorded and imported into Scrubber2 (BioLogic Software) for analysis. Data were normalized using the double referencing method (26), and analyzed using a one site binding model as implemented in Scrubber2. Response values reached a stable plateau as judged by a change of less than 0.05% over the last minute of injection.

Flow Cytometry. A confluent flask of either HEK 293 cells or HEK 293 uPAR cells was treated with TrypLE Express (Gibco). Harvested cells were re-suspended in Stain Buffer (BD Pharmingen) and either $5\times10^5$ or $1\times10^6$ cells were transferred to tubes for antibody staining. 1A8, 2B1, 2E9, 2G10, and whole human IgG (Sigma) were added to a final concentration of 5 μg/ml. 2G10 and 3C6 Fab were added to a final concentration of 50 μg/ml. All samples were incubated on a rotator at 4° C. for 30 minutes after addition of antibody, harvested by centrifugation, and resuspended in 500 μl of Stain Buffer. The IgG samples were resuspended and incubated with 20 μl of fluorescein isothiocyanate (FITC)-conjugated mouse anti-human monoclonal antibody (BD Pharmingen), while the Fab samples were incubated with Alexa Fluor® 488-conjugated mouse anti-cMyc monoclonal antibody (AbD Serotec). $5\times10^5$ cells were analyzed with a Beckton Dickinson FACSCalibur cytometer. Data analysis was performed with FlowJo version 7.2.4.

Mouse Xenograft Generation. Subcutaneous MCF-7/Luc+ (MCF-7 cells expressing luciferase), and orthotopic MDA-MB-231/Luc+ tumor xenografts were generated using MCF7 and MDA-MB-231-luc breast cancer cell lines. MDA-MB-231-luc cells are MDA-MB-231 cells which were modified to stably express luciferase, so that the tumor can also be imaged via bioluminescent detection of injected luciferin.

Fluorescent labeling of IgG. 2G10 IgG was labeled with Alexa Fluor 680 (Invitrogen, Carlsbad, Calif.) according to manufacturer's protocol. Protein was purified from unreacted dye on a Superdex 75 FPLC column (GE Healthcare, Little Chalfont, UK). Degree of labeling was determined using UV/Vis spectrometry as directed in manufacturer's protocol. An average of fifteen moles of dye per mole of 2G10 IgG was achieved.

Optical imaging of mice. Mice were handled, injected, and imaged as follows. Briefly, Alexa Fluor 680-labeled 2G10 IgG was administered by tail vein injection to achieve ~0.25 nmols IgG per mouse. Images were collected in fluorescent mode on an IVIS 50 using Living Image 2.50.2 software (Caliper Life Sciences, Hopkinton, Mass.) at set intervals. Two mice were imaged, each, for both the uPAR-positive tumors (MDA-MB-231) and uPAR-negative tumors (MCF-7). Bioluminescent images were also obtained as previously described. All in vivo studies were performed as directed under institutional approval.

Adhesion Assay. The cell adhesion assay was performed as described previously (Wei et al. (2007) *J Biol Chem* 282: 3929-3939). Briefly, H1299 cells ($2\times10^5$) were seeded onto fibronectin (FN)-coated (10 μg/ml) plates with or without the anti-uPAR Fabs (10 mg/ml), RGD peptide, or RAD peptide (0.4 mM). Attached cells were fixed with methanol and Giemsa stain was used for colorimetric analysis by measuring the optical density at 550 nm. FN was purchased from Sigma-Aldrich (St. Louis, Mo.). RGD and RAD peptides were purchased from Anaspec (San Jose, Calif.).

ERK Phosphorylation Assays. Serum-starved H1299 cells were washed with 50 mM glycine-HCl, 100 mM NaCl, pH 3.0 for three minutes to remove surface-bound endogenous uPA, and neutralized with 0.5 M HEPES, 0.1 M NaCl pH 7.5 for 10 minutes on ice. Cells were pre-treated with 10 μg/ml of 1A8, 2B1, 2E9, 2G10, or control human IgG for one hour at 37° C. Pro-uPA was added to 10 nM and incubated at 37° C. for five minutes to initiate ERK activation. After incubation, cells were lysed in RIPA buffer (Pierce) supplemented with protease and phosphatase inhibitors (Sigma-Aldrich) and blotted for phospho- and total ERK (Cell Signaling). In the case of FN-stimulated ERK phosphorylation, cells were cultured on a FN- (10 μg/ml) coated surface for 30 minutes before lysis.

Invasion Assays. H1299 human lung cancer cells ($1\times10^5$) were pre-treated with 1A8, 2B1, 2E9, 2G10, or control human IgG (each 10 μg/ml), and 2G10, 3C6, 2G10+3C6 Fab (each 10 μg/ml) for one hour at 37° C. Cells were then seeded on BD Biocoat™ Matrigel™ Invasion Chambers (BD Biosciences) with bottoms pre-coated FN, and then cultured overnight in serum-free DMEM containing 5 mg/ml BSA. Fetal bovine serum was added to the lower chamber. 24 hours later, the Matrigel and cells on the membrane's top chamber side were removed, and cells on the membrane's bottom chamber side were fixed with methanol, stained with Giemsa, extracted in 10% acetic acid, and measured in a plate reader at 595 nm. All assays were performed in triplicate and the data expressed as percent inhibition by the antibodies: % Inhibition$=((OD_{595,\,Ab}-OD_{595,\,Ctrl})/OD_{595,\,Ab})\times100$.

Anti-uPAR Co-immunoprecipitation. H1299 cells ($1\times10^7$) were lysed in Triton lysis buffer (50 mM HEPES, pH 7.5, 150 mM NaCl and 1% Triton X-100) supplemented with protease inhibitors (Sigma) and 1 mM PMSF. Clarified lysates were first incubated with anti-uPAR Fabs (10 μg/ml) at 4° C. for 1 hour, then with Penta-His Antibody (Qiagen) for 1 hour, and finally with 50 ⌠l of mixed Protein A- and Protein G-Agarose beads overnight. The immunoprecipitates were subjected to SDS-PAGE and Western blot analysis for uPAR and 〈V integrin. The anti-uPAR monoclonal antibody (R2) was a kind gift from Michael Ploug (Finsen Lab, Copenhagen, Denmark). The anti-〈V integrin polyclonal antibody was purchased from Chemicon (Temecula, Calif.).

Example 1

Phage Display Identifies uPAR Binding Fabs

Prior to panning, the binding of non-denatured uPAR to a microplate surface was confirmed by detecting the binding of high molecular weight uPA (HMW-uPA) to the uPAR-coated surface. Binding of HMW-uPA was detected by the presence of specific proteolytic activity within a microplate well with the uPA substrate spectrazyme UK after incubating the uPAR-coated plate with HMW-uPA and stringently washing.

Fabs capable of binding human uPAR were obtained after three rounds of panning, in which washes to remove weakly bound Fab-displaying phage were made increasingly stringent. 384 independent clones were evaluated from the final round of panning. To confirm that these Fabs could be expressed in bacteria, culture supernatants (into which a small fraction of Fabs escaped after IPTG addition) were tested for the presence of Fab capable of binding to uPAR. From these 384 clones, 96 were selected for further analysis on the basis of reproducible uPAR binding. Periplasmic protein fraction were then prepared from the 96 clones. With these fractions, ELISA analysis gave stronger, more consistent signals compared to that of culture supernatants. Of the 96 clones, 36 candidates were confirmed as strong binders of uPAR, with an average signal greater than 8-fold over background.

Example 2

Sequence Analysis and Small-Scale Expression Identifies Unique Fabs

The 36 candidates were sequenced and evaluated for expression at the 100 ml culture scale. Sequencing of the heavy and light chain expression cassettes revealed that 22 of the 36 candidates have unique Fab sequences. ClustalW alignment of these sequences yielded a percent identity dendrogram with two distinct groups of antibodies defined by having a κ or λ light chain (FIG. 1, panel A). Several subgroups of highly related sequences are evident within the κ light chain group whereas eight antibodies with a relatively low degree of sequence similarity are evident within the λ light chain group. In Panel A of FIG. 1, the number of identical clones is indicated in parentheses for redundant Fab sequences. The Fab subgroups, defined by their light chain identity (κ or λ), are also labeled. The vertical line indicates the 82% sequence identity threshold. Sequences that branch to the right of the 82% cut-off are considered equivalent.

Alignment of the six complementary determining regions (CDRs) of each unique Fab (FIG. 1, panel B) shows that the CDR sequences determine the subgrouping pattern observed in the dendrogram of FIG. 1, panel A. The lowest pairwise sequence identity between antibody CDRs was 22%. The name of each CDR loop is indicated above the alignment. Fab heavy and light chain protein sequences with greater than 82% sequence identity were grouped together (boxed).

The expression levels of the 22 unique Fabs in *E. coli* were determined after IPTG induction of 100 ml cultures. Histidine-tagged Fabs from the periplasmic fraction were obtained by osmotic shock, purified on a nickel chelating sepharose column, and analyzed for expression by Western blot. Asterisks indicate Fab clones that did not express in *E. coli* Rosetta-gami™ B cells. Small-scale expression of the remaining Fabs, with the exception of 2E9, yielded 250 μg/L of *E. coli* culture. Fab 2E9 expression yields were five fold lower.

Purified Fabs were further characterized by uPAR ELISA. Initial measurements of bound antibody exhibited a large variance between different Fabs, but control experiments measuring uPA binding to immobilized uPAR did not show similar variance suggesting that these differences reflect inherent disparities in binding mode or affinity between different Fabs.

The list of Fabs to further pursue was narrowed by clustering individual clones based on their sequences and bacterial expression abilities. Sequences with a sequence similarity greater than or equal to 82% were clustered together (FIG. 1). From these groupings, A representative clone was selected from each group based on expression levels in *E. coli* Rosetta-gami™ B cells and is indicated to the left of the box, thus narrowing the list of Fabs to 12 clones for further analysis.

Example 3

Figure 2:
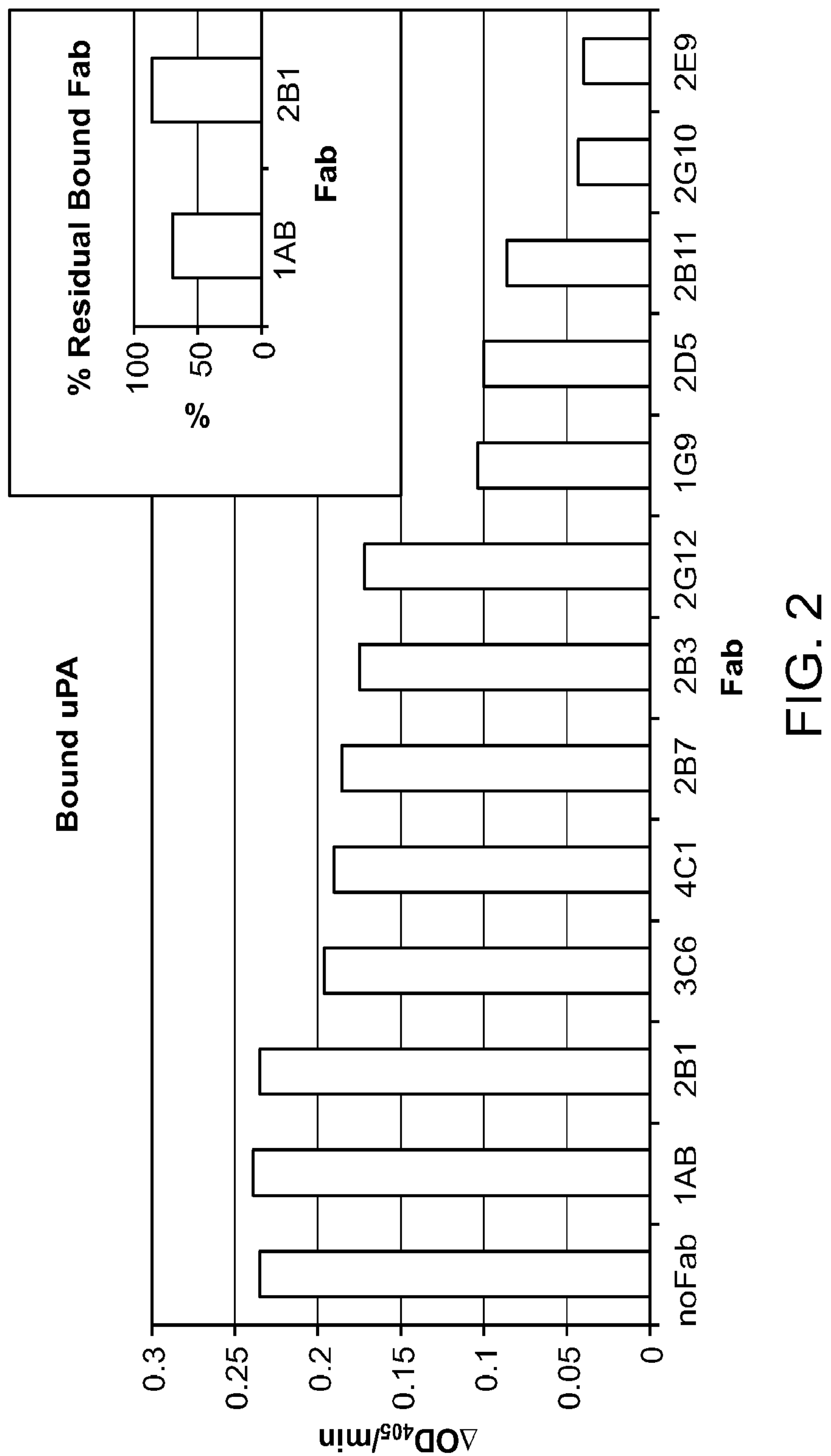
FIG. 2: Binding of uPA to uPAR in the presence of Fab. The ratio of bound Fab in the presence of uPA to bound Fab in the absence of uPA is reported as a percentage.

Competitive ELISA Identifies 2E9 and 2G10 as the Most Competitive with uPA for uPAR Binding Purified Fabs from the 12 remaining clones were analyzed for their ability to compete with uPA for binding to immobilized uPAR. The presence of uPA was measured by the amount of bound proteolytic activity in the presence and absence of each Fab (FIG. 2). The presence of uPA was determined by the amount of bound proteolytic activity and is reported as initial velocities from progress curves. Maximal uPA binding was determined by incubating uPA without Fab and is labeled "no Fab". Data is plotted left to right from Fabs that do not compete with uPA for uPAR binding to Fabs that show maximal competition. For 1A8 and 2B1, the amount of Fab bound to uPAR in the presence and absence of uPA was determined by ELISA. This assay identified 2E9 and 2G10 as competitors of the uPA/uPAR interaction. Controls showed that these antibodies did not directly inhibit uPA's proteolytic activity.

The competitive ELISA data also suggested that 1A8 and 2B1 do not compete with uPA for uPAR binding. To verify that these Fabs were not weak uPA competitors, the ratio of bound Fab in the presence of uPA to bound Fab in the absence of uPA was calculated (FIG. 2, inset). The amount of Fab bound in the presence and absence of uPA was determined in the same uPAR coated well, therefore some loss of Fab is expected due to processing between measurements. This assay verified that 1A8 and 2B1 bound a non-uPA binding site on uPAR. The two strongest non-competitive binders, 1A8 and 2B1, and the two strongest competitive inhibitors, 2G10 and 2E9, were chosen for further analysis.

Example 4

Figure 3:
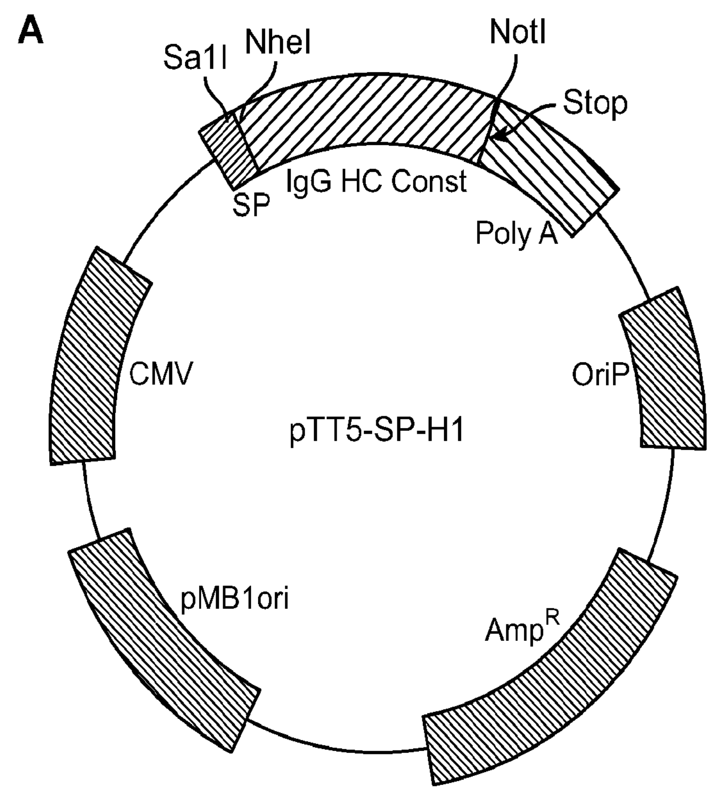
FIGS. 3A-3B: IgG expression by transient transfection. Panel A, Fab sequences were grafted onto an IgG1 scaffold by independently sub-cloning the heavy and light chain sequences into pTT5-SP-H1. Panel B, SDS-PAGE analysis of purified antibodies is shown.
Figure 3:
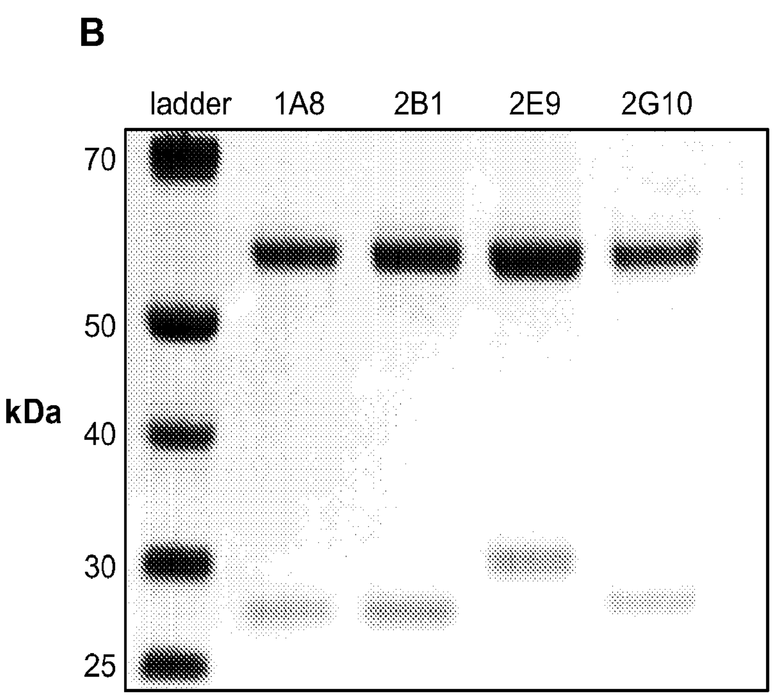

Full-Length IgG Expression in Mammalian Cells Produces Robust Amounts of Antibody The heavy and light chain sequences of 1A8, 2B1, 2G10, and 2E9 were cloned into the mammalian expression vector pTT5-SPH1 for high-level expression by transient transfection in HEK-293-EBNA1 cells. The plasmid map of this transient expression vector is shown in FIG. 3. For a given antibody, both the pTT5-SP-H1-heavy chain vector and pTT5-SP-H1-light chain vector were co-transfected into HEK-293-EBNA1 cells for expression. Co-transfection of varying ratios of heavy and light chain expression plasmids revealed that an equal mass of heavy and light chain DNA, which corresponds to a slight excess of light chain plasmid particles in comparison to heavy chain ones, produced the highest level of antibody. A total DNA:PEI ratio of 1 μg:4 μl and sub-confluent maintenance of HEK 293-EBNA1 cells resulted in greater than 90% transfection efficiency. Optimal time to harvest post transfection was four to five days. Antibody expression yield was sequence dependant and varied between 20 mg/L to 100 mg/L of culture supernatant at the 1 ml scale, and between 10 mg/L and 50 mg/L in large scale trials (500 ml).

Example 5

Surface Plasmon Resonance Reveals Low nM Affinities for uPAR

Figure 4:
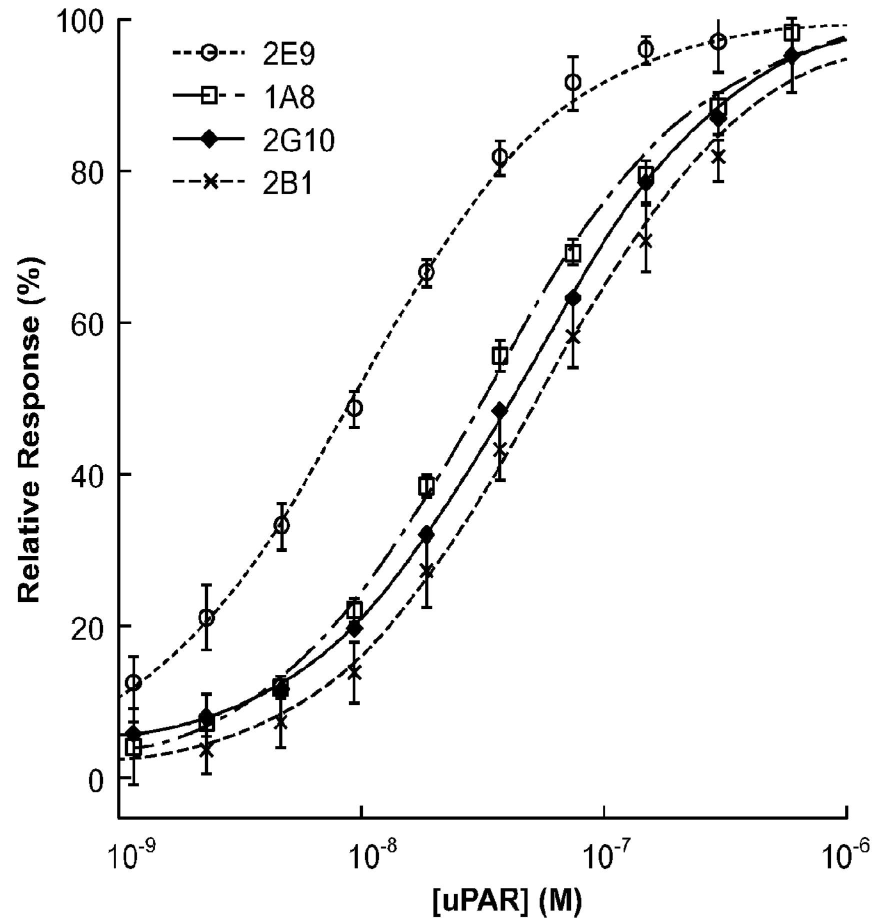
FIG. 4: Equilibrium affinity determination of uPAR antibody interaction. Percent of maximal surface plasmon resonance response during analyte (uPAR) injection versus analyte concentration is shown. Curve fitting for 2E9 (open circle), 1A8 (open square), 2G10 (closed diamond), and 2B1 (x) yielded $K_D$ values that are summarized in the table.

The monovalent interaction affinity between uPAR and the antibodies 1A8, 2B1, 2G10, and 2E9 were determined by equilibrium surface plasmon resonance methods using a Biacore 1000. Analysis of instrument response versus analyte (uPAR) concentration yielded monovalent dissociation constants in the nanomolar range (FIG. 4).

Example 6

Flow Cytometry Shows Specific Labeling of uPAR Expressing Cells

Figure 5:
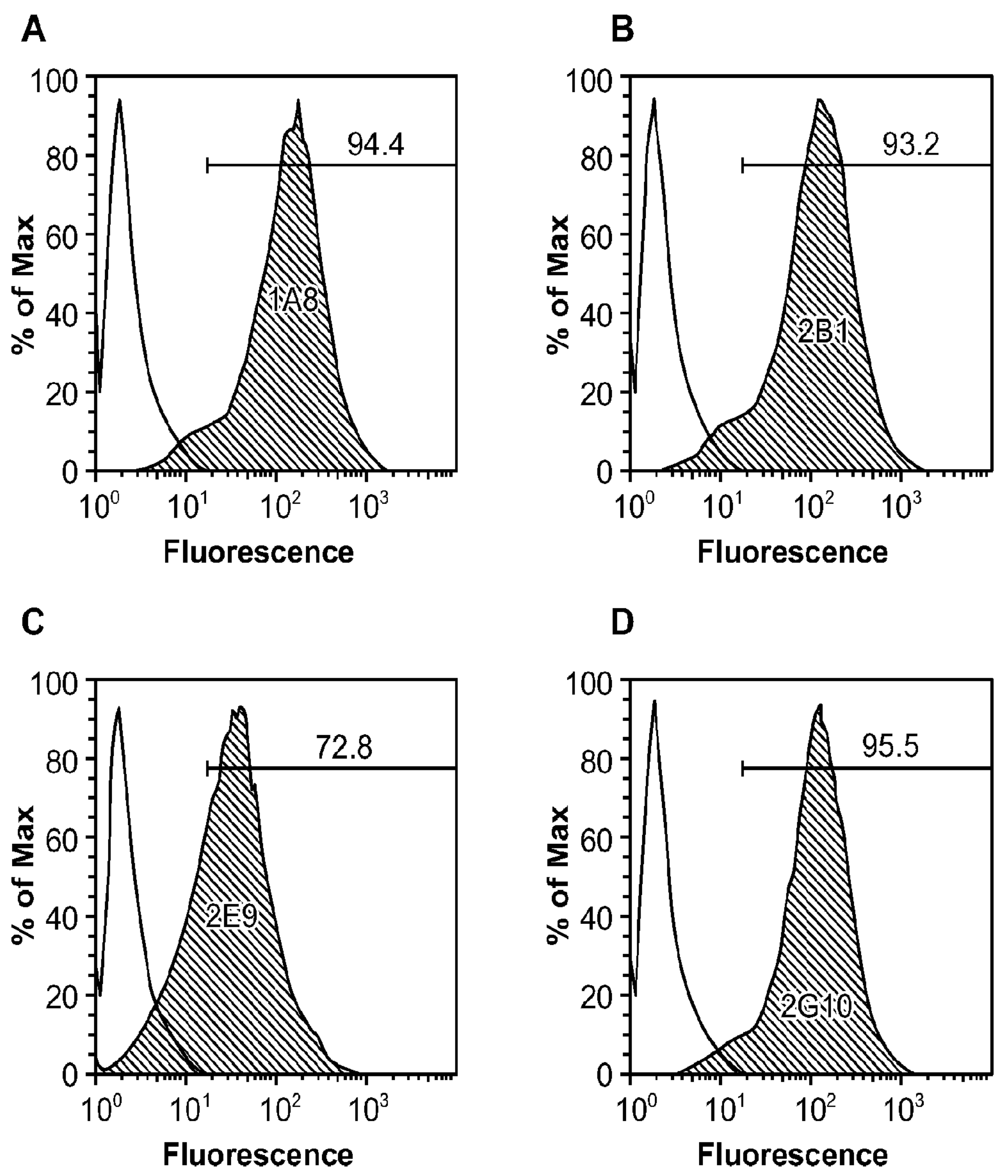
FIGS. 5A-5D: Detection of HEK cell surface uPAR with human anti-uPAR antibodies. (Panels A-D), white profiles represent staining with control whole human IgG; shaded profiles represent staining with human anti-uPAR antibody. The identity of the human anti-uPAR antibody is indicated within the shaded profile (Panel A=1A8, Panel B=2B1, Panel C=2E9, Panel D=2G10).

The ability of the identified antibodies to bind uPAR, as it is presented on the cell surface, was analyzed by flow cytometry. HEK-293 cells stably expressing membrane-bound human uPAR were labeled with full-length anti-uPAR IgGs, or an isotype control. Anti-uPAR IgGs were detected with an anti-human Fc FITC-conjugated secondary antibody. Labeled cells were analyzed on a flow cytometer (FIG. 5). To quantify the relative staining intensities of the human anti-uPAR antibodies, the same gate (horizontal line as shown in FIG. 5) was applied to each sample. The % of cells staining positive for uPAR expression is indicated above the gate. All the antibodies tested indicated robust labeling of uPAR-expressing HEK-293 cells, but did not show labeling of the parental HEK-293 cells lacking uPAR expression.

Figure 11:
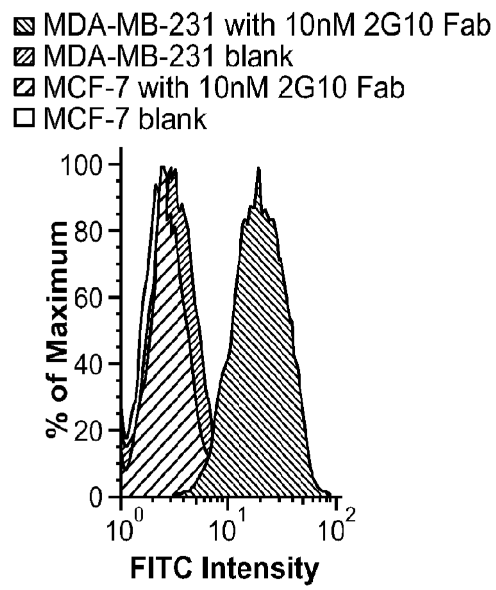
FIG. 11: Binding of 2G10 Fab to cancer cell lines expressing high levels of uPAR (MDA-MB-231) and to another cancer cell line expressing low levels of uPAR (MCF-7). Fitc fluorescence indicates amount of antibody bound. Cells were also analyzed in the absence of antibodies.

Similar experiments were carried out for 2G10 Fab using cancer cell lines. MCF-7 (low uPAR expression) and MDA-MB-231 (high uPAR expression) are two breast cancer cell lines whose relative expression of uPAR were previously characterized. MCF-7 cells and MDA-MB-231 cells were contacted with 2G10, and the binding of 2G10 was able to discriminate between these two cell lines, consistent with the levels of uPAR (FIG. 11).

Example 7

IgG Labels uPAR-Positive Tumors but not uPAR-Negative Ones

Figure 6:
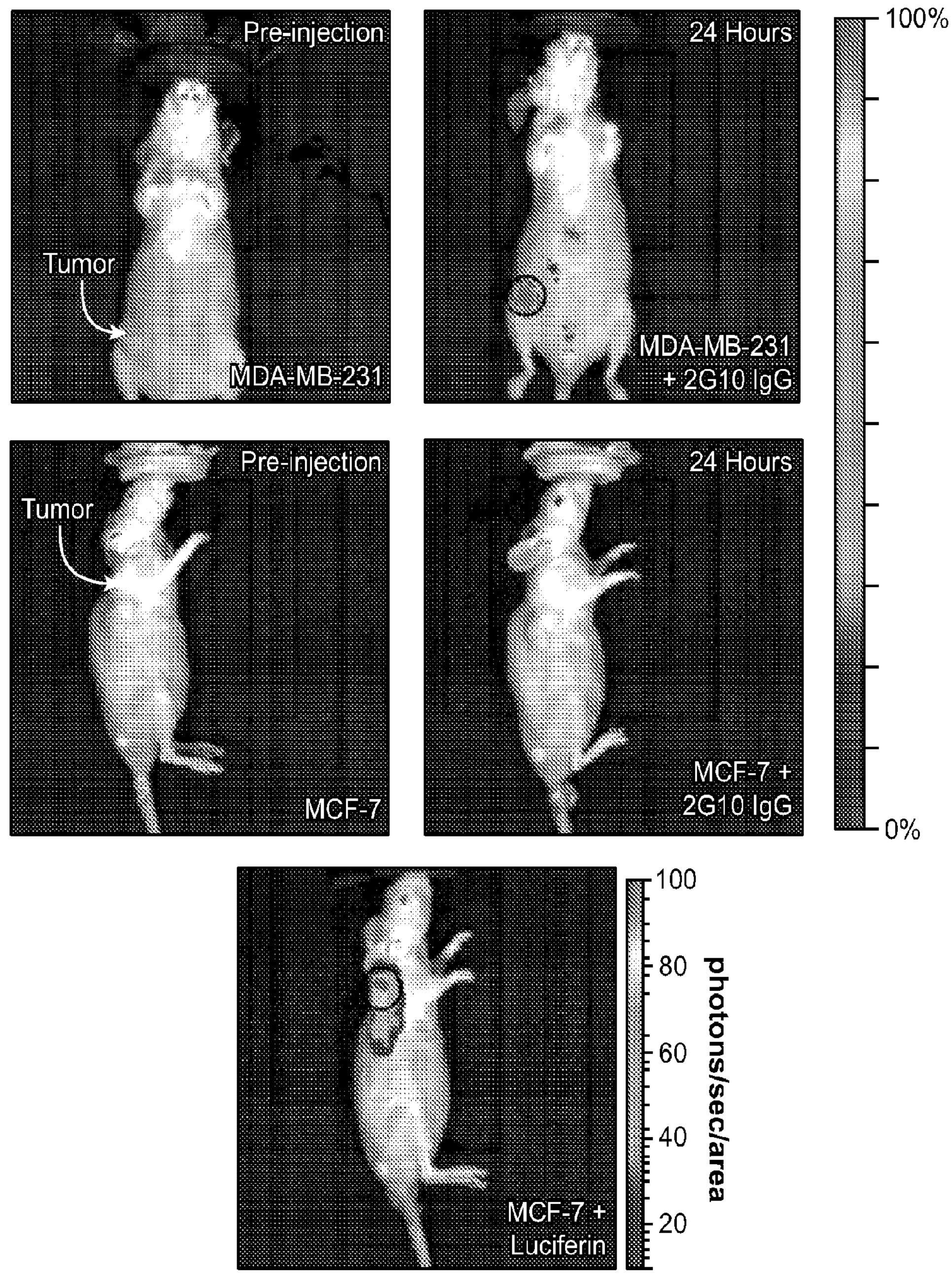
FIG. 6: In vivo images of tumor xenografts in nude mice. Tumor was labeled using 2G10 IgG or visualized via luciferase-expressing cells. Upper left: mouse with MDA-MB-231 tumor. Upper right: mouse with MDA-MB-231 tumor labeled with 2G10 IgG. Lower left: mouse with MCF-7/Luc+ tumor. Lower right: mouse with MCF-7 tumor labeled with 2G10 IgG. Bottom: mouse with MCF-7/Luc+ tumor contacted with luciferin for visualization. Circled regions point to areas of high signal from labeled 2G10 IgG or luciferase activity.

To test the binding of the antibodies in vivo, fluorescently labeled 2G10 IgG were used to image uPAR-expressing breast tumor xenografts in nude mice. Cancer cells lines known to express uPAR were pre-screened for 2G10 binding via flow cytometry. Two breast cell lines were chosen; MDA-MB-231 for its ability to be labeled by 2G10, and MCF-7 for its inability to be detectably labeled. As shown in representative mice in FIG. 6, 2G10 IgG was able to label uPAR-expressing MDA-MB-231 tumor xenografts, but not MCF-7 ones. Although the figure shows the 24-hour time point for the MDA-MB-231, when the signal intensity was highest, the signal persisted over one week, indicating that these antibodies may have favorable pharmacokinetics.

Figure 13:
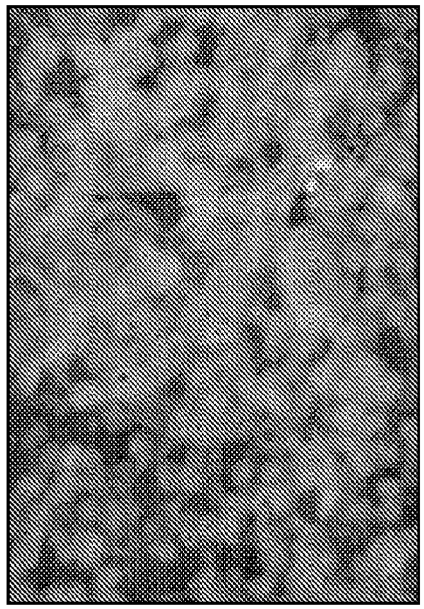
FIGS. 13A-13C: Fluorescence micrographs of MDA-MB-231 cells stained with Alexa-Fluor 488-labeled 2G10 Fab (Panel A) or fitc-labeled 3C6 Fab (Panel B). Cells were also stained with DAPI. Panel C, 2G10 Fab staining of paraffin-embedded breast tumor.
Figure 13:
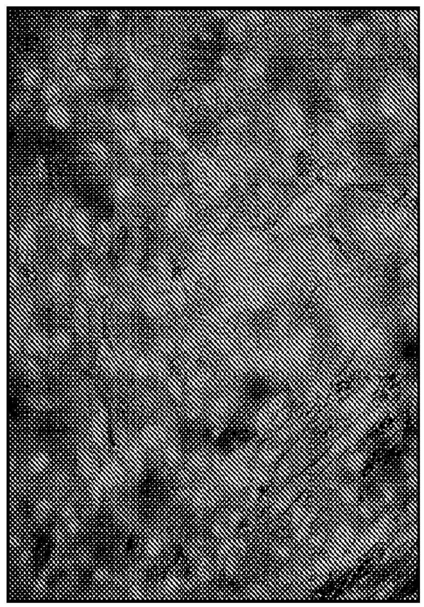
Figure 13:
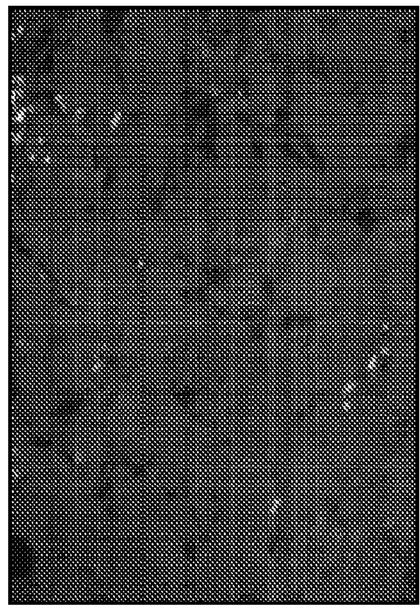

Sections were taken from MDA-MB-231 tumor xenographs and embedded in paraffin. These sections were labeled with Alexa Fluor 488-labeled 2G10 Fab (Panel A) and FITC-labeled 3C6 Fab (Panel B) to probe for uPAR (FIG. 13). Staining patterns of 2G10 and 3C6 differ and this difference suggests that 2G10 and 3C6 bind to different uPAR epitope. Ability of staining of 2G10 Fab to stain paraffin-embedded aggressive breast tumor is shown in Panel C of FIG. 13. 2G10 was able to bind to its uPAR epitope under the harsher preservation conditions of formalin fixation followed by paraffin embedding. 2G10 staining was found to be more intense in some cells than others. High-intensity-stained cells might be macrophages. These antibodies were found to be specific for uPAR because probing against paraffin-embedded engineered HEK 293 cell line that over-expresses membrane-bound uPAR results in a high binding signal while parent HEK 293 cell line does not.

Figure 12:
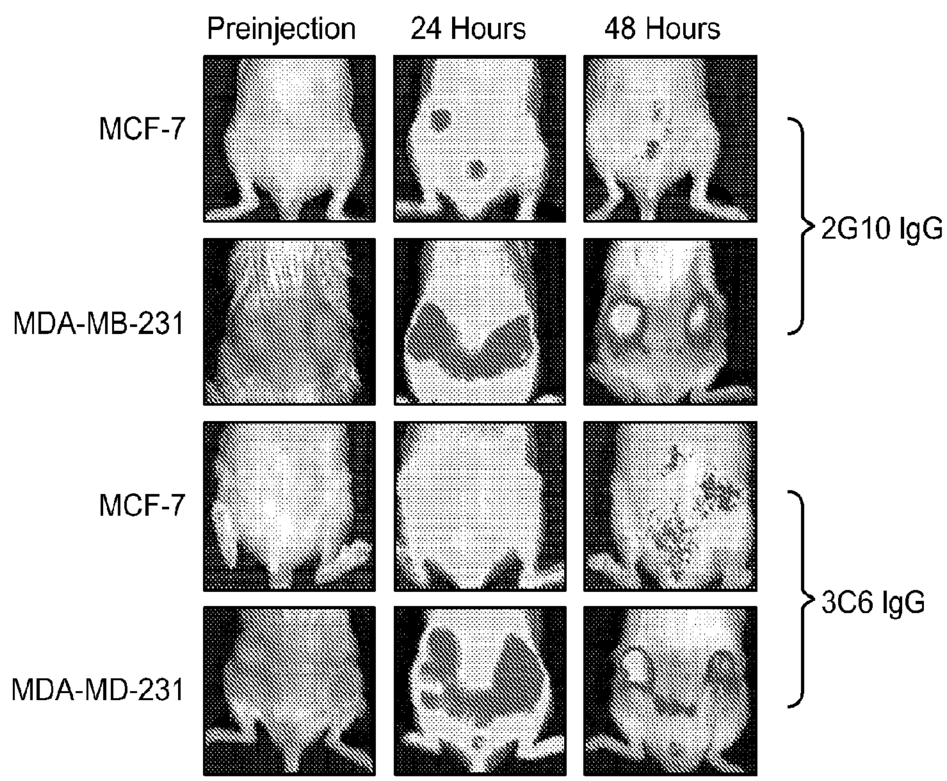
FIG. 12: In vivo images of immune-compromised mice that have been injected with two different cancer cell lines. The cancer cell line expressing high levels of uPAR is MDA-MB-231 and the cancer cell line expressing low levels of uPAR is MCF-7. After palpable tumors appeared, two nmol of labeled 2G10 IgG or 3C6 IgG were injected into the mice.

Additional in vivo experiments were carried out using immune compromised mice implanted the high- or low-uPAR expressing cell lines (MDA-MB-231 and MCF-7, respectively) (FIG. 12). After a period of time post-implantation for palpable tumors to appear, two nanomoles of labeled 2G10 or 3C6 IgG antibody were injected into the mice. After 48 hour post injection, photographs of the mice stained with the antibodies were taken. Uptakes of antibodies were observed in the uPAR expressing tumors derived from MDA-MB-231 cells, but not in the tumors derived from uPAR deficient cells (MCF-7). Both antibody antagonists 2G10 and 3C6 produced the same results (upper two rows and bottom two rows).

Example 8

2E9 and 2G10 Decrease H1299 Invasion

Figure 7:
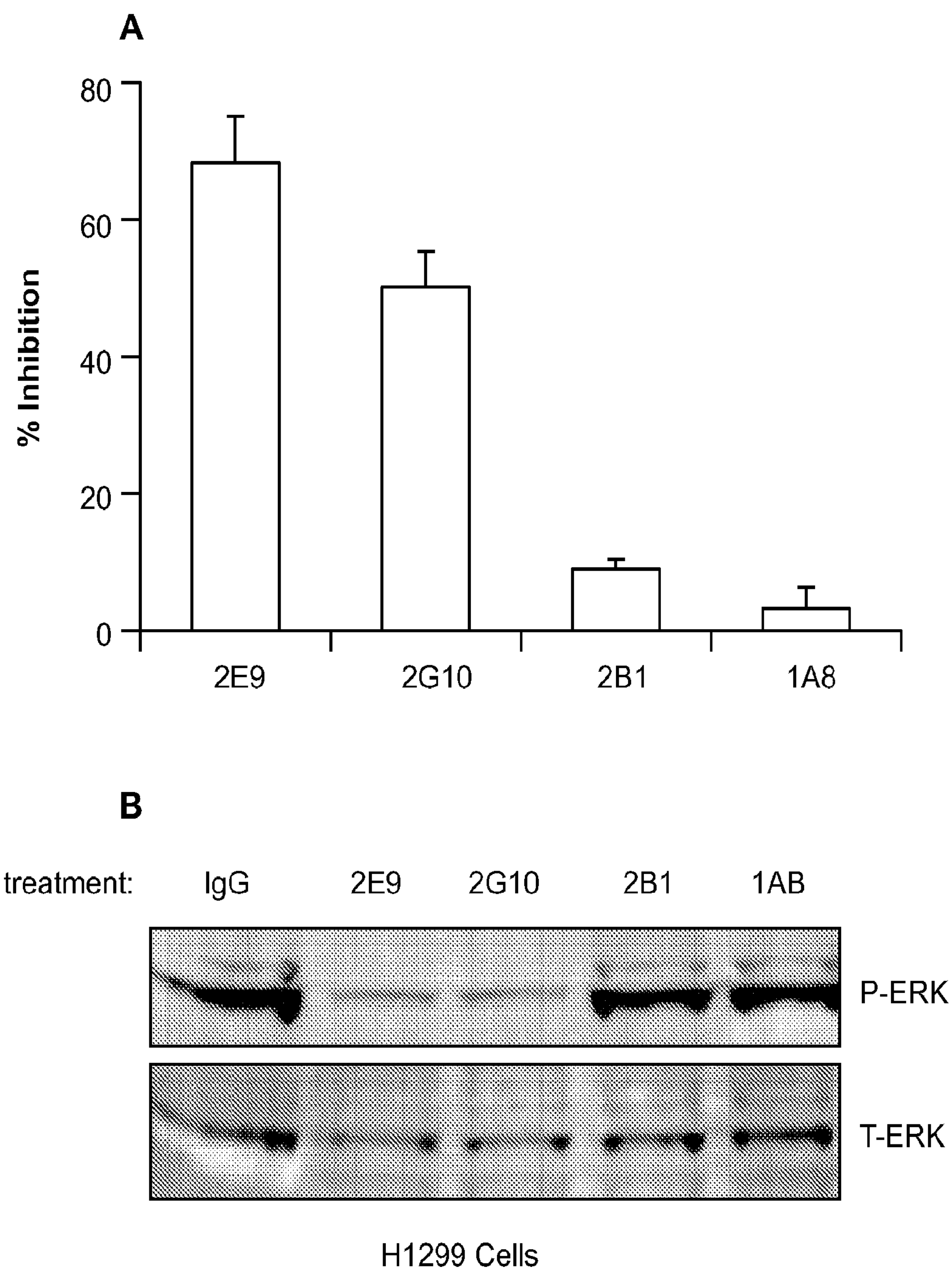
FIGS. 7A-7B: Inhibition of uPA/uPAR mediated invasion and signaling in H1299 cells. Panel A, The results of Matrigel invasion experiment are expressed as percent inhibition of the invasion observed with no treatment control. Panel B depicts the results of an experiment testing for the effect of antibodies on the phosphorylation of ERK (extracellular signal-regulated kinases).

H1299 cells have also been shown in vitro to migrate through, or invade, extracellular matrix components such as Matrigel in a manner that is dependent on uPA binding to uPAR (Tang et al. (2008) *J Cell Sci* 121:3747-3756). A strong in vitro Matrigel invasion phenotype is thought to correlate with the metastatic potential of a cancer cell in vivo. For the experiments shown in panel A of FIG. 6, H1299 cells were pre-treated with antibodies (10 μg/ml): 2E9, 2G10, 2B1, and 1A8 before they were allowed to invade Matrigel for 24 hours. The cells that migrated through and attached to the bottom of the filter were fixed, stained with Giemsa, and extracted with 10% acetic acid. Cell invasiveness is evaluated by measuring $OD_{595\ nm}$. Analysis of the effects of antibodies 1A8, 2B1, 2G10, and 2E9 on Matrigel invasion by H1299 cells shows that 2G10 and 2E9 are both capable of inhibiting migration, whereas 1A8 and 2B1 are not (FIG. 7, panel A).

Example 9

2E9 and 2G10 Decrease uPA-Dependent Eric Phosphorylation in H1299 Cells

The human lung cancer cell line H1299 exhibits pro-proliferative ERK phosphorylation and activation that is dependant on signaling events mediated by binding of uPA to uPAR. This cell line was used to test the ability of the anti-uPAR antibodies to inhibit uPAR-dependant pro-proliferative signals triggered by uPA binding. H1299 cells expressing endogenous uPAR were serum-starved, acid washed, pre-treated with antibodies (10 μg/ml), and then incubated with pro-uPA (10 nM). The lysates were immuno-blotted with anti-pERK (top panel) and anti-total ERK (bottom panel) (FIG. 7, panel B).

The results demonstrate that antibodies 1A8 and 2B1 do not inhibit ERK phosphorylation under the conditions tested. However, 2E9 and 2G10, which compete with uPA binding to uPAR, are able to inhibit ERK phosphorylation.

Example 10

3C6 Decreases FN-Dependent ERK Phosphorylation in H1299 Cells, and Abrogates their FN- and VN-Dependent Adhesion The activation of FN-dependent ERK phosphorylation in H1299 cells is dependent on the formation of the uPAR/β1/FN complex. To determine if any of the unique anti-uPAR Fabs interfere with the uPAR/β1 interaction, their ability to decrease ERK phosphorylation in H1299 cells seeded in FN-coated wells was tested. Similar to the experiments in Example 9, H1299 cells were serum-starved, acid washed, were pre-treated with Fabs (10 μg/ml): 2B1, 2B7, 2B11, 2D5, 2E9, 2G10, 2G12, 3C6, and 4C1, and cultured on a FN-coated surface (10 μg/ml) for 30 minutes before lysis. The lysates were immuno-blotted with anti-pERK (top) and anti-total ERK (bottom) (FIG. 8, panel A). 3C6 was identified as able to significantly decrease FN-dependent ERK phosphorylation.

Figure 8:
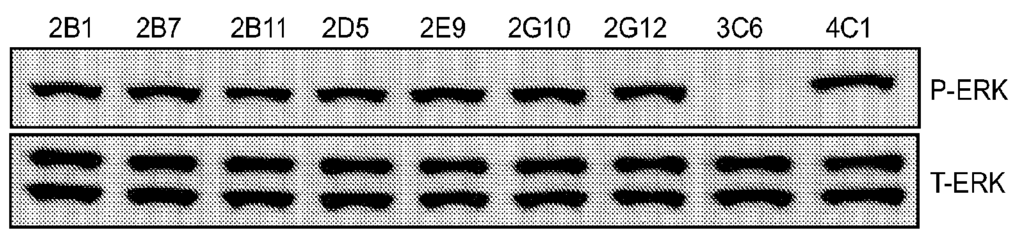
FIGS. 8A-8C: Determination of 3C6 as a putative uPAR/β1 integrin antagonist. Panel A depicts the effects of antibody on the phosphorylation of ERK. Panel B shows adhesion assays in which 2G10 (uPAR/uPA antagonist) is directly compared with 3C6 (uPAR/β1 integrin antagonist). Panel C is a normalized graph comparing the adhesion of antibody treatment on the two different ECM coating.
Figure 8:
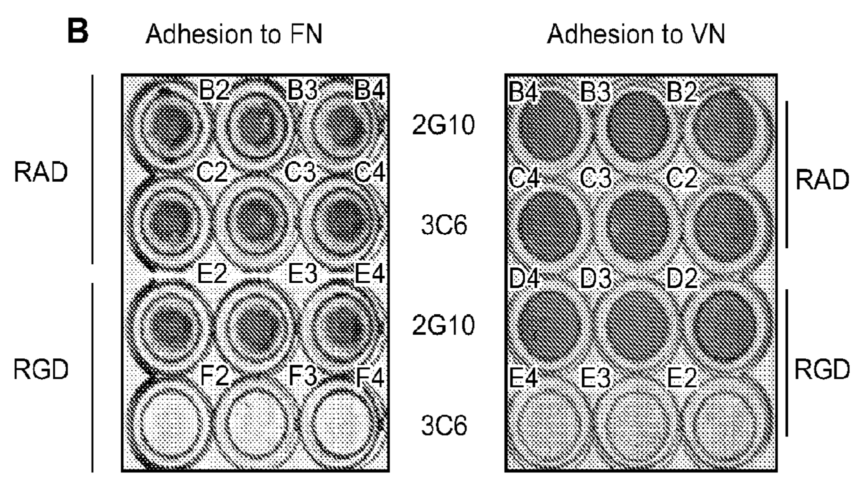
Figure 8:
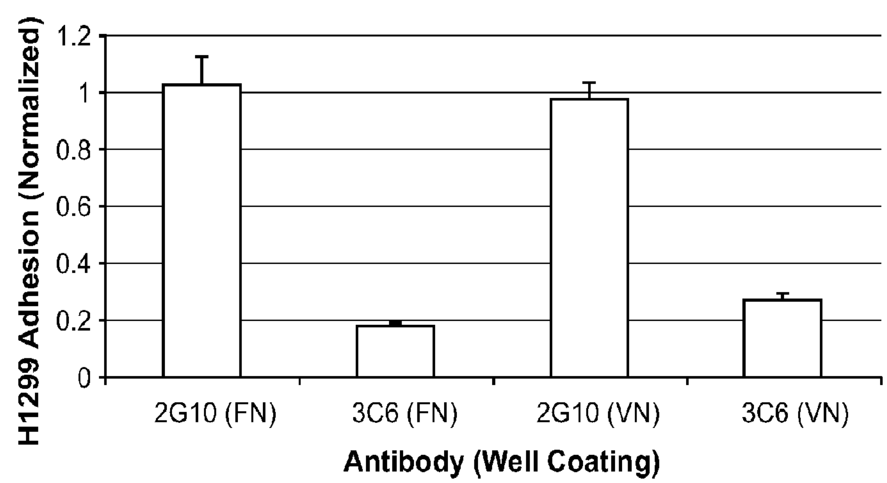

To further characterize the functional effects of 3C6, a FN adhesion assay was utilized. The β1/FN interaction can occur in a uPAR-independent context that is sensitive to antagonism by the RGD peptide, and in a uPAR-dependent context that is resistant to the RGD peptide (Wei et al. (2007) *J Biol Chem* 282:3929-3939). H1299 cells were seeded on FN-coated (10 μg/ml) or VN-coated (5 μg/ml) 96-well plates with or without anti-uPAR antibody, and RGD or RAD peptide. In the presence of both the RGD peptide and 3C6, H1299 adhesion to FN-coated wells was completely abrogated (FIG. 8, panel B). The selectivity of this effect was verified by inclusion of RAD peptide and the Fab form of the uPA competitor, 2G10, as negative controls.

To determine if 3C6's ability to disrupt uPAR/β1 integrin-mediated adhesion is generalizable, the ability of uPAR/α3β1-mediated H1299 cell adhesion to VN was characterized. In an assay similar to the FN adhesion assay, it was found that 3C6 could also prevent the adhesion of H1299 cells to VN in the presence of RGD peptide (FIG. 8, panel B), suggesting that 3C6 is able to specifically block the functions of uPAR complexes with multiple β1 integrins. As seen in panel C of FIG. 8, a normalized graph comparing the adhesion for each antibody treatment on the two different ECM coatings was obtained by dividing the average reading from RGD-treated wells by that from RAD-treated wells. It was found that 3C6 treatment disrupts uPAR-mediated integrin adhesion at least four fold more than 2G10 treatment.

Example 11

3C6 Fab Binds uPAR Over-Expressing HEK Cells

To confirm that 3C6 recognizes uPAR as displayed on a cell's surface, the same flow cytometry assay used to characterize the anti-uPAR IgGs was used here. Since the investigation of 3C6-dependent cellular effects was done with the Fab form of the antibody, this format of the antibody (e.g. Fab) was used for flow cytometry. 2G10 Fab was included as a benchmark for an antagonistic antibody's ability to bind cellular uPAR-expressing HEK-293 cells. HEK 293 cells over-expressing uPAR were stained with 3C6 and 2G10 to confirm 3C6's ability to bind cell surface uPAR. The results are shown in panel A of FIG. 9. The dashed white profile represents staining with 2G10 Fab; the shaded profile represents staining with 3C6 Fab; the solid white profile represents no Fab staining, but inclusion of the AlexaFluor 488 conjugated secondary. The data indicate that 3C6 can bind to cells that over-express uPAR, albeit not as robustly as the 2G10 Fab.

Example 12

3C6 Prevents the Association of uPAR and α5β1 in H1299 Cells

To determine if 3C6 directly blocked uPAR's association with α5β1 integrin, 3C6 and 2G10 were used to immunoprecipitate uPAR from H1299 lysates. H1299 lysates were incubated with anti-uPAR Fab (2G10 or 3C6), Penta-His antibody, and Protein A/G agarose. The resulting immunoprecipitates were analyzed Western blot for both uPAR and α5β1 integrin.

Figure 9:
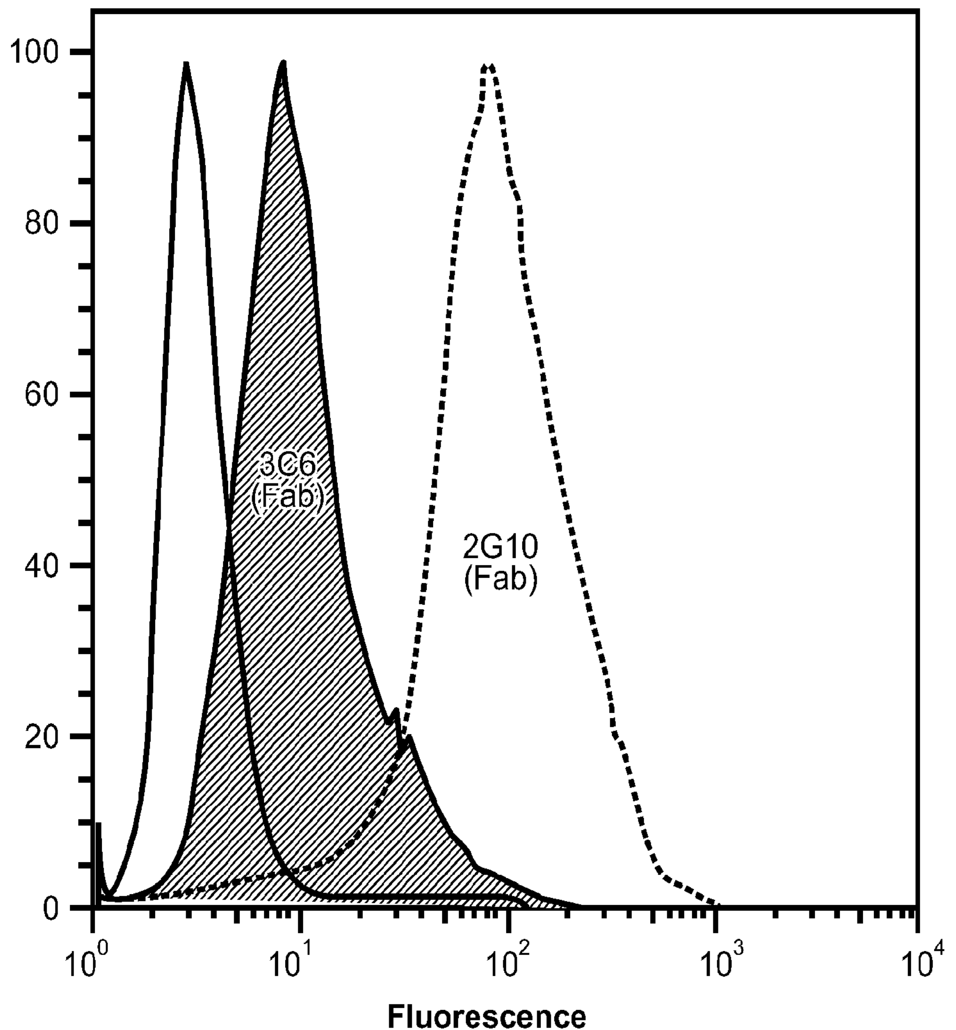
FIGS. 9A-9B: 3C6 binds to cell surface uPAR and abrogates uPAR association with α5β1 integrin. Panel A depicts the results of a binding experiment to uPAR-expressing cells. Panel B depicts the results of an Immunoprecipitation experiment to investigate the effects of antibodies on uPAR's association with β1 integrin.
Figure 9:
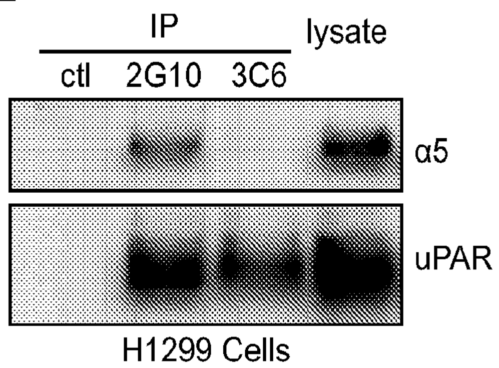

The resulting immunoprecipitates were analyzed by Western blot for both uPAR and α5β1 integrin. The results indicate that 3C6 prevents uPAR's association with α5β1 integrin, while 2G10 does not (FIG. 9, panel B).

Example 13

3C6 Decreases H1299 Invasion, and 2G10 and 3C6 Synergistically Inhibit H1299 Invasion Through Cross-Linked Matrices Migration is a complex phenomenon that requires modulation of adhesion and degradation of ECM. As shown in FIG. 7, panel A, antagonism of the uPAR/uPA complex by 2E9 and 2G10 inhibits the invasion of H1299 cells. To determine if 3C6 has a similar effect on invasion by antagonizing the uPAR/β1 complex, the potential synergy of. 3C6 Fab with the uPA competitor Fab, 2G10, was tested for their ability to block cell invasion through Matrige/Collagen I or Collagen I. H1299 cells were pre-treated with antibodies (2G10, 3C6, and 2G10/3C6 at 5-10 μg/ml) before seeding on the Collagen I-coated (FIG. 10, panel A) or Matrigel/Collagen I-coated (FIG. 10, panel B) top membrane of a 24-well Transwell plate ($10^5$ cells/well in triplicate). Cells were incubated for 24 hours. The cells that migrated through and attached to the bottom of the filter were fixed, stained with Giemsa, and extracted with 10% acetic acid. Cell invasiveness is evaluated by measuring $OD_{595\ nm}$. The results are expressed as a percentage of inhibition observed in the no treatment control. As shown in panel A of FIG. 10, not only do 2G10 and 3C6 Fabs inhibit invasion through Collagen I, but combined dosage also exhibits a synergistic response.

Figure 10:
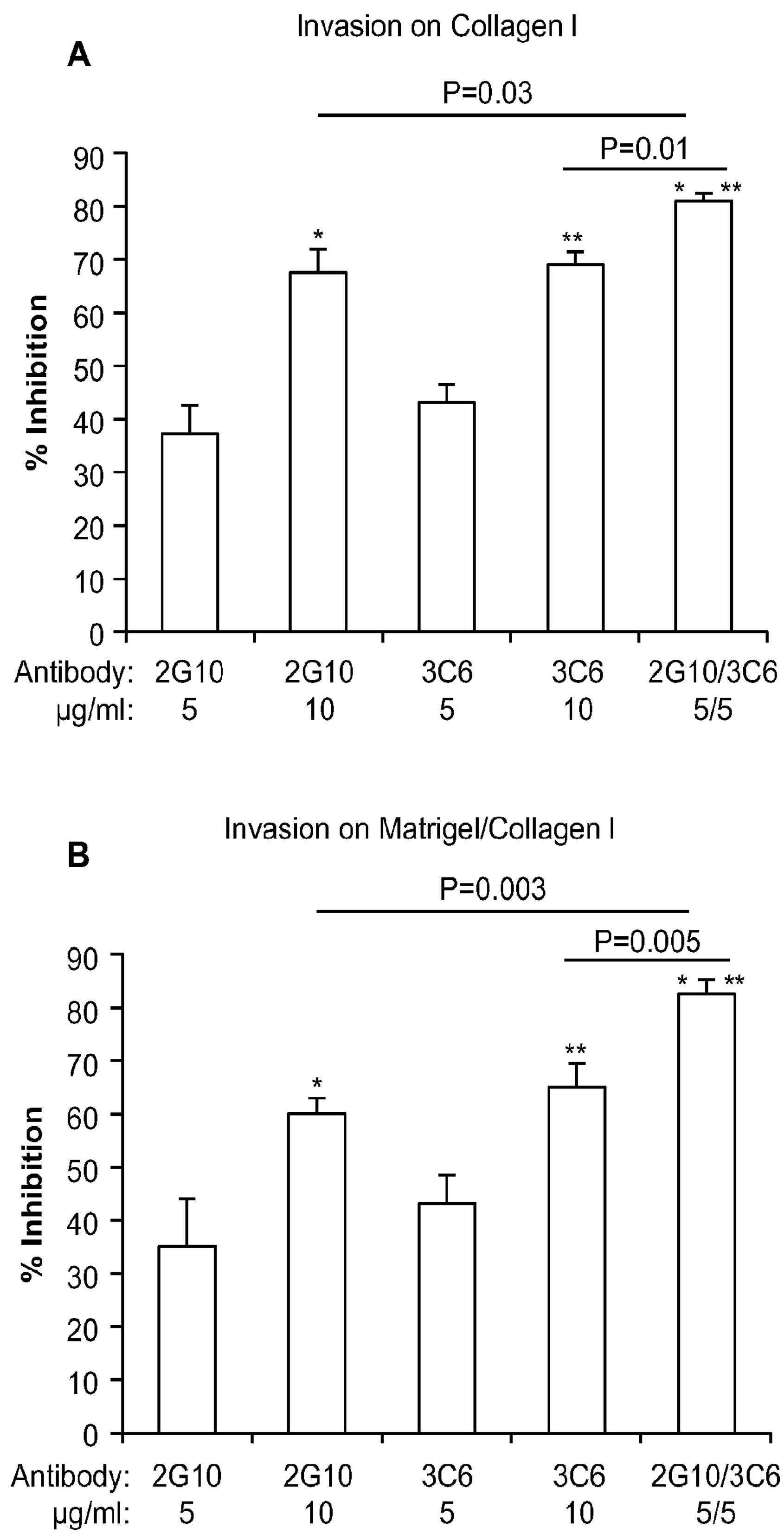
FIGS. 10A-10B: A combined treatment using 2G10 and 3C6 cells results in a synergistic effect of decreasing the invasive potential of H1299 through Matrigel/Collagen I and Collagen I. Experiments were carried out using H1299 cells pre-treated with antibodies and seeded on the Collagen I-coated (panel A) or Matrigel/Collagen I-coated (panel B) top membrane of a 24-well Transwell plate.

Additionally, the invasion assay was repeated on a substrate comprised of both Matrigel and collagen I, to provide a matrix that contained more physiologically relevant cues for migration and ECM degradation. The results were consistent for what was observed on the collagen I coated inserts with concurrent 2G10 and 3C6 treatment resulting in a synergistic response (FIG. 10, panel B).

Example 14

Radiolabeling DOTA-2G10 IgG with $^{111}$In and In Vivo SPECT/CT Imaging

Figure 14:
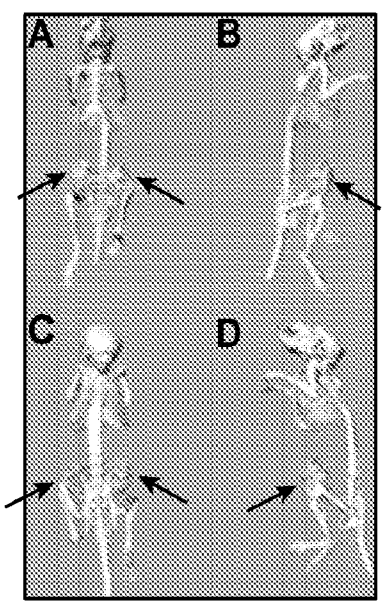
FIG. 14: Amira-processed representation of an MDA-MB-231-xenograph mouse imaged with $^{111}$In-DOTA-2G10 at 48 hr post-injection of 2G10 IgG (250 μCi). The CT skeletal image can be seen in white. Dark gray represents the tumors. Panel A, ventral; Panel B, sagittal view at 90°; Panel C, dorsal; Panel D, sagittal view at 180°. Arrows point to the location of where the antibody binds, which corresponds to the location of the tumors.

For radiolabeling, the DOTA-2G10 IgG was diluted to 2 μM with 1×PBS. This corresponds to a weight by volume concentration of around 250 μg/ml. A 200 μl DOTA-2G10 IgG aliqout (50 μg of IgG) was incubated with 12 μl of $^{111}InCl_3$ (2.59 mCi) in 0.01N HCl for 50 minutes at 37° C. Using radio TLC, the labeling efficiency of the $^{111}$In with the DOTA chelate was determined to be 90%. The radiolabeled antibody was separated from unreacted $^{111}InCl_3$ by size-exclusion chromatography using a PD-10 column pre-equilibrated with 1×PBS buffer. 0.5 ml fractions were collected from the column and were assayed for the presence of radiolabeled IgG by radio TLC. Fractions with high radioactive purity were then injected into the tail vein of six-week old nude mice bearing MDA-MB-321 cancer xenografts of approximately 400 $mm^3$ in size. Injection was done with 250 μCi of 2G10 IgG. The mice were then imaged at 48 hr using a Gamma Medica Ideas X-SPECT SPECT/CT scanner. CT and SPECT images were reconstructed and fused together using the software provided by the manufacturer. The data were then analyzed using Visage Imaging Amira software. A processed image of the MDA-MB-321 xenograph labeled with $^{111}$In-DOTA-2G10 IgG is shown in FIG. 14 with four different views. As indicated by regions that are dark gray, 2G10 specifically labeled uPAR-expressing tumors. Doral, ventral and saggital views of the MDA-MB-321 xenograph are also shown in various panels in FIG. 14.

Example 15

2G10 can Induce Cytostatic State in MDA-MB-231 Cells

Figure 15:
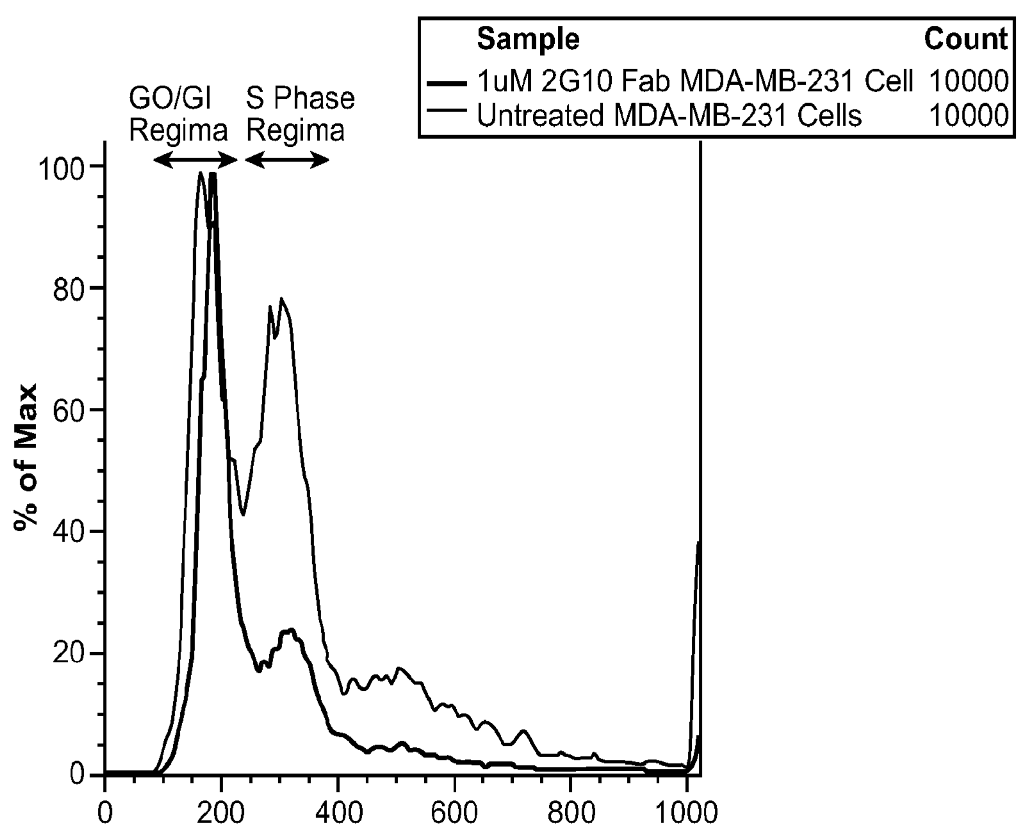
FIG. 15: A flow cytometry graph demonstrating the cytostatic states of MDA-MB-231 cells treated or untreated with 2G10 Fab.

MDA-MB-231 cells were treated with 1 μM of 2G10 Fab for four days to assess any level of cell death or cytostatic properties using propidium iodide staining. Cytostatic properties refer the inhibition of growth and/or division of cells. As shown by the flow cytometry experiment in FIG. 15, 2G10 induced a cytostatic state in the treated cells, trapping them in the G0/G1 cell cycle state.

Example 16

Epitope Mapping of 3C6 onto Alanine-Scanned uPAR Mutants

Figure 16:
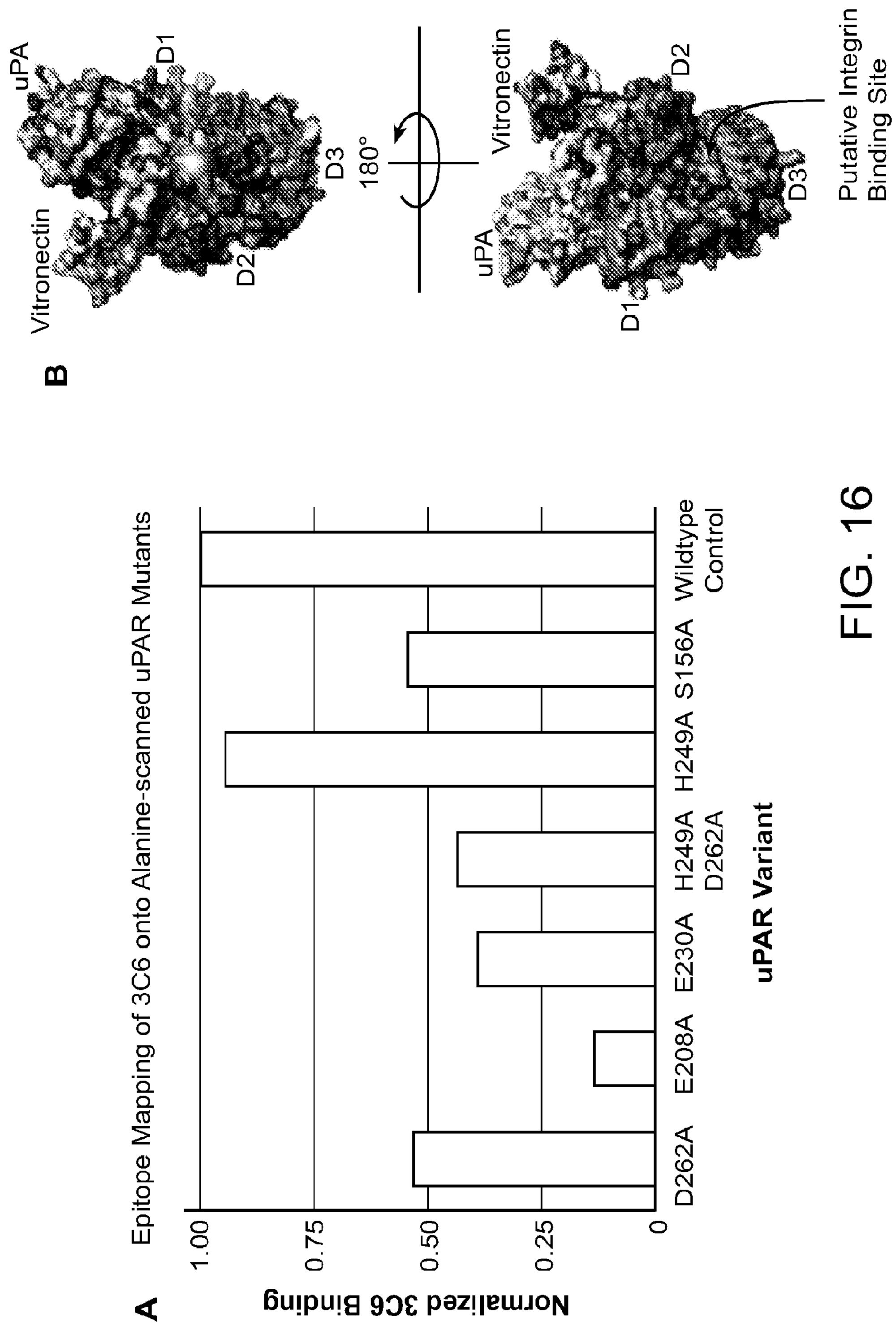
FIGS. 16A-16B: Epitope mapping experiments for 3C6 using alanine-scanned uPAR mutants (panel A); front (top) and back (bottom) representation of the uPAR structure. Arrow points to the integrin binding site (panel B).

To provide initial analysis for the binding epitope of integrin competitor antibody, 3C6, a flow cytometry based epitope mapping studying was conducted on alanine-scanned mutants of uPAR. Shown in FIG. 16, panel A is a representation of the results. Each mutation is located in domain 3 of uPAR and affect 3C6 binding to lesser or greater extents. Accordingly, all the uPAR mutants considered are present in domain 3 of uPAR, which is implicated as the major contributor to β1 integrin binding. This site is located opposite side of the uPA binding site (FIG. 16, panel B).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An isolated antibody or antigen-binding fragment thereof that specifically binds urokinase-type plasminogen activator receptor (uPAR), wherein said antibody or antigen-binding fragment competes for binding to uPAR with an antibody or antigen-binding fragment that comprises:

- a VH CDR1 comprising the amino acid sequence of SEQ ID NO:40;
- a VH CDR2 comprising the amino acid sequence of SEQ ID NO:42;
- a VH CDR3 comprising the amino acid sequence of SEQ ID NO:44;
- a VL CDR1 comprising the amino acid sequence of SEQ ID NO:34;
- a VL CDR2 comprising the amino acid sequence of SEQ ID NO:36; and
- a VL CDR3 comprising the amino acid sequence of SEQ ID NO:38.

2. The isolated antibody or antigen-binding fragment of claim 1, wherein said antibody or antigen-binding fragment comprises:

- a VH CDR1 comprising the amino acid sequence of SEQ ID NO:40;
- a VH CDR2 comprising the amino acid sequence of SEQ ID NO:42;
- a VH CDR3 comprising the amino acid sequence of SEQ ID NO:44;
- a VL CDR1 comprising the amino acid sequence of SEQ ID NO:34;
- a VL CDR2 comprising the amino acid sequence of SEQ ID NO:36; and
- a VL CDR3 comprising the amino acid sequence of SEQ ID NO:38.

3. The isolated antibody or antigen-binding fragment of claim 2 comprising:

- a) a heavy chain comprising an amino acid sequence having at least 85% amino acid sequence identity to the full length $V_H$ of 2G10 (SEQ ID NO:16); and
- b) a light chain comprising an amino acid sequence having at least 85% amino acid sequence identity to the full length $V_L$ of 2G10 (SEQ ID NO:17).

4. The antibody or antigen-binding fragment of claim 1, wherein said antibody or antigen-binding fragment competes for binding to uPAR with an antibody from clone 2G10.

5. The isolated antibody or antigen-binding fragment of claim 1, wherein the antibody or antigen-binding fragment is conjugated to a moiety selected from the group consisting of: a cytotoxic molecule, a detectable label, a fluorophore, a dye, a radioisotope, an enzyme, a peptide, a polypeptide, and a nucleic acid.

6. A pharmaceutical composition comprising:

- the isolated antibody or antigen-binding fragment of claim 1; and
- a pharmaceutically acceptable excipient.

7. The pharmaceutical composition of claim 6, wherein the isolated antibody or antigen-binding fragment comprises:

- a VH CDR1 comprising the amino acid sequence of SEQ ID NO:40;
- a VH CDR2 comprising the amino acid sequence of SEQ ID NO:42;
- a VH CDR3 comprising the amino acid sequence of SEQ ID NO:44;
- a VL CDR1 comprising the amino acid sequence of SEQ ID NO:34;
- a VL CDR2 comprising the amino acid sequence of SEQ ID NO:36; and
- a VL CDR3 comprising the amino acid sequence of SEQ ID NO:38.

8. The pharmaceutical composition of claim 7, wherein the isolated antibody or antigen-binding fragment comprises:

a) a heavy chain comprising an amino acid sequence having at least 85% amino acid sequence identity to the full length $V_H$ of 2G10 (SEQ ID NO:16); and b) a light chain comprising an amino acid sequence having at least 85% amino acid sequence identity to the full length $V_L$ of 2G10 (SEQ ID NO:17).

9. The pharmaceutical composition of claim 6, wherein the composition further comprises an antibody or antigen-binding fragment thereof that competes with an integrin for binding to uPAR, wherein the antibody or antigen-binding fragment that competes with an integrin for binding to uPAR comprises:

a VH CDR1 comprising the amino acid sequence of SEQ ID NO:39;

a VH CDR2 comprising the amino acid sequence of SEQ ID NO:41;

a VH CDR3 comprising the amino acid sequence of SEQ ID NO:43;

a VL CDR1 comprising the amino acid sequence of SEQ ID NO:33;

a VL CDR2 comprising the amino acid sequence of SEQ ID NO:35; and a VL CDR3 comprising the amino acid sequence of SEQ ID NO:37.

10. The pharmaceutical composition of claim 9, wherein the integrin is a β1 integrin.

11. The pharmaceutical composition of claim 10, wherein the β1 integrin is a α5β1 or α3β1.

12. A kit comprising:

the isolated antibody or antigen-binding fragment of claim 1 conjugated to a detectable label; and instructions for using the isolated antibody or antigen-binding fragment to detect uPAR expressing cells.

13. The kit of claim 12, wherein the isolated antibody or antigen-binding fragment comprises:

a VH CDR1 comprising the amino acid sequence of SEQ ID NO:40;

a VH CDR2 comprising the amino acid sequence of SEQ ID NO:42;

a VH CDR3 comprising the amino acid sequence of SEQ ID NO:44;

a VL CDR1 comprising the amino acid sequence of SEQ ID NO:34;

a VL CDR2 comprising the amino acid sequence of SEQ ID NO:36; and a VL CDR3 comprising the amino acid sequence of SEQ ID NO:38.

14. An isolated antibody or antigen-binding fragment thereof that comprises the full length $V_H$ of 2G10 (SEQ ID NO:16) and a full length $V_L$, wherein the full length $V_L$ comprises:

a $V_L$ CDR1 comprising the amino acid sequence of SEQ ID NO:34;

a $V_L$ CDR2 comprising the amino acid sequence of SEQ ID NO:36; and a $V_L$ CDR3 comprising the amino acid sequence of SEQ ID NO:38.

15. An isolated antibody or antigen-binding fragment thereof that comprises a full length $V_H$ and the full length $V_L$ of 2G10 (SEQ ID NO:17), wherein the full length $V_H$ comprises:

a $V_H$ CDR1 comprising the amino acid sequence of SEQ ID NO:40 a $V_H$ CDR2 comprising the amino acid sequence of SEQ ID NO:42 and a $V_H$ CDR3 comprising the amino acid sequence of SEQ ID NO:44.

* * * * *